US006461847B1

(12) United States Patent
Ye et al.

(10) Patent No.: US 6,461,847 B1

(45) Date of Patent: Oct. 8, 2002

(54) POLYNUCLEOTIDES ENCODING HUMAN ESTRONE SULFATASES

(75) Inventors: Jane Ye, Boyds; Ming-Hui Wei, Germantown; Valentina Di Francesco, Rockville; Ellen M. Beasley, Darnestown, all of MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/810,347

(22) Filed: Mar. 19, 2001

(51) Int. Cl.[7] .......................... C12N 9/16; C12N 15/00; C12N 1/20; C12N 5/00; C07H 21/04

(52) U.S. Cl. ................. 435/196; 435/320.1; 435/252.3; 435/325; 536/23.2

(58) Field of Search ...................... 536/23.2; 435/320.1, 435/325, 252.3, 196

(56) References Cited

PUBLICATIONS

Chetrite et al. (2000) J Steroid Biochem 72(1–2):23–27, Abstract.*

* cited by examiner

*Primary Examiner*—Rebecca E. Prouty
*Assistant Examiner*—David Steadman
(74) *Attorney, Agent, or Firm*—Celera Genomics; Justin Karjala

(57) ABSTRACT

The present invention provides amino acid sequences of peptides that are encoded by genes within the human genome, the enzyme peptides of the present invention. The present invention specifically provides isolated peptide and nucleic acid molecules, methods of identifying orthologs and paralogs of the enzyme peptides, and methods of identifying modulators of the enzyme peptides.

9 Claims, 24 Drawing Sheets

```
   1 TATTTCATTT TAGTCTCACC GTCTCCGTTT TTCTCTGACT GCCCAGAACT
  51 CCAGAAATCA GGAGACGGAG ACATTTTGTC AGTTTTGCAA CATTGGACCA
 101 AATACAATGA AGTATTCTTG CTGTGCTCTG GTTTTGGCTG TCCTGGGCAC
 151 AGAATTGCTG GGAAGCCTCT GTTCGACTGT CAGATCCCCG AGGTTCAGAG
 201 GACGGATACA GCAGGAACGA AAAAACATCC GACCCAACAT TATTCTTGTG
 251 CTTACCGATG ATCAAGATGT GGAGCTGGGG TCCCTGCAAG TCATGAACAA
 301 AACGAGAAAG ATTATGGAAC ATGGGGGGGC CACCTTCATC AATGCCTTTG
 351 TGACTACACC CATGTGCTGC CCGTCACGGT CCTCCATGCT CACCGGGAAG
 401 TATGTGCACA ATCACAATGT CTACACCAAC AACGAGAACT GCTCTTCCCC
 451 CTCGTGGCAG GCCATGCATG AGCCTCGGAC TTTTGCTGTA TATCTTAACA
 501 ACACTGGCTA CAGAACAGCC TTTTTTGGAA AATACCTCAA TGAATATAAT
 551 GGCAGCTACA TCCCCCCTGG GTGGCGAGAA TGGCTTGGAT TAATCAAGAA
 601 TTCTCGCTTC TATAATTACA CTGTTTGTCG CAATGGCATC AAAGAAAAGC
 651 ATGGATTTGA TTATGCAAAG GACTACTTCA CAGACTTAAT CACTAACGAG
 701 AGCATTAATT ACTTCAAAAT GTCTAAGAGA ATGTATCCCC ATAGGCCCGT
 751 TATGATGGTG ATCAGCCACG CTGCGCCCCA CGGCCCCGAG GACTCAGCCC
 801 CACAGTTTTC TAAACTGTAC CCCAATGCTT CCCAACACAT AACTCCTAGT
 851 TATAACTATG CACCAAATAT GGATAAACAC TGGATTATGC AGTACACAGG
 901 ACCAATGCTG CCCATCCACA TGGAATTTAC AAACATTCTA CAGCGCAAAA
 951 GGCTCCAGAC TTTGATGTCA GTGGATGATT CTGTGGAGAG GCTGTATAAC
1001 ATGCTCGTGG AGACGGGGGA GCTGGAGAAT ACTTACATCA TTTACACCGC
1051 CGACCATGGT TACCATATTG GGCAGTTTGG ACTGGTCAAG GGGAAATCCA
1101 TGCCATATGA CTTTGATATT CGTGTGCCTT TTTTTATTCG TGGTCCAAGT
1151 GTAGAACCAG GATCAATGTA CGTATTTCTC TGTTTGCAAC ATTCAACTGT
1201 CGTACCTCAA GTGTGTCTAA GATAATTCAA TTACCAGTCT CAGTATCTGG
1251 TTTCCTTTCA TCCAAAACAA AAAAGGATGT GTGTAGGCTG GTTAATTTCG
1301 AAGATGAAAA CCTTTTCCTC CCTGCCACAT CTTAAATTAG CTCAAGTATA
1351 CTACTTAAAG AGAAAGGAAA AATAAGTGTA TCAATGACTA ATTCTCTCAA
1401 ATTGACTGGA ATCTATGTCT TTTTGGTCTG TGTGCACAGA CAGGATGTGA
1451 TCTTCTGGGA TATCACCCTT CTTTGAATCA GAGATACGCT GTCATTTAAA
1501 AAAAAAACCT GACACCATCC TTTTAGTGTT TAACTTTTAA AAATTATTCC
1551 GAAAGAAATG TTTTTAAAAG ATAAATTTTG AAAAGCTGGC TTTTCTTTTA
1601 AAGGAAAAAG AGCTAAAGGA CTAGGCTGCT ATTTCTGTCA CTGTAGGCAG
1651 GTCACTGCTT CTCTTTGCAT CTCTATTTTC CCATCATGAA ATGGCCTTGC
1701 CTATTTTCCC ATCATAAAAT GGCCTTGTCA ATCATCTCAG GATGTTTTGA
1751 ATAAAATGGG ATTGCATCCA TGAAAGAAAA AAAAAAAAAA AAAAAAAA
```

FEATURES:

| | |
|---|---|
| 5'UTR: | 1-106 |
| Start Codon: | 107 |
| Stop Codon: | 1223 |
| 3'UTR: | 1226 |

Homologous proteins:

Top 10 BLAST Hits

| | Score | E |
|---|---|---|
| CRA\|335001101567410 /dataset=FastAlert /length=871 /altid=Derwe... | 752 | 0.0 |
| CRA\|335001100745208 /dataset=FastAlert /length=867 /altid=Derwe... | 624 | e-179 |
| CRA\|335001101589853 /dataset=FastAlert /length=818 /altid=Derwe... | 576 | e-165 |
| CRA\|1000682317641 /altid=gi\|5689491 /def=dbj\|BAA83029.1\| (AB029... | 647 | 0.0 |
| CRA\|89000000201760 /altid=gi\|7300128 /def=gb\|AAF55296.1\| (AE003... | 460 | e-128 |
| CRA\|18000005015326 /altid=gi\|7505633 /def=pir\|\|T16584 hypotheti... | 416 | e-115 |
| CRA\|46000019021936 /altid=gi\|6941989 /def=gb\|AAF32278.1\| (AF211... | 365 | 1e-99 |
| CRA\|1000682340827 /altid=gi\|6330840 /def=dbj\|BAA86561.1\| (AB033... | 328 | 9e-89 |
| CRA\|18000004928000 /altid=gi\|4504061 /def=ref\|NP_002067.1\| gluc... | 285 | 1e-75 |
| CRA\|18000004988847 /altid=gi\|1707906 /def=sp\|P50426\|GL6S_CAPHI ... | 279 | 6e-74 |

FIGURE 1A

BLAST dbEST hits:

| | Score | E |
|---|---|---|
| gi\|6471169 /dataset=dbest /taxon=9606 ... | 1035 | 0.0 |
| gi\|6500356 /dataset=dbest /taxon=9606 ... | 987 | 0.0 |
| gi\|7947681 /dataset=dbest /taxon=960... | 763 | 0.0 |
| gi\|11300906 /dataset=dbest /taxon=96... | 482 | e-133 |
| gi\|11300891 /dataset=dbest /taxon=96... | 446 | e-123 |
| gi\|11300907 /dataset=dbest /taxon=96... | 432 | e-119 |
| gi\|11300904 /dataset=dbest /taxon=96... | 418 | e-114 |
| gi\|6993185 /dataset=dbest /taxon=960... | 389 | e-105 |
| gi\|11300908 /dataset=dbest /taxon=96... | 367 | 4e-99 |

EXPRESSION INFORMATION FOR MODULATORY USE:
library source:
From BLAST dbEST hits:
gi|6471169 Pancreas adenocarcinoma
gi|6500356 Breast
gi|7947681 Colon
gi|11300906 Breast normal
gi|11300891 Breast normal
gi|11300907 Breast normal
gi|11300904 Breast normal
gi|6993185 Colon
gi|11300908 Breast normal From tissue screening panels:
Fetal whole brain

FIGURE 1B

Docket No.: CL001169
Serial No.: 09/810,347
Inventor: Jane YE et al.
Title: ISOLATED HUMAN ENZYME PROTEINS...

```
  1 MKYSCCALVL AVLGTELLGS LCSTVRSPRF RGRIQQERKN IRPNIILVLT
 51 DDQDVELGSL QVMNKTRKIM EHGGATFINA FVTTPMCCPS RSSMLTGKYV
101 HNHNVYTNNE NCSSPSWQAM HEPRTFAVYL NNTGYRTAFF GKYLNEYNGS
151 YIPPGWREWL GLIKNSRFYN YTVCRNGIKE KHGFDYAKDY FTDLITNESI
201 NYFKMSKRMY PHRPVMMVIS HAAPHGPEDS APQFSKLYPN ASQHITPSYN
251 YAPNMDKHWI MQYTGPMLPI HMEFTNILQR KRLQTLMSVD DSVERLYNML
301 VETGELENTY IIYTADHGYH IGQFGLVKGK SMPYDFDIRV PFFIRGPSVE
351 PGSMYVFLCL QHSTVVPQVC LR
```

FEATURES:
Functional domains and key regions:
[1] PDOC00001 PS00001 ASN_GLYCOSYLATION
N-glycosylation site Number of matches: 7
1 64-67 NKTR
2 111-114 NCSS
3 131-134 NNTG
4 148-151 NGSY
5 170-173 NYTV
6 197-200 NESI
7 240-243 NASQ

[2] PDOC00005 PS00005 PKC_PHOSPHO_SITE
Protein kinase C phosphorylation site

Number of matches: 5
1 24-26 TVR
2 27-29 SPR
3 66-68 TRK
4 96-98 TGK
5 206-208 SKR

[3] PDOC00006 PS00006 CK2_PHOSPHO_SITE
Casein kinase II phosphorylation site

Number of matches: 2
1 107-110 TNNE
2 288-291 SVDD

[4] PDOC00008 PS00008 MYRISTYL
N-myristoylation site

Number of matches: 3
1 19-24 GSLCST
2 161-166 GLIKNS
3 325-330 GLVKGK

[5] PDOC00117 PS00523 SULFATASE_1
Sulfatases signature 1

85-97 PMCCPSRSSMLTG

Membrane spanning structure and domains:

| Helix | Begin | End | Score | Certainty |
|---|---|---|---|---|
| 1 | 3 | 23 | 1.379 | Certain |

FIGURE 2A

```
     2    70     90   1.121  Certain
     3   351    371   1.012  Certain

BLAST Alignment to Top Hit:
>CRA|335001101567410 /dataset=FastAlert /length=871
           /altid=Derwent|WO200055629.35
        Length = 871

 Score =  752 bits (1921), Expect = 0.0
 Identities = 357/371 (96%), Positives = 359/371 (96%)
 Frame = +2

Query: 107  MKYSCCALVLAVLGTELLGSLCSTVRSPRFRGRIQQERKNIRPNIILVLTDDQDVELGSL 286
             MKYSCCALVLAVLGTELLGSLCSTVRSPRFRGRIQQERKNIRPNIILVLTDDQDVELGSL
Sbjct: 1    MKYSCCALVLAVLGTELLGSLCSTVRSPRFRGRIQQERKNIRPNIILVLTDDQDVELGSL 60

Query: 287  QVMNKTRKIMEHGGATFINAFVTTPMCCPSRSSMLTGKYVHNHNVYTNNENCSSPSWQAM 466
             QVMNKTRKIMEHGGATFINAFVTTPMCCPSRSSMLTGKYVHNHNVYTNNENCSSPSWQAM
Sbjct: 61   QVMNKTRKIMEHGGATFINAFVTTPMCCPSRSSMLTGKYVHNHNVYTNNENCSSPSWQAM 120

Query: 467  HEPRTFAVYLNNTGYRTAFFGKYLNEYNGSYIPPGWREWLGLIKNSRFYNYTVCRNGIKE 646
             HEPRTFAVYLNNTGYRTAFFGKYLNEYNGSYIPPGWREWLGLIKNSRFYNYTVCRNGIKE
Sbjct: 121  HEPRTFAVYLNNTGYRTAFFGKYLNEYNGSYIPPGWREWLGLIKNSRFYNYTVCRNGIKE 180

Query: 647  KHGFDYAKDYFTDLITNESINYFKMSKRMYPHRPVMMVISHAAPHGPEDSAPQFSKLYPN 826
             KHGFDYAKDYFTDLITNESINYFKMSKRMYPHRPVMMVISHAAPHGPEDSAPQFSKLYPN
Sbjct: 181  KHGFDYAKDYFTDLITNESINYFKMSKRMYPHRPVMMVISHAAPHGPEDSAPQFSKLYPN 240

Query: 827  ASQHITPSYNYAPNMDKHWIMQYTGPMLPIHMEFTNILQRKRLQTLMSVDDSVERLYNML 1006
             ASQHITPSYNYAPNMDKHWIMQYTGPMLPIHMEFTNILQRKRLQTLMSVDDSVERLYNML
Sbjct: 241  ASQHITPSYNYAPNMDKHWIMQYTGPMLPIHMEFTNILQRKRLQTLMSVDDSVERLYNML 300

Query: 1007 VETGELENTYIIYTADHGYHIGQFGLVKGKSMPYDFDIRVPFFIRGPSVEPGSMYVFLCL 1186
             VETGELENTYIIYTADHGYHIGQFGLVKGKSMPYDFDIRVPFFIRGPSVEPGS
Sbjct: 301  VETGELENTYIIYTADHGYHIGQFGLVKGKSMPYDFDIRVPFFIRGPSVEPGS------- 353

Query: 1187 QHSTVVPQVCL 1219
                 +VPQ+ L
Sbjct: 354  ----IVPQIVL 360

>CRA|1000682317641 /altid=gi|5689491 /def=dbj|BAA83029.1| (AB029000)
             KIAA1077 protein [Homo sapiens] /org=Homo sapiens
             /taxon=9606 /dataset=nraa /length=818
        Length = 818

 Score =  647 bits (1652), Expect = 0.0
 Identities = 304/318 (95%), Positives = 306/318 (95%)
 Frame = +2

Query: 266  DVELGSLQVMNKTRKIMEHGGATFINAFVTTPMCCPSRSSMLTGKYVHNHNVYTNNENCS 445
             DVELGSLQVMNKTRKIMEHGGATFINAFVTTPMCCPSRSSMLTGKYVHNHNVYTNNENCS
Sbjct: 1    DVELGSLQVMNKTRKIMEHGGATFINAFVTTPMCCPSRSSMLTGKYVHNHNVYTNNENCS 60

Query: 446  SPSWQAMHEPRTFAVYLNNTGYRTAFFGKYLNEYNGSYIPPGWREWLGLIKNSRFYNYTV 625
             SPSWQAMHEPRTFAVYLNNTGYRTAFFGKYLNEYNGSYIPPGWREWLGLIKNSRFYNYTV
Sbjct: 61   SPSWQAMHEPRTFAVYLNNTGYRTAFFGKYLNEYNGSYIPPGWREWLGLIKNSRFYNYTV 120
```

FIGURE 2B

```
Query: 626  CRNGIKEKHGFDYAKDYFTDLITNESINYFKMSKRMYPHRPVMMVISHAAPHGPEDSAPQ 805
            CRNGIKEKHGFDYAKDYFTDLITNESINYFKMSKRMYPHRPVMMVISHAAPHGPEDSAPQ
Sbjct: 121  CRNGIKEKHGFDYAKDYFTDLITNESINYFKMSKRMYPHRPVMMVISHAAPHGPEDSAPQ 180

Query: 806  FSKLYPNASQHITPSYNYAPNMDKHWIMQYTGPMLPIHMEFTNILQRKRLQTIMSVDDSV 985
            FSKLYPNASQHITPSYNYAPNMDKHWIMQYTGPMLPIHMEFTNILQRKRLQTIMSVDDSV
Sbjct: 181  FSKLYPNASQHITPSYNYAPNMDKHWIMQYTGPMLPIHMEFTNILQRKRLQTIMSVDDSV 240

Query: 986  ERLYNMLVETGELENTYIIYTADHGYHIGQFGLVKGKSMPYDFDIRVPFFIRGPSVEPGS 1165
            ERLYNMLVETGELENTYIIYTADHGYHIGQFGLVKGKSMPYDFDIRVPFFIRGPSVEPGS
Sbjct: 241  ERLYNMLVETGELENTYIIYTADHGYHIGQFGLVKGKSMPYDFDIRVPFFIRGPSVEPGS 300

Query: 1166 MYVFLCLQHSTVVPQVCL 1219
                       +VPQ+ L
Sbjct: 301  -----------IVPQIVL 307

>CRA|89000000201760 /altid=gi|7300128 /def=gb|AAF55296.1| (AE003712)
            Sulf1 gene product [Drosophila melanogaster]
            /org=Drosophila melanogaster /taxon=7227 /dataset=nraa
            /length=1114
          Length = 1114

 Score =  460 bits (1172), Expect = e-128
 Identities = 202/309 (65%), Positives = 252/309 (81%)
 Frame = +2

Query: 230  RPNIILVLTDDQDVELGSLQVMNKTRKIMEHGGATFINAFVTTPMCCPSRSSMLTGKYVH 409
            RPNIIL+LTDDQDVELGSL  M +T +++  GGA F +A+ TTPMCCP+RSS+LTG YVH
Sbjct: 53   RPNIILILTDDQDVELGSLNFMPRTLRLLRDGGAEFRHAYTTTPMCCPARSSLLTGMYVH 112

Query: 410  NHNVYTNNENCSSPSWQAMHEPRTFAVYLNNTGYRTAFFGKYLNEYNGSYIPPGWREWLG 589
            NH V+TNN+NCSSP WQA HE R++A YL+N GYRT +FGKYLN+YNGSYIPPGWREW G
Sbjct: 113  NHMVFTNNDNCSSPQWQATHETRSYATYLSNAGYRTGYFGKYLNKYNGSYIPPGWREWGG 172

Query: 590  LIKNSRFYNYTVCRNGIKEKHGFDYAKDYFTDLITNESINYFKMSKRMYPHRPVMMVISH 769
            LI NS++YNY++  NG K KHGFDYAKDY+ DLI N+SI + + SK+    +PV++ +S
Sbjct: 173  LIMNSKYYNYSINLNGQKIKHGFDYAKDYYPDLIANDSIAFLRSSKQQNQRKPVLLTMSF 232

Query: 770  AAPHGPEDSAPQFSKLYPNASQHITPSYNYAPNMDKHWIMQYTGPMLPIHMEFTNILQRK 949
             APHGPEDSAPQ+S L+ N + H TPSY++APN DK WI++ T PM P+H  FTN+L  K
Sbjct: 233  PAPHGPEDSAPQYSHLFFNVTTHHTPSYDHAPNPDKQWILRVTEPMQPVHKRFTNLLMTK 292

Query: 950  RLQTIMSVDDSVERLYNMLVETGELENTYIIYTADHGYHIGQFGLVKGKSMPYDFDIRVP 1129
            RLQTL SVD +VER+YN L E GEL+NTYI+YT+DHGYH+GQFGL+KGKS P++FD+RVP
Sbjct: 293  RLQTLQSVDVAVERVYNELKELGELDNTYIVYTSDHGYHLGQFGLIKGKSFPFEFDVRVP 352

Query: 1130 FFIRGPSVE 1156
            F IRGP ++
Sbjct: 353  FLIRGPGIQ 361
```

Genewise alignment of the protein sequence of gi5689491 against the genomic sequence of the present invention:

```
gi|5689491|dbj|     5 GSLQVMNKTRKIMEHGGATFINAFVTTPMCCPSRSSMLTGKYVHNHNVY
                        GSLQVMNKTRKIMEHGGATFINAFVTTPMCCPSRSSMLTGKYVHNHNVY
                        GSLQVMNKTRKIMEHGGATFINAFVTTPMCCPSRSSMLTGKYVHNHNVY
genomic         14101 gtccgaaaaaaaagcgggataagtgaacattctcttacagatgcacagt
                        gctattaacgattaaggccttacttccctggccgccttcgaataaaata
```

FIGURE 2C

```
                            gcgacgcagagtgatggcccctctgtacgccgagccgccggtgctctcc

gi|5689491|dbj|    54 TNNENCSSPSWQAMHEPRTFAVYLNNTGYRT
                      TNNENCSSPSWQAMHEPRTFAVYLNNTGYRT
                      TNNENCSSPSWQAMHEPRTFAVYLNNTGYRT
genomic         14248 aaagatttcttcgacgccatggtcaaagtaa
                      caaaagccccgactaacgctctataacgagc
                      cccgcctccgggcgtgtgtttattcctccaa

gi|5689491|dbj|    85                            FFGKYLNEYNGSYIPPGWREWLG
                                                 FFGKYLNEYNGSYIPPGWREWLG
                              A:A[gcc]           FFGKYLNEYNGSYIPPGWREWLG
genomic         14341 GGTAAGGG  Intron 1    CAGCCttgatcagtagataccgtcgtcg
                       <1-----[14342:24487]-1>  ttgaataaaaggatccgggagtg
                                                 ttaacctattccccctggaagta

gi|5689491|dbj|   109 LIKNSRFYNYTVCRNGIKEKHGFDYAK
                      LIKNSRFYNYTVCRNGIKEKHGFDYAK
                      LIKNSRFYNYTVCRNGIKEKHGFDYAK
genomic         24559 taaatcttatagtcagaagacgtgtgaGTAATTT  Intron 2
                      ttaacgtaaactggagtaaaagtaaca<0-----[24640:27102]
                      acgttccttctttctccaagtatttag

gi|5689491|dbj|   136    DYFTDLITNESINYFKMSKRMYPHRPVMMVISHAAPHGPEDSAPQF
                         DYFTDLITNESINYFKMSKRMYPHRPVMMVISHAAPHGPEDSAPQF
                         DYFTDLITNESINYFKMSKRMYPHRPVMMVISHAAPHGPEDSAPQF
genomic         27100 CAGgttagtaaagaaattaataaatccacgaagaacggccgcggtgcct
                      -0>aatcattcaagtaatatcagtacagctttttgacccagcaacccat
                         cccacactcgcttccagtgagtctgctgggccctgccccgcacagt

gi|5689491|dbj|   182 SKLYPNASQH                              TPSYNYAPNMDKH
                      SKLYPNASQH                              TPSYNYAPNMDKH
                      SKLYPNASQH          I:I[ata]            TPSYNYAPNMDKH
genomic         27241 tactcagtccATGTAAGTA  Intron 3    CAGAacatatgcaagac
                      catacaccaa  <2-----[27273:38735]-2> ccgaaaccataaa
                      tagccttcac                              ttttctaatgtac

gi|5689491|dbj|   206 WIMQYTGPMLPIHMEFTNILQRKRLQTIMSVDDSVER
                      WIMQYTGPMLPIHMEFTNILQRKRLQTIMSVDDSVER
                      WIMQYTGPMLPIHMEFTNILQRKRLQTIMSVDDSVER
genomic         38776 taactagcaccacagtaaacccaaccatatgggtgga
                      gttaacgcttctatatcattagagtacttctaactag
                      gtggcaaaggcccgatactagcagcgtggagtttggg

gi|5689491|dbj|   243                          LYNMLVETGELENTYIIYTADHGYHI
                                               LYNMLVETGELENTYIIYTADHGYHI
                                               LYNMLVETGELENTYIIYTADHGYHI
genomic         38887 GTAAGCA  Intron 4   CAGctaacggaggcgaataataggcgtca
                      <0-----[38887:39786]-0>taatttacgataacattaccaagaat
                                               gtcgcggggggggttcctccccttctt

gi|5689491|dbj|   269 GQFGLVKGKSMPYDFDIRVPFFIRGPSVEPGS
                      GQFGLVKGKSMPYDFDIRVPFFIRGPSVEPGS
                      GQFGLVKGKSMPYDFDIRVPFFIRGPSVEPGS
genomic         39865 gctgcgagatactgtgacgcttacgcaggcgt
                      gatgttagactcaatatgtctttggcgtacgc
                      ggtagcggacgatcttttgtttttttataaaaa
```

FIGURE 2D

```
gi|5689491|dbj|  301                         VPQIVLNIDLAPTILDIAGLDTP
                                             VPQIVLNIDLAPTILDIAGLDTP
                             I:I[ata]        VPQIVLNIDLAPTILDIAGLDTP
genomic        39961 ATGTACGTA  Intron 5   CAGAgccagcaagtgcaacgaggcgac
                       <2-----[39963:41324]-2> tcatttatatcccttatcgtacc
                                             cagctcctcgccgcgtttgccat

gi|5689491|dbj|  325 PDVDGKSVLKLLDPEKPGN                         FRTN
                     PDVDGKSVLKLLDPEKPGN                         FRTN
                     PDVDGKSVLKLLDPEKPGN          R:R[agg]       FRTN
genomic        41395 cggggatgcaccgcgacgaAGGTGTGTC  Intron 6    CAGGtcaa
                     catagacttattacaacga  <2-----[41454:41732]-2> tgca
                     ttgccgtccatgcaagatc                         taac

gi|5689491|dbj|  349 KKAKIWRDTFLVERG
                     KKAKIWRDTFLVERG
                     KKAKIWRDTFLVERG
genomic        41746 aagaatcgatcggag
                     aacatggactttagg
                     ggcatgttacagaag
```

Genewise alignment of the encoded protein sequence of the present invention against the genomic sequence of the present invention:

```
cdna_pep           1 MKYSCCALVLAVLGTELLGSLCSTVRSPRFRGRIQQERKNIRPNIILVL
                     MKYSCCALVLAVLGTELLGSLCSTVRSPRFRGRIQQERKNIRPNIILVL
                     MKYSCCALVLAVLGTELLGSLCSTVRSPRFRGRIQQERKNIRPNIILVL
genomic         2106 aattttgcgtggcgagtcgacttagatcatagcaccgcaaaccaaacgc
                     taacggctttcttgcattggtgcctgccgtgggtaaagaatgcattttt
                     ggttcttgtgtcgcaaggacctgtcacggcaagaggaaaccacctttgt

cdna_pep          50 TDDQDVEL                             SLQVMNKTRKIMEHG
                     TDDQDVEL                             SLQVMNKTRKIMEHG
                     TDDQDVEL          G:G[ggg]           SLQVMNKTRKIMEHG
genomic         2253 aggcgggcGGTGAGAC  Intron 1    CAGGGtccgaaaaaaaagcg
                     caaaatat <1-----[2278 :14101]-1>   ctattaacgattaag
                     cttatggg                             cgacgcagagtgatg

cdna_pep          74 GATFINAFVTTPMCCPSRSSMLTGKYVHNHNVYTNNENCSSPSWQAMHE
                     GATFINAFVTTPMCCPSRSSMLTGKYVHNHNVYTNNENCSSPSWQAMHE
                     GATFINAFVTTPMCCPSRSSMLTGKYVHNHNVYTNNENCSSPSWQAMHE
genomic        14149 ggataagtgaacattctcttacagatgcacagtaaagatttcttcgacg
                     gccttacttccctggccgccttcgaataaaatacaaaagccccgactaa
                     gcccctctgtacgccgagccgccggtgctctcccccgcctccgggcgtg

cdna_pep         123 PRTFAVYLNNTGYRT                            FFGKYLNE
                     PRTFAVYLNNTGYRT                            FFGKYLNE
                     PRTFAVYLNNTGYRT          A:A[gcc]          FFGKYLNE
genomic        14296 ccatggtcaaagtaaGGTAAGGG  Intron 2    CAGCCttgatcag
                     cgctctataacgagc <1-----[14342:24487]-1>    ttgaataa
                     tgtttattcctccaa                            ttaaccta

cdna_pep         147 YNGSYIPPGWREWLGLIKNSRFYNYTVCRNGIKEKHGFDYAK
                     YNGSYIPPGWREWLGLIKNSRFYNYTVCRNGIKEKHGFDYAK
                     YNGSYIPPGWREWLGLIKNSRFYNYTVCRNGIKEKHGFDYAK
genomic        24514 tagataccgtcgtcgtaaatcttatagtcagaagacgtgtga
```

FIGURE 2E

```
                      aaggatccgggagtgttaacgtaaactggagtaaaagtaaca
                      ttccccctggaagtaacgttccttctttctccaagtatttag

cdna_pep       189                              DYFTDLITNESINYFKMSKRMYPHRP
                                                DYFTDLITNESINYFKMSKRMYPHRP
                                                DYFTDLITNESINYFKMSKRMYPHRP
genomic      24640 GTAATTT  Intron 3   CAGgttagtaaagaaattaataaatccac
                   <0-----[24640:27102]-0>aatcattcaagtaatatcagtacagc
                                                cccacactcgcttccagtgagtctgc

cdna_pep       215 VMMVISHAAPHGPEDSAPQFSKLYPNASQH
                   VMMVISHAAPHGPEDSAPQFSKLYPNASQH
                   VMMVISHAAPHGPEDSAPQFSKLYPNASQH
genomic      27181 gaagaacggccgcggtgccttactcagtcc
                   ttttgacccagcaacccatcatacaccaa
                   tgggccctgccccgcacagttagccttcac

cdna_pep       245                                TPSYNYAPNMDKHWIMQYTGPML
                                                  TPSYNYAPNMDKHWIMQYTGPML
                             I:I[ata]             TPSYNYAPNMDKHWIMQYTGPML
genomic      27271 ATGTAAGTA  Intron 4   CAGAacatatgcaagactaactagcac
                     <2-----[27273:38735]-2> ccgaaaccataaagttaacgctt
                                                  ttttctaatgtacgtggcaaagg

cdna_pep       269 PIHMEFTNILQRKRLQTIMSVDDSVER
                   PIHMEFTNILQRKRLQTIMSVDDSVER
                   PIHMEFTNILQRKRLQTIMSVDDSVER
genomic      38806 cacagtaaacccaaccatatgggtggaGTAAGCA  Intron 5
                   ctatatcattagagtacttctaactag<0-----[38887:39786]
                   cccgatactagcagcgtggagtttggg

cdna_pep       296   LYNMLVETGELENTYIIYTADHGYHIGQFGLVKGKSMPYDFDIRVP
                     LYNMLVETGELENTYIIYTADHGYHIGQFGLVKGKSMPYDFDIRVP
                     LYNMLVETGELENTYIIYTADHGYHIGQFGLVKGKSMPYDFDIRVP
genomic      39784 CAGctaacggaggcgaataataggcgtcagctgcgagatactgtgacgc
                   -0>taatttacgataacattaccaagaatgatgttagactcaatatgtc
                     gtcgcggggggggttcctccccttcttggtagcggacgatcttttgt

cdna_pep       342 FFIRGPSVEPGSMYVFLCLQHSTVVPQVCLR
                   FFIRGPSVEPGSMYVFLCLQHSTVVPQVCLR
                   FFIRGPSVEPGSMYVFLCLQHSTVVPQVCLR
genomic      39925 ttacgcaggcgtatgtcttcctaggccgtca
                   tttggcgtacgctatttgtaaccttcatgtg
                   tttttataaaaagcatctgatatcatagtaa
```

Hmmer search results (Pfam):

| Model | Description | Score | E-value | N |
|---|---|---|---|---|
| PF00884 | Sulfatase | 234.1 | 2e-66 | 1 |

Parsed for domains:

| Model | Domain | seq-f | seq-t | | hmm-f | hmm-t | | score | E-value |
|---|---|---|---|---|---|---|---|---|---|
| PF00884 | 1/1 | 43 | 355 | .. | 1 | 409 | [. | 234.1 | 2e-66 |

FIGURE 2F

```
   1 GTATCAGGTT TCTCACGATT TAAAACAAAT GCACAGAAAC CAAACAGTCA
  51 GTGCAGAATA ATTGCAGGCT TTCAGTGTTC AGCATGTACA GCAATCACTG
 101 TGGAATCACC CTGCGTTATT AAGAAGAAAG CACCAAATCT TACATTAGTG
 151 ACTTCTACAG GGCTGCGTTA TCAATTGGAG CTGTCTTGTT TGTTGCAGAT
 201 AATGTAGTCA GGACTGCCTG GCTGCAGACA CTAGAGTTTT GTTTAAAAAC
 251 CGATTTCTTC TTGTCTCTTT CTCTCTCTTG CAGTATAATT ACAGGCTGCA
 301 GAGTGAAAAG CATTAGAACT GTTTACAAAA CAGCTCATAA AGTTTAAAAT
 351 AATGGGGATA CGTGTGTGTG TTTGTGTAAA ACAAAATAAT GTGTATGGTA
 401 GGGGTAAACA ATATCCAGTC TTTCTTCTTT CACTACCCCC TGTCACCTTC
 451 CAGAATTAAG GGCATGAAGT TGAGAGATGG AGCCCTTTCC TCCTGCTATG
 501 CGATGCTTAC ACTTAATTAG TTATGCCTAC TTATCCAATG CCAGTTTATT
 551 GTTGCAGATC AAAATACAGA TTCTCAGGTG TATGGGGACT GAGTGGCTGA
 601 TGAAACAGAC TGCTATCTAA TTAATTTTAG GGCAGCCTAA ATTCCCATAA
 651 AGATGTTCCC TCATGACATA TGAGAGGAAG ATTTTATTTT TTTAATGAGC
 701 CCTTTGCTAT CTTTCCAAGA GAAAAGCTTT CAGCAGGTTA GTGTTCCAAA
 751 GTGAGAGGGG CATTTTTCCA ACCCTTTCAA AAGCCTCCTT CTGTGCAGCT
 801 TTGCAAAGAT TTTGCAGCTC GCCCTTCTGG ATTTTATTTA TTTATTTTTT
 851 AATGCGGAAG GGTAGCCGCT GACTCCAGCC TCGGGGCCAA TCAATCATTT
 901 TGCTTTGCAG GTTTAAGATC TGTGACAAAG CGAAACCCCT GTGCTATCTG
 951 TGCCTTACCA GTCTCACCAA CAATAAGCCT GGTGACTGAC AATCGAGAGG
1001 GGGCTCTGTC CACGTAGGTG CCGGCACAAG CTGAGGACAT GAGTGGGACA
1051 GAGGAACCAG CCTTGCACGG AGGAAGCACC TTTTCCTTCT GGTGATTGAT
1101 TGATGGGGGA CAGTGAGGAG GTTTTCAGAG ACTGGAAAAA ATTGTCCCAG
1151 TCACTTACTA TGAAGTCTTT GTCAGCAGAA AAGACTCTCC GGGGTAGAGA
1201 ATGATATAAT GCAGATGACA AATGACAGGT GTGTGTTTCG TTCTGCTTGC
1251 TAGGTACTCA GTATCACACG CAGGTGAGTC AGCGCTCCCC AACATGCCCC
1301 TTGCGCCATC TGCTCCCCAC ATGCAAACAC TCGTTCCCAA CGCTCTGTGG
1351 TTTCCCTGGC ACTGCTGGCT CTTCCTAATC GATCGTCAGC TCTGTTGGGG
1401 ATGTGTAAAG TACTGTCAGA GTGTGAGCAG GGTGATACCT TACCACCCTT
1451 TTATGGAGCT GATTATGAAA TGAAGATAGC ATTTGAATCA TTTGTTAGCA
1501 GTTCTGAAAG TTGTTTCCTT CTGTTCCTCC CTTTTGGAGC ACAGAAGAAA
1551 AAATATATGT AATATATACA CATATAATAT GCTGTTGCAA GAGACTACTT
1601 CAGATCGAAA ATCTGTTTTT AAAATCATTG ACTGATATTT CCTTTGTATT
1651 TTTTTCTCCC CCTTCCAGGA CCCTATCTGC AGATGTTCTG AATACCTCTG
1701 AGAATAGAGA TTGATTATTC AACCAGGATA CCTAATTCAA GGTATTAGCT
1751 CTCGTCAGAA AGCTTTTACA TTTGAGCTCT GTGTTGGAAA TTCTATTTTG
1801 GCAATGAATT GAAATAGGAA AAGTTGGAAT GAGAATAAAG GACAAAAGTG
1851 AATTTGCAAA ATAATCAAGT GCTTAAAAAA CTACCCAGCA CTTGTGAGGG
1901 TTTGCTATTT CTGACTCATG TGCAACCCTG TCTCTGCCAG CTTATGTGCC
1951 AATACTGACT TATTTGTAGC CCTTTCTCTG CAACTGTGCT TGGAGTTTGG
2001 ATTTCATTTT AGTCTCACCG TCTCCGTTTT TCTCTGACTG CCCAGAACTC
2051 CAGAAATCAG GAGACGGAGA CATTTTGTCA GTTTTGCAAC ATTGGACCAA
2101 ATACAATGAA GTATTCTTGC TGTGCTCTGG TTTTGGCTGT CCTGGGCACA
2151 GAATTGCTGG GAAGCCTCTG TTCGACTGTC AGATCCCCGA GGTTCAGAGG
2201 ACGGATACAG CAGGAACGAA AAAACATCCG ACCCAACATT ATTCTTGTGC
2251 TTACCGATGA TCAAGATGTG GAGCTGGGTG AGACACTGGA CTCTTCACTT
2301 GTTAGTCTCT TTTGTTCAGA TGATTTCTCG AGTCTCAGGA TTATCAGGAG
2351 ACATTCTGAG GCTTTGCACT TAATTATTGC ACATTAACCA ACACCCTAGT
2401 TTACGCAATG AACTTGTATT GACCATAAGG CATTTGGTTT GTGTTTCAGC
2451 ATTACTTTTC TGATGTTATG CTTTTGAAAT GGTCGGGGAA GGGGCCTGGG
2501 GGAGTAGGAC AATGGAGAAA GAGGGTCAGC ACTGAAGACT GTAGAAGGAA
2551 AGGATTGAAA GCCCTCAGTT AAGACATTGT AAAAATATTT GGGCAAAGTT
2601 GTTTCAAAGA GTATGAGGAT GTGACTGTAA TTTTATGCAA TGGATATGAA
2651 TATAGACTGA TACTAAAGGA ACTTTCAGTG GTTATTAGTA TTAGAGTGGA
2701 TTACTTATTC ACAGTTTGTT ATAGTAATTG TTAGGTAATT CAAAGTTGCA
2751 GTGTTCTATA TGTCTTTTGG TAGAGAATCC ACTTACTACT ACCTTAGATA
2801 TGATGCTTTT TTATTTAGCT TGCCTAGGCT AAGCGTAGAG CACCCAGAAA
```

FIGURE 3A

```
2851 GCCTGCCAAA ATCTAGTGAT TCTAACTTAC CTTCTATATC ACCTGACTGG
2901 GTTTCTTACC TTCTCACCGT CTTCAATGGC CCAGCCCTAC AGTCTTGTTC
2951 ATAAGCCAAG GGCCAATTCT TCTAGTCCAC CTAGTGCAAG GCAGATAGAA
3001 AGCTTGCCCC TAGAAGTTGT CACTACCACT CCTCATTTCT TTTCCTGAAC
3051 CCAAATTCCT TGCTCTCAGG CATCACCCAG CTGTGCTTAG CCATCACATT
3101 CAACCTGACT GGTAGTTGAA TCTTCTAGCA GAGCATGCTG GGCTTCTTTA
3151 CCGAGCTCCT GAGGCTCAGG TTCTTGAGGA TAAAACTCTT CACGCTGGCA
3201 CTTGGTCTCC ATGGAAGGGG ACTTTGCTTT CCCACTTGAA ACCAGACGGT
3251 GAGATCCCAG TAAAGTTAAT TCCTTGGGTT CAGCTGGAAG CAAATGCGCT
3301 AAAAAGCCAG CAGATGTCAT TATTGCTGAC GTTGGTTTGA GGAGTCAACC
3351 CAACTTTTTT TTTTTTTTAA CAAGGGTATT GATTTTCAGG CGACAGGCCA
3401 AAATGAAAGG TGTCACACAT ACATGAGTGT GTATTTAGCA CATATGATGT
3451 TAGTATGTAT GTAAGTGGTG GTTTAAATGT TTTCATTCAC TTACAGAGCA
3501 AGTAATTTTA GCTTTTTTAG AGCCTTGTGG GTCCATTTCA AGTTAGTTTA
3551 GTGCCTAATG TGTTAATAGC ACAGTCTCTG CATGAGGATT GCAATGTTAA
3601 ACATATCCTT GCCCTCTGCT TGACCTCACA CCTGAACTCA CCTTCCTTAA
3651 TATCTCACCC ATCCATCGCT TTTGCTACAG CTGAGATCTC TGGATCCTCT
3701 CATCTTTCCC AGTTTTTCCC TCACCGGTTT GTCACCTGGC CTGCCTGCCT
3751 CCTCTAGTCT TGGCCTCTCT TGCCCACCCT TCACTCAATT GCCAGAGTTA
3801 TCTTTCAAGT ATCTCTCTGA TCAGATCACT TTTCTGCTTA AGTCCCTTCT
3851 GTGGTTTCCC TTTGCCATGA GATTATGCCC TTCTCCTCTG TGGGCAAATG
3901 AGTTCTGAGC CTTGCGACCC CTGCCTGTCC CCAAGGCTGT TTCCCTTTCC
3951 TCCACTTTCA CTCTGTGCTT CATAAACACA ATTGCCATCT CCCCAAAGGT
4001 GTCTGGTGGC TTCACCCCCC TCGCCTCTAT CCATGCCTTT GCACATCTCA
4051 TCCCCTCTGC CTTTTCCTCT TTCCCCACCT GGAGAAACCC TACCTGTTCT
4101 TCATAACCCA GTTCATGTCA TGCGCTTGGT GTTCCCAAAA CAAAACCACC
4151 CTCCCCTCCA GCAGCATTGA TGGAACTTTC CTTTGCACCC CGAGAACACG
4201 ACTCCAGCAT GGTGCTCATT CCACCATAGC CTTCCATGCC TGTCCCTTCC
4251 ACTTGACCAA GATCAACCAG AGAGCAAGGG TGTGTTTTAT GTTGCACTCC
4301 TCATGCACTC CTAGTGCCTG GGAATATAGT GGGCACTAAA CTAACTTGAA
4351 ATGGACCCAT AAGGCTCTAA ACAAGCTAAA ATTCCCAGAA ATAAATATAA
4401 GTATTCATCA TCATCTACCT CTTCAATATA CAGCACTGTC TTTAAAATAT
4451 ATTAAGAAAT TGCTCATAAC TTTCTTTTTT AACAGAATTC AAATTTTCAG
4501 CCTTGTCCTA TAGTTCATTT ATTCATCCAG TAAATATTTT CTGAGCAGTT
4551 ACCAAGTATT GCCTTCTGTT GGAGGCATGT GACTATCATG GTGAAGGGTT
4601 ATAGACCAGG CTCAGCCAAC CCAGATATTT CCTACATATT TGCCTTTAAC
4651 TCCTTCCTTG ATTTTCTAGC CAGATAACAT GCTAAGAACT AGCTCATTGG
4701 CTGGGTGTGG TCATTCTCGC CTATAATCCC AGCACTTCGG GAGGCTGAGG
4751 CAGGCGGATC ACCTGAGGTC AGGAGTTCAA GACCAGCCTG GCCAACATAG
4801 TGAAACCCCG TCTGTACTAA CAGTACAAAA ATTAGCCAGG CATGGTGGCA
4851 GGCACCTGTA ATCCCAGCTA CTCTGGAGGC TGAGGCAGGA GAATTGCTTG
4901 ACCCGTGAGG CAGAGGTTGC AGTGAGCCGA GATCACACCA TTGCACTCCA
4951 GCCTGGGCTA CAGAGCGAGA CTCCATTTCA AAACAAAAAA AGAACTAGCT
5001 TGTTTAACTC TCACAGTAAC TCTAGGAAGT AGTTACTATT CTCTCTTTAA
5051 TTTAGGTATG AGAAAAATGA GGCTCAGAGA AGTCATGTAG CTTGTGGTGA
5101 GCAAGTAAAT TGTGAAACCC AGACCTGTAT TAGATCTGAG TCTCCACAGC
5151 TACGTATTTA ACCACTGTCC CTTCCATTAA TCAGCCATCT ACAAATAATT
5201 ATTAAGCACC TCCTAAAAAC AATCGGCAAA TTCATAATAT TTTAGGTTCT
5251 GGGAGAGAGG GAACAGAAGC AAAAGATAGG CCACTGGCAA AAACAAAATG
5301 ACTAGGAACC ACAGTGAACT GTGGGTTGGA GGTCCAGAAA AGACCTCCTT
5351 TCTTGGCAGA AAAGTCATGC TCTCGGTAGT GGTTCCCGCT TGATGGAGAC
5401 TTTTCCTCAT TTTTCTGTAA TGTGCTCATA ATCCTTCTAG AACATTATTG
5451 CTCTAGATTT TGGGTGTTGG TTGTTTTGTT TTTGTTTTTT TACCATCTTA
5501 ACCATTTTTA AGTGTACAAT TCAGTACTGT TAAGTACATT TACATTGGTG
5551 TGTAACCCAT CTCCAGAACT CTTTCCATCT TACAAAAGTA AAACCCTATA
5601 CCCATTAAAC AGCAACTCCC GTTTCTCTCT CCCTCAATCC TGGCAACTAT
5651 CATTCTACTT TCTGTCTCTG TGGATTTGAC TACTCTAGGT ATCTTATATG
```

FIGURE 3B

```
5701 GGTGAAATCA TACAGCATTT ATCTTTTTAT GACTGGCTTA TTTTACTTAC
5751 CCTCATGTCC TCAAGGCTCA TCCATGTTGT AACATGTGTC AGAGTGTCCT
5801 TCCTTTTTAA TGCTGAATAA CTTTTCATTG CATATATGTA CCACATTTTT
5851 TTAACCCATT CATCCACTGT TGGAAATTTG AGTTGCTTCC TCCTTTTCCC
5901 TATTGTGGAT AATGCTGCTG TGAACATGGG TGTACAAAGA GCTCTTCGAG
5951 ACCTTGCTTT TAGTTATTTT GGAGCTATAC CCAGAAGTGG AATTGCTGGA
6001 TCATATGATA CTCTTATTTT TATTATTTTG AGGAACCACC TTACTGTTCT
6051 CCATAGCAAC TCACCTTGTT ACGTTCCCTC CAACTGAGCA CAAGTGTCAT
6101 AATTTTTCCA CATCCATGCC CACACTTGTT ATTTTCTGGT TTTGTTTTTA
6151 ATAGTAGCCA TCCTAATGGG CATGAAGTGT TATCTCATTG TCACTTTGAT
6201 ATGGTTAGGT TTTGTTTTGT TTTTTACTCC AGTGCAATTT TCTTTGCCAA
6251 GTGCTTTAAT AAATCTTCAC CTAATGCAAA CCTTTTTGCA CCTGTAATGC
6301 TGTAGGCAAT TTTGGCTACT GTGCCTCCAA AAAGAAAGTA ACAGACTTAG
6351 TAAAGACTTA GAAGAACAAT TATGAAAATT CTAATAGAAT ACTTTTCTCA
6401 CTGGGAAAGC ATAAAACAAT CCTATCTGTT TATCTAGAAA GATGAAGGCT
6451 GAGAAGGGCT ATAATCAAAG TTTATAAAAT CGAGCCAGGG AGGAAAGTAC
6501 TAGTTCATTA TGAGCAGGAG CCCTTCCCTT CACTTTCAGG ACAAATAAAC
6551 TATTACTCTG TAAAGGGAGT AAGACACATA AGGAATTCAT TAATAAAAGT
6601 ACTAGAACCT TGCATATGGA TAACACTTTA TCTTTTCCCA AAGAACATTT
6651 TGTTCACATT ATTGTGAATG AATATTGCCA TCTCACATGA GTTGGGTGGG
6701 TAGGACAAAG ATCATCATCC CAGGAGGAAA CAGCCTGTGG AAAGATGAAA
6751 TGGCTTAACC ATGGTCCCCT TACTTCTGAA TTTGCTTTTC CCACAACTTA
6801 AGAAGTTGTT CACGTTGTGC CTATACCCGT AAGTACTTCA GAGTTTTAGG
6851 CTAGAATAAT GGGTGGAAGA TTTACAATTT TTTAAGCTAA GTAAACACGC
6901 AAGGAAGTGA TCAACATAAA GTTCAGGATA ATGGCTACCA CTGGGGAAAA
6951 AGTGATGACC GAGAGCATCA GTACATTCAC ATTCTATTTC AAAACTGAAA
7001 AAATATATAT CTGAAAGAAT ATAATCATGT TAAGTTTTGT TAAAGCTAGG
7051 AGATGCGTTA TTTATTCTGT TACACCCTAC ACTTGAAATA TTTTATAAAT
7101 CAGAAGGAAG AAAATAAAAA ATGTTTGAGG GACTCCTAAC TTTCTGAGCC
7151 TAGCATCAAA GAAATTGGGC TCTAAATCTT TCCCAAATGG CCTTTGGTGC
7201 TAGTCTGAGA AACAAAATAC TGAGCAGAAT AGACCATTGA TCTGACTCAA
7251 CATGGCATTT CTTACATTCC TAGGAAATTG ACCTGACAGG AACATCTCAG
7301 TAACATTGAC CCGATGTTTC TCTTAGATCA TATGTATAGG GAAGCTATGA
7351 GTACATGGAG ATATTTTGTT TCTTTAAAAC AAAAGCCAGA ACACAAGATA
7401 TTCAGACCAG AGCTAGCCCA CAGATGTATG TTGTTTGATG AGCATACTTT
7451 TCAGAATTAA GCCAATATTT TAAAATCATA TTTTAAAATA TATATAACAT
7501 ATAAAAAAAT CAGATTCTGA CGTTTCTTGA AAATTCAAAA AATGAAGGCT
7551 TGTATTCCCA TGAAGCAGTC ATCACTTGGA TGTTTGAAGG GGAGCTGCAG
7601 CTGCTCTCGG ACACTGGGGA TCCCCCACTA CTGTGTTGTC CCTCAATAAC
7651 TTATGCCAAG GTGCAGGTGC CATTTATCAT TGACCATACT GCTGTTTTTC
7701 TTATAGTCAG GAAAAGCTCT ATAAACCATG TCTCTATCAA AGGTAAAACA
7751 ACAAAAAGAC ACAAAAAACCC TCTGACTTTT CTTATACCTG GCTGCCTTCA
7801 CTTGCCTACC TTATCTATGT AGCCCTGTAG GCATGTTAAC TTCCATTCCT
7851 GTAAGTAGCT TTTAATGGCC TTGTGCTCTT TTGGAGGGGC CAGGAGGAAA
7901 TGATGAGTCT TAGTGATCTG GAAACATTCC AGACTAATTT ATTATCTTCT
7951 CTTTTTTCCC TTCTTCTCCC AACTACCTTT TCCCCCTTTG GTTTTAGGTA
8001 AAAAACATCT TTTTTTTTTT CTTGCCAATT CCATAGTTTG GGTAGAAAAA
8051 AAATACCATT TAATTTTGTT ATTTTTTATA TGCTTATGCT TTTAGAATTA
8101 GAATATTCAA TAGATCATAC AGGCATTTTA ATAAAGGAAA TGTCACTGTT
8151 TCATGTTTCA TACTTTACTA TGAAAATAAC TGTTGGCATG TGAAAATGGC
8201 AGGGAAGTAC CTAATACAAA CGACTTAAAT ATTTAAAGCA TTAGCCTTAC
8251 TTCATCATAA AAGAATGACA TCGACAAACA CCCCTCCACA ATCAGTAAGA
8301 GCTGGGTTTG CTTGTTGTTG TCAATCTTCA AACCATGAAT GCTCTAATCC
8351 ACATGGAAGT ATCTCTCTAG GAAGCCAGGT GTATATGAAT CCCACATGTC
8401 TGGGATTTCC ATAAGTGATA ATGACAATAT TTACTGTTGA ATTTCTGGTT
8451 CTGCGAGTTT TTCTGGACAT GACAAACAGG TTTGATGAAA TTTTTAATGT
8501 TTAGTAATAC AAAATACTGT ATACTCAAAT GCTAAGATAT ATGTATCGGG
```

FIGURE 3C

```
 8551 AAAGGTAAAG CTTTGTTTTG AAGTTTAAAC ATGTCAATGA AGTAATTCAG
 8601 GATCTCCGTG TGATTTTAGC AAAGTCATCC AAATTAGGGG GACATTTTCT
 8651 CCGATCCTTT TTCATACAAA TGATTTTTGT ATGAAATCAT TCTGTATGAA
 8701 ATGATTTTGG GAATCAAGTA GTTGGAGTAT ATAAAGTGAT TTAAATTCCT
 8751 CACTATGGTT CTGTCTAGCC ACAACCTATC ACATACTCCA TCCAAAGCAC
 8801 TATTCCTGGA GCTTTGATTT TTAACTGTGC CAAAATTGCC AACATGGTGG
 8851 ATCTTGATGG ATTCCTGAAG GGTGGCACTT CTCCCACTCC CAGCCACCGC
 8901 TGACCTCTTC AGCATCCTGG TCCACAGCCG ATGGCTGTCA CAGCATCCGC
 8951 CTGCAGGAGC AATGGAAGAT GTTCTCAGTC CCAGCCTGGA ACTGGGGCAC
 9001 TGGGACAGTG TGTCTTGGCA GTCCTGTGGC CTGGACCTTC CCTCTCATCA
 9051 AGCCAGCCCA GTCAGCAGTG CATGCACACC AGCTACACAG ACATAATCAC
 9101 GGTTGCTTCA GAGCATTTGT GTCTGGCTCC CACTTCATGG GACAACTTAA
 9151 AATAACAATG AAGTTGGGCT TTTTGCTTAG GGTGAGGAGT CAGTGTGTGT
 9201 AGAAAAGGGA AGAATTGATA TTTGTATTTG AAAACCAATA TCAACATTTT
 9251 AAGTCTTACA GCATAGAAAA GGTAGTTGAC CTCTGTTCTC TCCTCCAGCT
 9301 TTTGGACTTC AGATGTAGAT TACAGAGAAG AAGATGGAAG AGGCAGGAGA
 9351 AAATTTAATG TGATGGGGTT GAGGTGAGCA CATAGGGCAA CCACAGCCAC
 9401 CTCGGCACAC TCCTTACAGG AAGTACTTGA TGGCATCCTG CCGTTTGCTC
 9451 AGCAACAACC TTGTAAACTA GTCGGAGTGG GGAGCGCTAT TAGAAGCTCC
 9501 ATTTTACAGA TGAGAAACAC AAACCAAAAA AGGATAAATG ACTTGCTCAG
 9551 GCTAAGCTGT GGCAAAATCC AAATGTTTTC CCACATGTTC AAGTCTAGGG
 9601 CTCTTTCCCT TCTCATCTTT ATCATCCTCA CCCCTGCCTT GTGAATCTGA
 9651 TTATGAGTGT TCAGCTTTAC AATTCATATC ATTCCTATGA AATAATTGTT
 9701 GTAATAACTG AGAATCAGCA CCGTTTGCAT TTCAGGCACC CAAGGCCTGA
 9751 AACCTACAGA AGTGAAGAGC TTCAGCTTAA AACAAAACTG AGCCCTTCCA
 9801 CTTATCGGAC AGACATTGTC CTGTCCACTG CTCTCAACAG CTGTGAATAA
 9851 ATAACTATGA GTTTTATTAC AGAATCATTT TTAGTAAGGT TTGCCAATAA
 9901 AAAAATCAAT GGCACAATCA CAGTGGGAAT ATATACAGGG TAAGGCAGTG
 9951 TTATTGACTG ACATTAATCA TTGCACAGCC ATTAAAAGGT GCTCGATGCT
10001 TTCCTTACTG GTACACACTA ACACAGTGGA GTGAAGAGAT TCAGATTCCT
10051 GCACACCGTC ATCTGTCTCT ACCCAGAGAA TCCATAGAGA TCAGAGGCAA
10101 CAATTAACGC CACCATGGCA GTCAGCAGCT AAAGACAGAC AGATCCACAG
10151 CCCACTCATG CCTCATCTGT GCCTGAGCCA CTGAGACCAT TTCAGCCTTG
10201 AGGGGAGGGT AGGAGACAGG TGTTAATGTC AGTCAGTATC TCCTCTAAGA
10251 GGCGAGAAGA ATCAAAAGAT GAGAGTGCAG AAAGAGAGAC CTATCGCGAC
10301 TGCAAGCAGA CGTCAATTCT GTTTCTCATC TTGAAAATGT CAATGTCACA
10351 GCCAGCATTC AGCCTAGATA GAGCTCAAGA GCATGGTCTC TGGGAAGACT
10401 GCCTGCATTT ACTTCTGGGT TCTGCTACTG AGGGTCTGTG TGGCCCTAGG
10451 CACAGCATGA TTTAGCCTTC TGCACCTCCA TTTCATTATC TGTGATATAG
10501 GAATAATAGC TGCTAGCACC CACCACAAAG GATTATTGTC TGGATCAAAT
10551 TAATTGCTCA TGTGAAGCAC TTAGAAGAGA ACCTGGCTGA GAGTAAGTAG
10601 AAAATCGATG TTTCTTTTTC CTGTCTACAA TATACCTTAT AGTCTTGGCA
10651 GTGATCTAAG CCACCTAGAT CACTCAAAAT TAGGCACCCA CTACAGTCTC
10701 TTCCAGCTCT AGGCTTCCCT GATTCTGTGT CCAACCTAGA ATACTTTTTC
10751 AGGTGAGATT CACTGAGAGG CAGCTTCGGC TTCACCCAGG TTTCATTAGA
10801 AACACAAATT CTCAGGCCCC ATCCTGGACT TACTAAGCCA GTATCTTGGG
10851 GTGGGTACAG GATTCTAGGG CTTATTATGC CCTTCAGGTG ATTTTTTAAA
10901 GTTGGACAAG CATTGTCTCA GAATCTCTTT ACTGAGAACC TTCAAGCCAG
10951 ATTCCCACTT TTTGTTTTGT TTTTATGAGA CAGAGTCTCG CTTTGTCCCC
11001 CAGGCTGAAG TGCAGTGGCG CGATCTTGGC TCACTGCAAC CTCTGCCTCC
11051 TGGGTTCAAG CAATTCTCCT GCCTCAGCCT CCCAAGTAGC TGGGTCTACA
11101 GGCGCATGCC ATCATGCTGG CTAAGTTTTG TATTTTCAGT AGGGACAGGG
11151 TTTTACCATG TCGGCCAGAC TGGTCTTGAA TTCCCCGCCT CAGGTGATTT
11201 GCCCACCTTG GCCTCCCAAA GTGCCGGGAT TACAGGCATG AGCCACTGAG
11251 CCCGGCCCGA GATTCGCATT TTCAAGGACC CCAGTGGTGG AGCTGTATTC
11301 TTAACAGTGC CTATGGGGAT CCACTGTTGT CTTGGTTCCT TTTGACGTGT
11351 GGACTGGTGG GAGCCAGGGC ATCTGGAGGG ATTGCTTGGG AGCCCTACAC
```

FIGURE 3D

```
11401 AATCAGCTCA GTTAGTTAAG AAAAGGATGA TACTGAGAAT GAGAGGAGAA
11451 TCCTAGCTGG GGCACTTCCA GCAGTGATGA ATTGGGATAA GTTTTAGCCC
11501 CTGTTTTTAT ATTATTTTGA CTTTAAATCA GATTTCTACC TCGGTCCCAT
11551 ATTTGTAGTC TAAATGAGTC TGTAAACTAG AGATTACAGT GCTGCGATTC
11601 AGAACCTTGG ATGATGGCCT CAGCTGCATT TTTCTTTTAT TTGAATTCTG
11651 CTAAGGCTCA TAAAGGAAAC TGGGAGCTTG TTCTTTGAAA TAGACTACTG
11701 GACACTGAAA AGCCATCAAC AGGGTTTGCT GTTTTCCCCA AAATCAAGAT
11751 ACTCAGTAAC TAACTACTGC AGAGATCTAA AGAGGAGCAA TGAGACATGG
11801 TAGAAATCTT CAGTGTCACC TTTCACCCTC TTTCCACTTC TACATCTCCG
11851 TTCATCCACT TATCTCCAGG ATATTCCCCC TGTGTGATCA ACCAACACAA
11901 ATATAAAATG CAACATTTCT AAAATGGGGT TTTAAAATCT CCCATAAGGC
11951 ATATTCCTTT TTAGTTACTT CTTCACCATC AGTGAAACGA TTGGTTTCCA
12001 GTTTTCTTCT CACGGTGAAA ACTTCAAGGT GTTAGCCAAC TCCCAGCCTT
12051 CTCATGCATC ACCACATCAC TTGGGTCTGC TTCTTAGGGT CGCTCTGTGT
12101 CAGAGGCATA GTCGTCCGAG TTCTTCTTTC CTCAGGGGTA GACGGCTTCA
12151 GCGACCTCAT CTGCACCCTT CGTGGACCAG CAGCAGTGTG CCCTCCTCAA
12201 TCCACACACC ACCATTGCAA CTGCAACGCC TCTCGAGGGG ATTGCAATCC
12251 ACTGCAGCAG CAACACCTTA CAAAGACTTT TTTCTTAACA TGCCGTTCGT
12301 GTCTTTGACA CAGAACATAA CTCTACCTTT GTTTTTTTTA TTCTATCACA
12351 TCCAGTATCT CTGCCCAGCC TTCAAGCTAT TTGCTAAATC TGCTTTCCAC
12401 ATTTCATGAA GAGAATTCTC CATATTTCTC TTCATGCCAG GAAATCAATG
12451 TGTTGTTCTC ATCACTCTAC TTGTTTCTTC CCACCTCCAG AGCATCACAC
12501 ATGTCACTCG CTGCAATCCC CCAATGATAT ACTTCACCCA TCCGACATTT
12551 ACTTCCTCCT TTTTTTCCAT CTGTCCTCAT CTCTCATTTC AGAACTCTTA
12601 TTAAGCCATC AATCCAAGTT CCCTCTATTT TTATATGCCC TGCTACTGCT
12651 GTATTCACAT TGTTACGTGT GCATTGCTTT GCAAATATCC CCAAGTGATT
12701 TTTCTATGTA GGTTCTCCTC TAGAGAATTT ATTACTGAAG ACCAGAGGCA
12751 GAAAATTTCC CATTTCTTTT GTTTATGCTA CACTTGGGAG ATCAGCCCGG
12801 AATGCTGAGG TTGATAGAAT GTTTTGCATG AAGTAGGCAC TCAAGACATG
12851 TTATTCATTG ACTACAAAAG GTTGCTTGAT GCCCTGAAGA CAACCAGAAG
12901 AGAAAGAGCA GTTAGGATTG CTCCTAGCCG AGGCATATTT TAGGGAGCTC
12951 TAATGAGACC CAATTAGAAA CCCTCCTCCT GTTCTCATAT GCGTCATGTG
13001 GAACGGTAAA AGCTAGTATA TGAAGACACG GGGCTAACTG TGGCTTTTTG
13051 GACTGTTGCA TGCTTCTCTT CTGCCCTGAA TGCTTGCCTG GTTTGCATTA
13101 CGATTTCCTT CCTTGCTGGA AAACATAGAC TTTCTTCCTT TCTTTGGAAG
13151 AAGTGGGACC TGTTGGAAAT CTGAGGCTCC AAGATTCAAA TGCAATGGGC
13201 TTGGCTGTAG TGCTCTGTAG TACACTTCTT GACAAGTCCT GAAAAGACTA
13251 TTGAATTCTG GCCTGTGCTT TTCTGCAGTG TTTGGATGTG TTTCAGCTGC
13301 AGTGTTTGGC TGGACAGAGT AATCGAAATA GTTTTTTTTT TTTTTTCCTT
13351 CCTCAGCAAT CTTACGTTAC CAGTTGATCC TTAAAGTTAA AATGGAATAT
13401 TTTACAACCC TGCAAATACT TTCGAGTGCA ATCGAATTAT AGCTCTTTCA
13451 CAAGCAAACA GCCTATCTTT AAAAAATTGT GCATAAATAG GTCAAAATAT
13501 AAATTGATGT TGTTATCCTA ATAGAAAAAC TGGCAAACAT TTGGTGAGCT
13551 TGCTAGAGGA TACCAACTTG CATTGAAGAT CTTTTTTAAT TATTATTAAA
13601 CAAACACAGG CATTTTGATG GGACTTAATA TGGAAGAAAT TTTTTTCTCT
13651 TTTCTTTCAT ACGATTAAAA TGCTATAGTA GTAATCTACA CTAGTAATCT
13701 AGTAGCAATG TCACTAGTAG ATTGCATTTG TGCTGGGCTG GGGGTTTTGA
13751 TGCTCTGTGT ATCAGGCTAT TGTTCTCTGG TAATCTTCAA AGGGCTGCTG
13801 GCCTTTGAAT CTGCTCCATA TCTAAAATTC TAGCTTTAAT TATCAGATTA
13851 GCCTGCATTT TTTTTTCTTC GTGATTACAG GGAGGAGAAG TGTATGTTTA
13901 TTATTCTGCA AAATACTTGA GATGGTAGGA TCTCAAATGC TTAATTTTGT
13951 TGTAGAAATG AGAGCTGATC AAATTATAGA CTCCTTTAAG CTAAGGAAAG
14001 GAAATGAATA AGTCAGGGAA ACAGAGGCAC TGAGGGGCAC AATCGAAATA
14051 GGCATTCATG TGCTGCACTT TGCTAAACAA TGCTGGCACT GTGCCTTTCA
14101 GGGTCCCTGC AAGTCATGAA CAAAACGAGA AAGATTATGG AACATGGGGG
14151 GGCCACCTTC ATCAATGCCT TTGTGACTAC ACCCATGTGC TGCCCGTCAC
14201 GGTCCTCCAT GCTCACCGGG AAGTATGTGC ACAATCACAA TGTCTACACC
```

FIGURE 3E

```
14251 AACAACGAGA ACTGCTCTTC CCCCTCGTGG CAGGCCATGC ATGAGCCTCG
14301 GACTTTTGCT GTATATCTTA ACAACACTGG CTACAGAACA GGTAAGGGAT
14351 GACGTTTCTA GCCCATGAAC GTCTTGTAAT ATGTCTTAGA CTCAGGAAGA
14401 AGTGTCATGT AATGAAATGC ATGAAGTTCC AACAAATACC TAAAAAAGGA
14451 TCAAGTGTTT TTAAACTGCT TGACATCTAC CCCAGGGTCT GGGACACAGT
14501 AAATGATCAA AATTATTTAT TATTTATTAA TTAATGAAAA ACTGATGGGT
14551 AAATCAATCA TGTGTACCTT GTTGATTCAT GTATTTGTTC ATTCATAATT
14601 AATAGGATTT GGAAAGTTTC TTTAGCTTGT GGTTGTTTTT AGGTCTCAAA
14651 TGTTCACTTC TACCTTCCAG GAAAGGAAGT CATCCTAATT GCTACACCTC
14701 CTATTATTGT TTAACCTACA CAGGGCAAGA AGAGGTTTTT GATTAATTGG
14751 TTTTTTGAAA ATTGGGGACT TCTTTCAAGA GGGGTAGTGA ACATCATGCC
14801 AGTCTTTCTG AGAAAAAAGC AAGGTTCCTT CTGGTAATAT TAGCCCCAAG
14851 GCCCTATCCT CCCAGCATGT AGATGATGTC CTTGGGTTTT TTGTAGCATT
14901 TCTTCATAAA AGGGCACAAC GTTGTTCGTA GAAGGGCTAC AGTGCAGACA
14951 TGGGTTGTTG CTTGTTTTTA TTTTTCCAGA ATCACCTAGG CTTATTCATA
15001 AGAATCAAAT ATGTTATGAT TAAAGCTTGT TCAAATGACT TTCAGGCCTA
15051 CAATTTCTCT ATTTTGAAGA TTTAAAAGTA AAGGAGTTCA GATAAATATT
15101 CTCCTGCATC TCTTTTAAAA GTGAAATTAA TCTTTCCCAC TGGACTCAGG
15151 AAATATATGG CCATTTGCTT CTTTGCAGAG CGCCCTACGG GCACTTAATA
15201 CTTGTTATTT ATGGATGAAA ATATTGATTG TGCATATGAT AGCACTGTCA
15251 CTCGCAGACA GCTCAAAGTC TCGACTCGAA GCAGCTCCTC CCGTGCATCT
15301 CAAGGGTGTT TTCTTATGCG TAGGAAAGAA ACTAGGTTAC GTAGAGGTTA
15351 CAGAGAGTGC CTTATCTGAG TGTGTTTTCT CACATTAGTG ATTTAAATTT
15401 ATAGCACCTT TCATTTGAGG ACTCTAAAGC AATTTGCAAA TCCACCAAAC
15451 ATCCCTGTAG AGTTCATAGA TGGCAAATGT ACTTGGCTCT GTTTTATAAC
15501 TGAGGTGGGG ATTTCAAATA TTGCGTGACC AGCTCAGAAA CAGAATCAGA
15551 GGCGGTTCCC TAATAACCGG TTCCTGATTT TAACCATCAA ATTGTGTTTT
15601 GCTTCTGGGA AGTGTTGTGT GAAATCAGTG CCTTTCACCT CCCAGGTTCC
15651 CTAGTAGCAA ACATGGAACT GGAACGATTG GGACTCTCAC ATATCCAGAG
15701 TGAAATGGAT GACATTTGTC ATAAGAAATA GAGATTGAGG GTGAGACAGG
15751 GCCCTGCCAG GACTTAGAGC AGTCAACTAG GGTTTGCTAA TTTGTTTCAG
15801 GGCTAAATTA GGAAGGGCAA GAAAGAAGGG AACTCCATTT TGCCATTATC
15851 TCACCTAATT CCTAGGGCAA TCTTGAAAGA AAGGAATTTC CCATGTTACT
15901 AATGAAAAAA CCGAGACTCA GAAAGGCTAA TTGTCTATGG TCATGAGCTA
15951 GTCGGTGATG GAATGAACCC AGCACATCTG ACTCCAAAGT CTTTCCTCTG
16001 TTCATTGTCT TATTTATTTA TGTAATGATT CTCTTCTGCC TCATTCCAAA
16051 ACGCCTTCCA GAGATACAGA CTTTAGAAGC TACAGACCCA TGAGGACCCT
16101 GGCAAACAGA AACAAAGAGT AGGACTAGCT AAAGTCAAGG CAAAGATTGC
16151 TGTACAAACT GCTTGCTGTG GAGTTGTAGG GAAAGGTGGA ATATTTAGAA
16201 CTAAGCATCC AGATGTTAAG AGCAAAAATG GAAACACCAT CCATTGTAAA
16251 GTTCACCCAG TCACCGGGAT AAAAACAATT CAGTTGCCTC TAAGCATGTT
16301 TCCTGGTACT TGCTTCGGTT ATACTGTGCT ATATCCACCT TAAGAGGGAT
16351 TGAGAGAGTT TAACTAAAAC TCAAAGATGA TTTAGTTCCA TTTCCTTATT
16401 TTTAGAGGAG CAAATTTACA CCCACAAGAA TAAAGTGACT GAAGTGACAG
16451 ATCTGACTGT TTTTTATTTA TTTGTTTATT TATTTTATTT TATTATTATT
16501 ATACTTTAAG TTTTAGGGTA CATGTGCACA ATGTGCAGGT TAGTTACATA
16551 TGTATACATG TGCCGTGCTG GTGTGCTGCA CCCATTAACT CGTCATTTAG
16601 CATAAGGTAT ATCTCCTAAT GCTATCCCTC CCCCCTCCCC CCACCCCACA
16651 ACTGACTGAC GTTCCAATGG GAAGAGCCGG CACCGGGACC TTAGTCTTCA
16701 GGGCTCTCTC CAGTGTGCTG ATCAAACCTT AAGAATCGGG TCTGGGATGA
16751 AACTGTGTAC ACACCGGAAG GCTTCCCTGT TACCTCAATG GACTGTCACT
16801 TTTTTGTGCA GCCCGAGAAG TTTGTTTCAG TCGATGTCTT CTCCAGGGAG
16851 AGTAGATTTG CTCCTGGAAA CTAAATCTGT TTCTAAACCT TTTCCCCAGG
16901 GTTTAGACAC TTAGGTAATA ATACAATTTA TAGTGAGTCA ACCTCCAAAA
16951 TAAAAGGAAT TCTTTAAGGG AAATAAAGAC TTTTCCAAAA ACTTAGTTAA
17001 CAGTAGGAAA AGGGGCTGGG TGCGGTGGCT CACGCCTGTA ATCCCAGCAC
17051 TTTAGGAGGA CAAGGCTGGC GGATCACGAG GTCAGGAGAT CGAGACCATC
```

FIGURE 3F

```
17101 CTGGCTATCA CGGTGAAACT GTCTCTACTA AAAATAGAAA AAATTAGCCA
17151 GGCGTGGTGG CGGACGCCTG TAGTCCCAGC TACTTGGGAG GCTGAGGCAG
17201 GAGAATGGCG TGTACCTGGG AGGCGGAGCT TCCAGTGAGC CAAGATCGTG
17251 CCACTGCACT CCAGTCTGGG AGACAAAGCG AGACTCTGTC TCAAAAAAAA
17301 AAAAAAAAAA AAGGAAAGAA AAACCAGTAG GAAAAGGATA ATATGGGCTC
17351 AGGAAAACAA ATCTAGATTT GCCTATTAGT AAATCAGAAA AAATAAAAAT
17401 TGGGGCCGGG TGCAGTGGCT CATACCTGTA ATCCCAGCAC TTTGGGAGGC
17451 TGAGATGGGC GTATCACCTG AGGTCAGGAG TTCGAGCCTG GCCAAAATAG
17501 CAAAACCCCA TCTCTACTGA AAATACAGAA ATTAGCCAGG TGTGTTGGTG
17551 CATGCTTGTA ATCCCAGCTA CTCAGGAGGC TGAGGCAGGA GAATCACTTG
17601 AACCAAGGAG GCAGAGGTTG CAGTGAGCCA AGATCGCACC ATTGCACTCC
17651 AGCCTGGGCA ACAAAGCAAG ACTCTGTCAC ACACACACAC ACACACAAAA
17701 AAAAAAAAAA ATGGGAAGAC TGAAATGGCA GTGATAGAGA TCTCTATAAT
17751 TTAATTTATC CTTGATGGGA AAACATTACA GTATCTCAGA CAATTAGGAA
17801 GTAAAAATGT CTTCATGACA ATAGTTATTG ATCCAACCAT GGACAACAAC
17851 CCATTTGAAA ATACACAAAT AAGTACACAC AAGTGGCAGG AATCTTAGAA
17901 AATTAAGAGA ATTGGTAGGT AGATATTAAA CCAATGTAAT TATGAGACAC
17951 TAAACTAGTA GGGAGAAAGT CAATGTGTAA AGATTCTATT GCTTTCCTAA
18001 TAATGAATTT ATTATTTGGA ACATTTAGCT ACAAACCTAA GAAAAATAAT
18051 GACGGAAACT GAAATATGTA CTATACATAC ATAAATATCC ATCTAGAGAG
18101 TAAGTTTTAT GTAGAATAAC TCAGAGAAAA CAAATTACTA AAGGGCTTAT
18151 TTTGGGAGGC GTCCAGAATC CATGGATTTA AATGAGTTGA ATTAATCCAA
18201 TATTATATTT ACCATTGTAT GACATGAGTT TTCTCTTTCA GAACTGAGGC
18251 ATATTTTTGG ACTGGCTATA GCCTAAATTT TTCTAAGTTT ACTCATGGAA
18301 AATATGAGTC TATGAGAGCT TGAATGTTCA AGAAGGGGAA AATGCAGTAA
18351 CATGTCGACT GCACTTCATA TTCTGACAAG TGAAATAGGA ATGAGATTGG
18401 ATTATATATC ATAAAAATGA TTATCCTGCC TGAAATCAGC TCCAAAAAAA
18451 TTAACTTAAA TTTATTATGA GGATATCAAC ATTAATATAA AACCTGGCTT
18501 AGGTTTTAAG GTAAAAATAA TTATCCATGG TTGAGTGATA GCATTAAGTA
18551 TTTAACAACA ACAAAAAAAA CTGAAGCAAG ATTGAAAACA TCGTGGAATC
18601 ACATTCTACC TTGATTTGTT TTGAGGACTT GGACTGGCCA GTTTTCCAAT
18651 CTGTATGATG CAGAGATTGG CCTAGAATGA TTCCTAAGTT TTCTTTCTTG
18701 TCCAAAGTTA CAGTGTGTTA TAACTTTATT ATACTCATGG TAATTATAAT
18751 ATTGATTCAT TTAACAATTG TGGTATTTGA ATTATAATCC TAACACATGG
18801 TACATAAAAT CACATATGAG TTAAATCTTA ATCACATGAA TTCTACCTCA
18851 CATCACTGAG GTAGAAGGGA CAATATTTAA TAGACAGCTG CAATAAATAT
18901 TTTTGTGAAG AATTCTTTTG TCATAAATCA AAATCATAGA CCTTAGTTCT
18951 GAAAAAGAAA AATTATATCA AATAATGGTA AATACAATAT TGGATCAAAA
19001 ATTTTTTTGT CTTTTTACGT TACAAAATTT ATGTTACTTA TAGCAAGTAT
19051 ATTTATTCTC TAATATGAGA TTTTTTAAAT GTAGAGTTCA CTTAAAGTAA
19101 GACAAACTAA TATTCTTAAT TTTATTATGA TGTAGATTCT TGATACATGC
19151 ATAAACATGA GAAATGTCAT ACATTTATTA AACCACAGTG TGCTTGGAAC
19201 ACACTAGACA TTGGGATGAA GACATTTAAA GGAAGATTCC TGTCTTCACT
19251 AGACTTACAA TCTAGTTGAG GAAACCAGAC TGCTGTATAC AAACTGACAT
19301 TAATCATAAT TTTAACTTGG TTCAAAATTA TTTATATTTA TAGTTACTAG
19351 CGTGAAATCC ATCACCCTAA GTCTATCAAT TACGTGGATT AAAATCTCAA
19401 TATATCTTTT GATACATTAA ATAAGATTTG ACTTTTCTGC GGCATCAGAT
19451 CTTTGGGTTA GTCACTATTG CTGGCTTTAA AAGAAATTCC TTGGCTTCAG
19501 GTAGTTCCTG GAAATTTTTC TAAGCATTAT GGAACAGGTT GTCCTAGACA
19551 GAAGTAGCAT GGCCTGAAGC CAACAATAAT TACAATCAGG TCTTCTGATC
19601 TTTCTCCCTG CCCCCCAACC CCCACCACCT TCTTAAACAG CTGTGAAGGG
19651 AAGTGCTTAA TGGTATCCAA AACAAAGAGG ATGGGTAAAT GGCACATTAG
19701 TGATGTATTC AGATAGTAGG AGTTGAATTG AATTGCCAAT GCCGAAGGAT
19751 AGAAAAATAT TGAACTATAC GTAACCTACA TGTAGACATA ATGGCAGTAA
19801 GGGCAAGAAA GCTAAATTCA CCTTAGGAAG GGAAAAAGAG ATTTAATACA
19851 TCTGGAGGAA AATAATTAGA AGGCCAGATA ATCAATTGCA GAGCGCCGCC
19901 AGGAAACATC GTGTTGAAAG AGGCCGGGGT GATTACAAAC GAGTCTCAAT
```

FIGURE 3G

```
19951 GTCATGAGGC AACAAAAAGG CCAGAGCAAC TGGAGGCCAA CAGTGCTGCA
20001 CCCTGACACC CAAGGCCCCC ATCAGCCTTG GAATGAGTGT GATGGGTGAG
20051 CGCACATCTG GAATACTGAG TACATTTCTT ACGCTCCGTT AACACAGAGA
20101 CACCAAAAAC CTGGAGGGAG TTCTGAAGCA AATAACAAGG ACTATTAAAA
20151 GACTTGAAGG AATAGTTTAT AAGGGAAGGA TTAAGTCAAA GGGGAATGCC
20201 ATGGCAATGG GTAGAAAACA GTACAAAATA TCCTACAAAG TAAAACAATG
20251 AGGAAAGGGC AGGAATGACT TGGGGAGAGG AAACAAAAAA ACCCCAACAA
20301 TGAAGTAACT TAAAAGTGCA GAAAAAAAAA TTAAAACTAA TTAAGCAGAA
20351 AAATGTAAGC CAAATGGAGG AGTTTGTTGC CACAAAATAA GTAGTAGTGG
20401 GGAAGAAAAT ATGTAACCTC CGAAGAGATA TTTTCAAGTG CACAAGTGCA
20451 GAACTCTAGT GCGAGATTTC CTTACACTGC AGGATGGAAA ATCATTTACA
20501 AAAGACAGGG CCAAAAGAAT ACTGCTAATG GTGATGCTAA TAACAATATT
20551 AGTTGTAGGA GCACTTAACA AGCCGTTGTT TTGTGCCAGG CACTGTTTTC
20601 AGCGCTTTAC ATATGTGTTG ATGCATTTAA TCCTCAAAAC AATCCTGCCA
20651 CCATTATTAT TATCACCATA GTGGCTTTGC AGAAGGGGAG TTGGGGGAGG
20701 GAGAAGTGAA GTAACTTGCA TGTAGATGGA TACCCTAGCA AGTAGCAGAG
20751 CCAGAATTTG AACCCAAGCA GGCTGGCTCT AGGGTTTATA TTCTCAATCA
20801 CTATGCTTTT TGCCTTCTTG GAAAAAAAAA AAAAAAAGGA AAGAAAAGTG
20851 GGATAAACCC GTAGGGATGA GGAGGAGGCC AAGGAAAGCA CGGGGCTTGA
20901 GGCTGTTAAG TGCAAGCTTT TTGGAAACAA TCGCTTTTGA ACGTTAGTGG
20951 GGTGTGGCCT TGGTCTGCTG CCTGTGGCTC CAAGTCATAC TGCATTTTGT
21001 TGGAAAAGGA AAATCATCTT GTGGTTCTAT GTGAAAAGGT CAGTTCGTCT
21051 CTAAGACAGG AATTCCTCAT TAAAAGAATT CCAACTACAC GTAGTCAGCA
21101 CAGAAGGAAA TCCTGAGTCA CCTGATGTGA GACCCTTTGA CACTTTGCCC
21151 TACACTGATC AACGTGCTCA GTGCCCCTGG CAGAATGCTT AAGCAGCGGG
21201 CACTTGGCTG ACTGTAGACC TAATTGGTTC ACTCATTCAC AGAGCCAACA
21251 AATAAACATT CATTCAACAA ACAAACATTG CCATGTTTCT CAGACTGGAG
21301 TCTAGATTCT TTTAAAAATA ATATAATAAG AAATAACAAT TTTAGAAACT
21351 CTAAAGCTCT ATTCTATGAA AATGTTTTGA AGGCCAAATC AGCTTTAAAA
21401 AATATGATGA TTTGATTGGG CGCAGCGCCT CATGCCTGTA ATCCCAGCAC
21451 TTTGGGAGGC CTAGGCAGAT GGATCGATCA CCTGAGGTCA GGAGTTCGAG
21501 ACCAACCTGA CCAATATGGT GAAACCCCAT CTCTATTTAA AAAAAAAAAA
21551 AAAAATTAGC CAGGTGTGGT GGCGTGTGCC TGTAGTCCCA GCTACTTGGG
21601 AGTCTGAGAC AGGAGAATCG CTTGAACCCA AGAGGCAGAG GTTGCAGTGA
21651 GCCGAGATCA CACCACTGTA CTCTAGCCTG GGCAACAGGG TAAGACTCCA
21701 TCTCAAAAAA ATAAAAAAGA TAATTCAAGC AAAATCACAA AATTTTTAAA
21751 GTCTAGACCT CGTAAAGTCC CCAGAATACA TTGGATTCAT GAACCCAAAT
21801 TCAAGAAACA AAAAGGATGG AGCCCTGAAC TGTGTGCAAG GATGGAGAGT
21851 GCCTCAGAGA TAAGGCAGAG GCAATGTTTG CCCTCAAAAA GCTTACAGTC
21901 TAGCAGGTGT TCAGCTTCTA TATGAACATG ACTATACCAC AATGGAGAAA
21951 GGGAAGATGA CATTACAACC ACAAAGACAG TGTTGTGGAA TTAAGACAGA
22001 GACTGTGAGT GAAATGGCAT CTGCTCTGGC CTTGATATAT AAAGAGGCAA
22051 ATAAAGAGAA TTGCACAAGC AAAAATAGAG AGGTGGGAAC CAGAGAGCAA
22101 ATAGAGGAAA CATTAGCTGG AGAGAGGGAC GATTAACAGA GAAATAGGAG
22151 ATGGGGTTGG AAAGGGAAGG ATTTTGTCCA AACTCAAAGT AGGCCTCTGA
22201 GGGCAAGCTA GCAGAGTACA CTTGATTCTG CAGGCAATGA GGGTAATCTG
22251 AGATTGCGAG AAGAGGGTGA AGTAACCAGA GCAGGTCCTT GGGAAGATTA
22301 ACCAGTGGCA ATCGAAGTGG AAAGACCCTC CATCCTGGCT GGGAAAGTCA
22351 GTGAGACCAT GAGCATCTGT GAGGGGTGGC AAGTTACCAG GGATGGCAGG
22401 AGGGATTTGA GCACTATTTC CAAGGCAGAC CTGATAGGAG GTGGCAACTG
22451 CCCAGCAAGG GGAGCGCAGG AGCAGGCGAA AGCAGAGGGG GCTCTGGAGG
22501 GCCAAGCATG GTTCATGGAG GGTGATTATG CCATTCAGAG GAATGGAGTA
22551 AGGCTGAAAG GGAAAACTGG TAATTCCATT TTAGGCAATG GCATTAGGAA
22601 GCAAGTAAAA CATTCAGATG GAGGAATTCT ACAGGTACAG GTGCTCCTTG
22651 ACTTACGATG GGGTGACATC CCAATAAACC CATCATAAGT TGAAAATAAG
22701 GTAAGTCAAA AATGCATTTA ATATACTGAA CCTACCGAAC ACCAGAGCTT
22751 AGCTTAGCCC AGTCTAACTT AAATGTGCTC AGAACACTTA TATTAGCCTA
```

FIGURE 3H

```
22801 CAGTTGGGCA AAATCATCGA ACACAAAGCC AATAGGCTTG TAATAAAGTA
22851 CTGAATAACT CATAGGATTG ATTGAGTACT GCACTGAATG CATACCAATT
22901 TTACACCACT GTAAATGTGA AAATCTTCAA TTGAACCATC GTAGGTCAGG
22951 GACCATCTGT AGTCGTATAT CAAAGATAAA AGCAAGCTAA ATACCTATCC
23001 CATAGAGACA TCAAAATTAT GTACATCATT AAGTTTAAAA TTCAGAATGT
23051 GTGTTTTAAG ACCAATGTCA ATAAAGTGCT GCAATTCTAG AATTCGTTTC
23101 TATTATCCCA AGCCAGTCTT CCAGGAACTA CTTTTTTACC ATGGATATAA
23151 GCGAGGGCAC CTATAAAATC TGTTTAATGA AGCCAGGCAT TGGCTTTGAC
23201 ATGGAAGGCG TCTGGCAACA GCTTTATAAC ATCAGAAAAA CTAAAACTTG
23251 CCTACATATG TATATGCATG CATAGGGGTG TGTGTGTGTG TGTGTACACA
23301 CACATATATA CATACACGCA CACATGCTTA TACCTATACA GACATATATA
23351 AAATAAAGTT TTCTCTAGCC CTTTCTACTT GAAGGGAAAG CTATGTGTGT
23401 GGCTGGAGTG ACTAAACATT TAGGTTTACC CAGAATCATG CTTGTTTATA
23451 CCTGCTTTTC TGTAATTACA GCAATTACAA ATAACATCCT CTTGCTCTCT
23501 CAAAAGTATT CCAGTATATT TATGACTACC ATTCTGCTAG GTTGTAATGT
23551 CTTTTTCACT TCAAGAATGA ACCCATATTG TTCCTGGAAT CCCAGCTTCT
23601 TCTTTGCTTC CCGTACCCCT CTCCTGTCAT CATCTTTTGC AGAAGACCAA
23651 ATTTCTAGTC ACCCTCTCAG AGAGACCGAG TCAGCCCTGT GGCACAGTGG
23701 TCTTTCTTGG AAGTGACATG CCAAAGTTAT AAATGTGAAG GCCTTCCAGT
23751 GGCTTTTTTA GTGAACTGTG GTGTCTTTGT GACACATACA CTTCTACTAT
23801 ACTATAATTG TATGAAAATT AGTAATCTAT GTAGTAACTC TATGTTGACA
23851 GAATTTTTAT TATCGATAAT AGATGTATAC ATTCATAAAA TACACATAAC
23901 ATAAACACCC ATTACATACT ATACATGTGA TATAAACCCT GACCATATCC
23951 CATAAAAATG GAGTTTACCA TGGTTCCCTG GTTTGGAAAA TTTGTACTCT
24001 CTGGATATGT AAAAACGAAA ATAAGCTTTT CAATAGTGTT TTTATAATTC
24051 ACAATTCTCA AATAGTAAGT TAGAAAACTT ATCACAAAGA CTGAACTTTC
24101 AGTTCTCCAA CACCTGCCCG GTGGTTGCAT TCCAAATCTC ACGCTACTTC
24151 TCTGATTGTT CCATCAACTT AACAAAAGAG CATAGCCTGA TTTTACTCCA
24201 GTAGGACCAT AAGAAATGAA TGCACCCAGA GTGCTGTGAT CATTATGATG
24251 GTTTCATTGA GCTGTAATCC ATGTACTTGG ATACTACTTC TATTTATTTT
24301 TTAAAAATGT GTTTGTGTCA CTTTGCCAAA GGATTGGAGT ATTACACTAA
24351 TGTCATTTTG GCATTCACTA TTACCTAGGG CAACTTTTGT TTTACCGTCT
24401 CTTTTTCAAG TCATAATTTT ATACTTATCC ATTTATTTAT GATTAATCAT
24451 TTTACGTGAA AAAAATAATT CTTTTTTCCC ACTGCAGCCT TTTTTGGAAA
24501 ATACCTCAAT GAATATAATG GCAGCTACAT CCCCCCTGGG TGGCGAGAAT
24551 GGCTTGGATT AATCAAGAAT TCTCGCTTCT ATAATTACAC TGTTTGTCGC
24601 AATGGCATCA AAGAAAAGCA TGGATTTGAT TATGCAAAGG TAATTTTCAG
24651 GCACTTTTAC ACTGCATCAA TTTACTTTGT GCATAATGGG GAAAAGCCAT
24701 TTTCAGTGAG TTAAACTATC CACAAGATTG GCTTTCTATG TTCTCACAAT
24751 GTTAGCATGA GAAATGTTAA GGTAATTTTA AACTCTAGGC AAGGAAAAGA
24801 CTCTCAAGGA ACGCTGCCTT TGTGTAGTGA TTTCCCTCAT TAGGATGAAA
24851 GGCAATCAGG CTTTGATGAA AGTATCATCA AGAAAATCAG AATTCTCTGC
24901 TCTCTTATGA TAATTTTTGT CCTCCCAGTT CCCCCGGACC CAACCAAGGA
24951 CTTGTCCACA TAATCAAATG TTCATCTTGT ACTGTTTTAC TTTTCACTGG
25001 GACAAAAGTA TATTTTGTCT GTGGCTTCAG ATTTAGGCAC AAGCATAAGA
25051 GCAAATAAAT ATGATAATTA AAGTTTGAAA AACCACATTC CTTGCTTTTA
25101 CTCCTGTCTG ACCAAGCTTA GTATACGTGA CAAGGACACC TTCCCTATCA
25151 CGGCAAGCAT CCACAAAAGT CTCTAATGCT ATCAATTCTA GGATTTTCAA
25201 ATCAGTTCAG AGAAACTGAA ATCAACATGT CCCATAGTTC TTTGACCAGT
25251 GGGTTCTAGT TTTGACTTAA AAATTCACAA AGATTTTGTG ATAGCTGACT
25301 TAAGTTTAAA TTTTTTTCAA ATCATAAGAA TGAAGGGGAA AATATCTTCG
25351 AATTTAGCAT GCTTATTTGC CAAAATATCC CCTTCCCTTC CAGCCATACC
25401 CATCTCTTCT TCATTTATCT AGAAGAAGCC GAGAATCTGC TCTATCTAGC
25451 AACCTCTCCC AACAGGCTAG ATCACTTGGT AGAAATCGGA AGGAGAGAAC
25501 TTGATTTAAT GTTGGCATAT TGCTGTCTTT ATGCTTGGCC TGATTTGAGC
25551 ACAAGGGACT TGATGGGAGA TAAGATTAAG TCCAGCTCCT TTATACCCTT
25601 CAGAAAACAA TGAATGCAAA TGAATTCATA AACATTGCTA ATAGGCTTCC
```

FIGURE 3I

```
25651 AAACTCATGA AAGTTAAAAG TTAGCAGAGA CCTTGGAGGC AAATTTGAGC
25701 AATGTCCTCA TTTGCAAAGA TGAGAAAAAA GCATTCTAGA GTGGCTCAAC
25751 CACTCATCCT AGGTCATATC CCCAGCTGTG GATACAATCA TTGCAAGCAA
25801 ATGGTGCAGA CCACGTGCAC TAATTGTCAC TGCTCTCCTT TGCTGTCTGT
25851 AGGGATGCTT TTTCATGCTC CTTGTTCAAG TTATTAACCT TTCTTTCCCT
25901 GCTGTCCTAA AGAGAGCAAA GTAATCAAGA TTCTCTCCAA ATACTAAATC
25951 AGCGTAACTT GTTCATTATC ACAGCTGATT AAGTGTCAAA GACAACTGTG
26001 TCTGAAAAGA ATATATATCT TTTTTTAGTG AGGAAAAGAA TGAAACAGAC
26051 ACTCCCTTGG AAGAGGAAGG GGATAGCCTG TAGACTTGCC CTAACAATGA
26101 CATGCGGCAC ACACCATCCC TCTGATACTG CTTTTGCAGC TGTTCTGGTC
26151 CTTAAATCCA CAACATGTGA TTAGCCATGC CTGGAAGCCT TCAACATTTG
26201 CAAATATTGC CTAAACACTT TCTGAATAAA GTTTATACTG GAGCTCCAAG
26251 CCAATGACAC ACACTTAAAA GAAGCAGGTG GTTTAAGTTT TCATCTTTTC
26301 TTTCCTTTTC ATTCCATTTC CTCCCTCCCT CTTACAGACC TGCATCAGCC
26351 CCCCCTGACT GTGGGTTAAG TCATTTTATT AGCAAGTCAG GCTCTAATCC
26401 CAGCAGCTGT ATTGCTTTAG TTGTGCAATT AACACAGTAT AATCTGCAGG
26451 AAATCAACTG CTCCCTATTC AAGTGTTTCA AGTAAATTAA CTGATCAAAT
26501 GTTGCAGCTT TTCCCTGTGC TCCTGGATTT TGGCCATGGC TTTGATTACT
26551 GATTATTGTA ATTCCCACAG GTGGATTTTT CGTTTGAAGA AAATATCTTT
26601 TCTTGTGTTT ATGTATTCAT GGGCGTGTGT GTGTGAGCGT GTGTGTATGT
26651 ATGTGTGTGT GTTCTGCAAC TGTAAATTTG AAGTGGGCGT GGGTGTTTCC
26701 TGCCCTTAAA GTAATTAAAT TTTTTGCCAA GGAATTACAT CAATGAAACC
26751 TGAGACTGAA ATATGTATCC GGTGTTTCAT GTGTTCTAGT ACTTTTATCG
26801 CCAGATTAAT CATTATCTTG GGCAAACACG ACTTGACTTT TTTTTTCCCC
26851 ATTGCTAAGT TGTGTATTAC TTAAAATCCA TTTTTCGTAT GTTACCAAGC
26901 TAGCAACCCT AGAAAACAAC TGGCAGCTGA TTTTCTCTAT TATCGAAAAT
26951 GTTCGGCTGC CTTGGGAGGT GCAGCCTTCC TTCCTGCTGT AGACCTTGCC
27001 ACTTCGTGCA GTGAATTGCT TCTGAGGAAA GCAGTTATTC AAATGCGATC
27051 TGATGAATGT CACCTTTTGT AATTTTTGTT TTGTGTCAAA TGTATGTTTC
27101 AGGACTACTT CACAGACTTA ATCACTAACG AGAGCATTAA TTACTTCAAA
27151 ATGTCTAAGA GAATGTATCC CCATAGGCCC GTTATGATGG TGATCAGCCA
27201 CGCTGCGCCC CACGGCCCCG AGGACTCAGC CCCACAGTTT TCTAAACTGT
27251 ACCCCAATGC TTCCCAACAC ATGTAAGTAA CAAACTCAAC TCTGCGACCT
27301 GCCGAACATG CCTTTCCCTT TTCTCCTCAT CCCACTCCTC TCCTTTACCC
27351 CGTTTCCTTC CACCCTGCGT ATCCACAAGG CTTTCTTCAT GAAAGGATAA
27401 CTTAAGAGCA GACCACGGAA CAGGCAGAGC CGCTGAGCCT GAAAGAAAGC
27451 GCCTTATCTG GGTGGTTTGA GGAGGAATCA AATTTCCAGC ATTTACAAGT
27501 AGCTAAATAG AAAGGAAGAG ATGCACATAG AGTGAATGGG GGCAAGTTTT
27551 ACAAGAGTTT CCTTTCGTTG TCTTAAATAA TATTCGTGTG TCTGATCTAA
27601 TAATGATGAT GATCAAATAG TATGCTTTTC ATAGCTGCAC AGTGGGGACC
27651 TCTGGTCTGG TTATAGAAAC ATGGATTTAT TTTCCAGGCG AATACCGTAG
27701 CAGCTTTGCT GCAGACGTGC AATTAGAATT CCTGCAGAAG GCAGCTTGAG
27751 TGGCTTGCCC AAGAGGGCTT CTCAGGTCAC AGCTTTAAAA TAACCTGATT
27801 TTTTTTTTTT TAAAGAGGCA GGAGTCTTGG AGATGGGGGG TGGGAAGGCA
27851 CAAGGGAGAG GGCTGATGGC GTGGAGGGAT GAGACAGAAC AAAGAGCTGT
27901 CGTGTGCCCA CAATTCTCAC CAGCCAAAGG TGGAAAAATC TAGATGCTTT
27951 GGCAGCAAAG AACATGATTT TGTTGTTCAC TCAGTTGACA CCATTTCTTC
28001 CTAAGCTTTG CCATCAATAT CCAGTCTTCC ACACAGAGCA GTGGAGTTGG
28051 CTCTGTGTCT GCTGAAAGCC TGACCATTAG GGAGACAGGG AACAGAAAAT
28101 TGGTATCTGT TTCCTATATT GTGAAACCTC CAAAATTGGT TCTTAATCTA
28151 TTTGTACTTA AATATCATCT CTTTTCATCC ACACTGGTTA TTAGCCAAGA
28201 TTCCAGGCAG AAAGAACCTT ACGAAAATAG GTAAGTAACT ATGCAGGCTC
28251 TCTAGTTGCC GGTCACTATA CATCCCTAGA GAAGTTTTTA TAAAATGTTC
28301 TCTTTTTTTT GAGACAGAGT CTTGCTCTGT AACCCAGGCT GGAGTGCAGT
28351 GGTGCAATCT TGGCTCACTG CAACCTCCGC CTCCTGGGTT CAAACAATTC
28401 TCCCACCTCA GGCTTCTGAG GAGCTGGGAC TACAGGCACA CGCCACCACA
28451 CCTGGCTAAT TTTTTGTATT TTTAGTAGAG ACGCAGTTCC ACCATGTTGG
```

FIGURE 3J

```
28501 TCAGGCTGGT CTCAAACTCC CCTGACCTCA AGTGATCCAC CCACCTCGGC
28551 CTCCCAAAGT GCTGGGATTA CAGGCATGAG CCACCGCACC CAGCCTTATA
28601 AAATATTTTT ATTTGTACCT TAATGTAACT GATTGACTTA TGACTCCTGG
28651 TCAGTGGTAC ACAGATCATC TCTATGATAT CATGTGACTT AGACCAGAAA
28701 GAAGGAGGCC AGAGCTGACT CAGGACAAGA ACTAACAATA TGAAGCCAGG
28751 GTGGGTTACC TACTGAGCAT GCCCAGGAAC TCAGAGGATG GAAGTGTTTT
28801 AATGCATAAA ATATCATCGA CAAATCATGA AGGTTGCCCC AGCACCTGGG
28851 AATATAGCTG GGATAAGCCA TTATGTTTTG GAGTCAACTC CATGGGTGGA
28901 TATTTAAGCT TCTGAAGATC TTCCCCTATA TACAACTCTG CGAGTAAATT
28951 CATGAATGAA GCCCATGTGT GACAAGTGGC TCTCCATTAT AGCTCACTTA
29001 CAAATTTAGT AGCCAACTGA TTCAATGAAA GGAAAAAGTC CTGCGGGCTT
29051 TTTCAATACC CCTGAACCCC CCTGTTCCCA TTTCTGTTGA ATCAGAAATC
29101 ACTTTACCTA TCTTTGTTGC ATTAGCAGAA ACCCAGTCTA AGGTGACTTC
29151 CTATAACTGT AAACTTTACA GATGTTCCCT CAAGCTGGAG GAGAAGGGGT
29201 TGACAAAACA GAGTGTTTTG TGGCTCCTTA AAAGTCAGCC TGCCTTTGAA
29251 GCTTTGAGGC AAGGTCCTAA GCCTGCAGGA AAATCAGCCT CAGGTCAAGA
29301 GTTTATAAGA GCTCAGTTGC ATGGAATCAG TACTGCATGA GGGGAGGAGC
29351 CTGCAGAGTT CTCAGGGTCT CAGCAATAGC TTTTTGAAAA ACATCTCTGT
29401 GCTGGCCAGG CGCGGTGGCT CACGCCTGTA ATCTCAGCAC TTTGGGAGGC
29451 CGAGGCGGGC GGATCACGAG GTCAAGAGAT CAAGACCATC TTGGCTAACA
29501 CTGTGAAACA CTGTCTCTAC TAAAAATACA AAAAAAAAAT AAAAATTAGC
29551 CAGGCGTGGT GGTGGGCACC TGTAGTCCTA GCTACTCGGG AGGCTGAGGC
29601 AGGAGAATGG CATGAACCCG GGAGGCGGAG CTTGCAGTGA GCCGAGATCG
29651 CACCACTGCA CTCCAGCCTC GGCGACAGAG CCAAGACTCT GTCTTAAAAA
29701 AAAAAACAAA GAAAAAAAAA GAAAAACATC TCTGATTCCA GTAATTAAAA
29751 ATTCTATTTC ATTCCACGAA TATTTATCAG TGCCACATGT GACACTATGC
29801 AGCCCAGCAG GGATATAGAT AAGCGTGAGG AAGACACAGT TGCTAACATT
29851 TAAGGACAGA TAAACTAAGG CAGGGGTTGG CACACTGGTA CCCACAGTCC
29901 AAACCTAGCT TGCCACCAGT TTTTGTTAAC AAAATTTTAT TGACACACAG
29951 CCATGCTCAT TCATTTATGT ATTGTCTGTG GCTGCTTTCA CAATACAACA
30001 GCCAAGTCGA GTAGTTGTGT CAGATACCAT ACAGCCTGGA AATACTATCT
30051 CATCCTCGAT AAAGTAACTT TGCCCCAACC TCTGCTCTAG GGGCAGGATG
30101 GGCAAGTGTC CCAATGGCAA TATCACCAAT AGGGCCAGAA GTGACAAGCA
30151 CAGAGCAGAC GTTCGCAGGG CTGTGGAGCG GGGAGGGAGA AGCCTTCATA
30201 TCTTTAAAGG AAACCAGGAA AACTTCATGG ACCAAGGCTT CAAAGTGGGC
30251 CTCAAAAGAT GGGTAAAATT TCTGCAGATA ATTGTTTAGA GATTGGGTTT
30301 CAGGAAGAGA ATATGGCAAG GACACGTGGT CACTGTATAA GGGAGGCAAT
30351 CTAAGATGTG TCCTAGAAAC TGGAGAATGG GCTACAAAGA AAGCAGCACT
30401 AAGGAACAAT GCTGCAGAGG GAAACTGTTG CAGAATATTG AGGGTGTCAG
30451 TGAGTTTGTA TGTAACTGCA AGCAGAGAGT CACTGGAGGT TGGGTAGTAA
30501 CAAAATAGGA GGTGGCTCAG ACATTTCCAC ATGCAAATAG ATTCAGTAGT
30551 TCCTTTTTAG TTCAAATGAA CCTTCTATTG CCCTTATTAG TGATTCTATA
30601 AAGTAAAATC TACACAGTGC AGAGGGTGGC CTTAGAGGCT AACGAGCCTG
30651 GTTTCCTGCC TCAGCTGCCC TCACTGAGTG TAGGGGTGCT TTCTTTAATC
30701 TCTGGAAACC TCCACTGTCT CATCTGTAAA ATGGAGATAA TACTAACACC
30751 TTGATGTGAT GTCATGAAGA GAAATTAAGA GAGGCAGTGT AAGTAAAGTC
30801 CCCACATAGA GCCTGGGACA TACAAGCCAC TTCATAAGTG TCAATTCTTA
30851 TTGAACCTTT TTATTAAGAA ACTAACAATA TTCTATCATT CTGGACCTAC
30901 AAAAGGGCAA TTTCATGTGG CTCAACTTAA GGTTTAGGGG AAGCAGTGAG
30951 AGAAATGACA ACTTGATGCT TGTCCATTGT GACATGACAG ACCTCTTGAC
31001 AAGCTAAGAC TCCCATTGTG ATGAGCCTCT CACACCTGGC CATTCCAATG
31051 GAACAGACAG GGTAAGGACC AATCTGGACT GTGTTATCTT TTCCAGGTGC
31101 AAGTATGTGC TATGGGTAAG TGCCAGTTTG GAGAACTCCC TTAGCCACAG
31151 GAAATGAAAA TTCATGTGAT TGTTTGAAGG ATTCAGCTTC TCTTTGCTGC
31201 TAATCCTTGG GTTTTGTGCA CCTAGAATGT GGTCTCCTGC AGGCCCTGAA
31251 AGCCTTGAAT TCCTGGCATC TTTGCTGTGA AGGTCTCCCT GGCTGCTGCT
31301 GGAGGAAGGG GCTGGAAGGA GTGAGTGTGT GCACAGGTTC AGAGTTCAGT
```

FIGURE 3K

```
31351 CTTCAGACAA AAGGAGTGAG ATAAATTGAA GACAAGCTGC CGATGGTAGT
31401 GCATGGAACT GCTCAATGAC CAGCTTCCTT AGCGAAAACA TTAGCAACAC
31451 ATTCAGGCAA AGGGATGCGA GAAGTTAAGT ACTTTGCAGA AATATTTGAC
31501 AGGCCCTGCA AACACTGAGC AAGAAACCAT AGGTTCTCCC CAATTGCAGG
31551 GATGCAAGTA ACGTGAACAC TTTCCTTTCG GTCATCTTCC TTGGTGGTCA
31601 GGCATCATCT GGATCACTTT CATCTGGCAT CGGGTTATAA CTACCTGACC
31651 CTCTCAGACT GGGGTGAATG TATCATCTTT CCAAGGTGTT TGCCGTTCCC
31701 AACAAAGAGA GGAAGCCAGT TCGCTATTGG CCTGTTAGCT TTACAAACGG
31751 ATGGTAGAGC TTATGCTTAC CAAGGAAGAG TGAAAGGGGA TTATCGACCA
31801 CTTGTTGACA GGGAAAATAG TTTAATCAAA CTGTAACTCA GCTACTCATG
31851 GCCACTGAGA AATCTGAGAA AGCCTCTGTC ATAATAACAC ACATAATAAT
31901 CCTAGTATTA GAAAGCCCTG CGCTCTGGCT AAGACTCTAC TATACTTTTC
31951 AGTAACTTAT TTCCCCAGAA TCTCCATAGG GATGCAATTC CTTCACCCCT
32001 GCTTTAAGTT ACTTCTCTCT CCTCGCCTCA GTGATGTCAT CATATACACC
32051 TGTGGACAAA AGCCGTGACA GGGAAGGAGA TGCCATTTAC GTCCCTGGTG
32101 ATTCTATAGG AAACTAAGGG ACCTCCTTAT CACCCTTCTA TGAACTATGC
32151 CCCTGTCAGC TTTAAAAATT TGTTGTTGTT ATTCCAATTT TTTTTTTTTT
32201 GAGATGGAGT TTCACTCTTG TTGCCCAGGC TGGAGTGCAA TGGCACAATC
32251 TCGGCTCACC ACAACCTCTG CCTCCCAGGT TCAAACCATT CTCCTGCCTC
32301 AGCCTCCTGA GTAGCTGGAA TTACAGGCAT GCGCCACCAC GCTCGGCTAA
32351 TTTTGTATTT TTAGTGGAAA CGGGTTTTCT CCATGTTGTT CAGGCTGGTC
32401 TTGAACTCCT GACCTCAGGT GATCCGCCCG CCTCAGGCTC CCAAAGTGCT
32451 GGGATTACAG GCATGAGCCA GCACACCTGA CCTGTTATTC CAATTTAACA
32501 GTTCTTTCTT CCCATACCTG TAAATGTGTG TGACTGTGTG TGTGTGCATG
32551 TACACTCACA CACACACAAA TACACAAGTT CAAGTGAAAT CTAAATGCTT
32601 GGTAAAACAG TCCATGTGCA CTAATTTGCA AGAGTTGTTG TGAGGGTAGA
32651 GCTTTTGAAT AAACATAGGT TGTCAAAGGA AAAACTCCCT CTGTGTAAGC
32701 CACAGGACAA AGGTTTTGAA ACACCTTTGT TATCTAAAGC TGGAAAGAAA
32751 TGTCTTGCCT TAAAAGAATT TGCACATTCG TACCTCTTTC CACAAATACG
32801 TGAAAGGACG TGCTTTTGAA GATAAGAAAA GTTTAAATTC TACAAAAAAA
32851 AAAAATCTGA TTTGGGCAGA ACTCATTGCT CCCTTTTCTC TGTTTCTACC
32901 TTGTTCTTCT CTGGGTGGAT CATTTACTAC TTATACTGTC AGTGTTGGTG
32951 TTGCTTGTTT ACTTAGATCC CTGAAGTCGA GTTGCACAAC TCCAGGGGGC
33001 ATTCAGATAA AATATCATGT GAATGATGCC CTGGAGTTTT GCAGGTAGCT
33051 TTGTCCTGAA GACAGGGACA AAAATGTTTC ATCTCTTTAC CTCCCAGTGC
33101 CTGGTGGACA TGCCTTCGGA CCAAGTAGTT GCACAATTCA TTGTTGCTTA
33151 GCAAATGAAC AAATATGTTC ACCTCACTAA ATAGCTGACA TGAAAACATT
33201 TTAAAAATAG TATCAAGATA TTTAAACAGT CGATTTTATG AATTTAAAAG
33251 ACACCTAGAG ATACTACAAT TCCGTAGTTT TTTAGATTAA AAAACAAAGA
33301 CCCAAAGTCT ATATTTTTTA AAGGAAGGCC CAGATGGTTT TGTGAAGGTC
33351 ATGTGAGTAT TTAGGGACAA AACTAGAGCT GAAACTCAAT TCTCTTGGCC
33401 CCAGGTGATC TTCTCACTCC ACCAGACTTA CTCAGTTCAC ATCACAGTCA
33451 CAATTCAGAT TAGAGCTATG AACAATTCTA TCCATTTGCA CAATTCTAAC
33501 TGGTGTTTCT AACTTCATTA AAAGACTCTG AATTATTTTT CTTATATACC
33551 TCTAATCAAG ATCATTTGGT ATTATCCTGC ATATGTTCAA ATGTTACCTA
33601 TCTACAGATA TTTGAACTTA GGTGGGGAAT ATCTCCACAA AGTCCATTAA
33651 GTAAGTTCAG TTTTAGTGAA AACTGAGATG GTGCAGCTTG AGAGATTAAG
33701 TGTAGAATTT CCAATGTAAT GCTTTGAATG TGTACCTTAA ATCTGTATCA
33751 CTGGCTTATT CTGGGAATTG AAGTCTTATT TCATTTCTCA GAGAATGATG
33801 GTTCTGCTAC CAGTAATCTT TAAGGGTTAG ATCATTCGGG TTTTTTGTTT
33851 GTTTGAGACT AAATAAATGA AGAAAACACA TGTTAGATAC AAAACACTAG
33901 AAATATATTA ATTTTCACTG GAGCGACACC AAAGGCCATC GACATTAAAA
33951 ATGAACTCCT AAGTTCTTTG CAATTCCCCA GGTATAGATT TAATATACAA
34001 CACATGCATC TCTTGAAACT CTTTCTTTGC TAGTAAGAAT TATTCTCCTG
34051 AAATACCCAC CTGTCAAAAA GAAAGGTAAC ATTATTGATT TTTAGAATTC
34101 TTATTTCTGT CGTGTCAGTA AGCAATACCG GAAAGAAAAT CAAACACTCA
34151 GGAGAATTGG CATGATGGTG AAGGTTGAGC TTACAAGTAC AGTGGACTCA
```

FIGURE 3L

```
34201 AGTATCCATG ATCCAGCGCA CTGAGCAATA AATCCAAATG AGCAGTGACC
34251 ACAGGAAAAC AATATGCAGG GAGGCCTCGC TGGGAAAAGC TAAACTTTTA
34301 TATATGGGAA TAGTCTATGG AGGATTACAG GGGATGTTTT CTTGGGGGTA
34351 TAAGGTCTGG AGTGTGCAGT ACTGGGTGAA GCCCTTATCT AACAGGCAAC
34401 AGAAAGGTCT TCCCAGGTTA GGCACACGTG ACTCTACCTC CAACACAGAA
34451 TTTTTTTTTT TAAGAAAGCA ACAGAAATTT GCAAATGATA GTCTGGTCTT
34501 TTGTCCTCTC AATTTTAAAG CAAATAACCA GTATTGTGTT ATCTACCTTT
34551 TCATGGATGC ATCCAGTGTG CCTAGAAGGG CCAGACTTTA TTCTGTATTT
34601 GCAACAAAAG TAGACCCAGC AACTGATGGG AAGATATCTG ATTGGGAAGC
34651 AGAAGCAGCT GGTATTTTAA ATCAGGATGA AAGCTAAGAT TTTAGGACTC
34701 ACTTTTGATA GGAAGAAAGG ATATATCAAT TTTCCTTTTA ATGAGTGGGA
34751 TTTTTGAGGT ACTTTGTGGG GCCTCTGGTT CAAGACTGTG GCCAGTGTGG
34801 TGTTGTAGGA GGGGCACTGA TGGAGAGCTA TCCCGGTGCA TTATTTCTGA
34851 GCCACCTCTG TGCACTTTAC TTCCTCATTT GTAACATGGG ACTAATGTGC
34901 CCTGCTGAGT CCTCAGAGTT GCTGCAACAA TCAAATGAGC TATTAAGGGA
34951 TAAGCTCTTT TCCAGCTACC TATGAGAATG GGTATGATAT GGTCCCAGAA
35001 TTTGCTCTCT AGAGCCACAG AAATCTCTTA ACCCCTACAA GAACTCTTTA
35051 AAGTTGTTAT CCCCATTATA TAGATGAGGA AACTGAGACT TAGACAAAAA
35101 GTTGTCCAAG ATCACATAAT ATTAAGGAAC AGAGCTGGGA TGAATATTTG
35151 AGTCTAATTC CAAAACATTC TGGAATAACT CAATATGTGG TTTTCCATTT
35201 CTCCCAAAAA CAGGTACCTG CTTTTTTCAG TGGCTTGTGT TCCAGCTGAC
35251 AGCTCCAGGG CCTGTTTGAA TAATTCGAAG ACAATCCTTA GTTAGGAAAG
35301 CAAGCTTTAA TTATCACTGG GGAACAGAAG GCCGCATCTT CGAGGAATTT
35351 GGCAGACCTC AGCAGGGGGC AACCACAGGC CTTTGGCAAA AGATCACTTT
35401 TCAACAACAT TGTCAATTCC AGTGACCCCC GACCTTCCAC CTGCAGGTCC
35451 CTGAACAGCT GCTGTTCTGT GGGAAGCAGT GGCAGTCTGT CTTCCTTTAA
35501 AAGGCACATG CACACTCTGT CCCTGCTGCC TGCTGAGATC CCACCTGGGA
35551 CCTCATCCCC AGAGCTGGGG GTCATCTCCC ATATCAAGAA ATTAAGAAAA
35601 ATAAGGGGGG GCAGGAAAGG ACAGCTTTGA CAACAGTCCC TGAACTTTCC
35651 CTTTTAATAT AAGCCAGATT TAACGTATGT CATTCTGTAA ATCCGGGAGT
35701 CCAATTTGAG GCTTGTAATT TGCTGCAAGC TTCCCTGTTC CTCCAAGTGG
35751 GGTGGAGCTA TGCCAAGCAC ATCAAGGTAA CTGGTGGAAG ATATAATTTC
35801 CCCACTGTGA GCCTGCATTT CAGTTCCCTA TTGTAATTTT TATTTGTGTT
35851 GAGGTTTTGT GGTTTTAAAA AAGTCAACCA GATTTATTTT TAAATTAACC
35901 CAGCCCAACA TCAAAGGCAA TAAGTAGAGG ATGTTTAGGT ATTATAAAGA
35951 AACCCTGTGT AATCTGTTAT AGCTGTATTC TTTCTCAGGG CATGTAATGG
36001 TAAATGGTTA GGGGCCTTTC ACAACCAACT TTCTATATTT CTCTGACCTC
36051 GGACTACCCT CATGGGCAAA AAACCCTTTT TGAGGGGATT TAGTAGCCCC
36101 TCTCTCCTCC TCCTCAACCT CTTAATCTAA TCCTGTTTGT AACGCAACAT
36151 GCTGCATGAA GAATACGAAA CATGGGCTTA AGTCCCTCCC CACTTCCCTT
36201 ATGACTGTGG TTTACTTTTA GATATGAAGA ACTCTTTCAG GCCAAAAAAA
36251 AAAAAAGGGG GGGACCATTT GGTTAACGAA CCATTTTCTT TGGTAGGCAG
36301 GAGAAAGTTT ATATTGAAAG TTTATCTTAA GGATGACAGG TCATACCTGA
36351 AGGGTTTGTT TTGGAATACT GTGGATTTTT TCTAACCCAA ATAATTACAA
36401 GAGAGTTCCT TGTTTATTGG CTCATGGAGG AAATTCAAGC GCCTCTGTTC
36451 TAGGCATTTT AAGTGCTCTG TATATATGGT GGTTGTTCCT CAAAACAGCT
36501 TTGGGTTTGT TTTTTGTTTT TTGTTGTTAG TGGTGGTTTT TTGAGATAGA
36551 GTCTCGCTCT GTTACCCAGG CTGGAGTGCA GTGGCGCAAT CTCGGCTCAC
36601 TGCACCCTCC ACCTCTCTGG TTCAAAAGAT TCTCCTGCCT CAGCCTCCTG
36651 AGTAGCTGGG ATTACAGGCG CCCGCCACCA TGCCCAGCTA ATTTTTGTAT
36701 TTTTAGTAGA GACGGGGTTT CCCCATGTTG GCCAGGCTGG TCTCGAACTC
36751 CTGACCTCAG GTGATTCACC CGCCTGGGCC TTCCAAAATG CTGGGATTAC
36801 AGGCGTGAGC CACCATGGCT GGCCCAAAAC AGCTTTTTAA GAAAAGTGCT
36851 ATTAACCCCA TTTACAGATG AGCACATTTG AGCCACACCC TCTTTTCCAC
36901 ACTCTAAATC TTGTCTCTTT CTTTAAACAT GAGTTACTTA TACTTCTGAG
36951 CATAACTGAG GCACTTTTAG AGACAGTGTC TTCTAAGCTC AATGTGATAT
37001 TATTTGTGCT GCTGTGCTGC TACTGGGTAA CCAGCACCCA TCCTGGTCAC
```

FIGURE 3M

```
37051 CAGGGTAACT TTGTCAACCA AGAAGGCCAA GGATCCCAAA CCAGCATTTT
37101 CTACTATCAA AAGAGAGGTT CTGCAAATCC ACTGGCAGGA GAGAAAATAT
37151 AATAGCAGGT GGCATTTATA TGACCCAGTG TGCATGGCAG TGTCCCAGGG
37201 TATCACCGTG AATCTCAGAA ACTCCAGGCT TTCCCCATGG GAAATCCACA
37251 CCACCACAGA TCCAGTGGAG GACTCGGTCA AGACTCCTGA AATCAAAGAA
37301 CTCACAGTGA CTGATTCTTT CCCTAGTTTT ATAATATAAA TAATGGCATG
37351 GGGTCACATT CAGCCGTCAT TATCCACATC ATTTCACTGA TGGGATCCTC
37401 CTCAGACAGA GATTGGGAAT CAGATTTCTC GGTCACATAA ACTGTTGCTC
37451 ATTCTGTGAG GCTGCCTATT TGTAAAGTTG TGGTTCTTAT TAAAAGCAAT
37501 CTCAGACGTA GCAAGCACCC CTCACTTCCC TTCTCATTCA TTTTGTTAAA
37551 GCAAATGGGC TTTGGAATTC AGGCCTGTTT CTACCACTTA CTAATGTTGT
37601 TAATTTGGAG GAGTTCCTCA ACTTTGCCAA GGCTTGATTT TCTCTGCTGT
37651 AAAGAGGGAA TAATAAACCT ATTTTACAGA GCAGCTGAGA CAATTAGGTG
37701 AGTTAATGTA TATAAAATGG TTTGCATAAT ACCCAACACA TATTAAACTC
37751 TCACTCGGTT TTTAATATTA ACCTCTATGT GCTTAATAAC ATTGAAGAAG
37801 AAGATTCAAG TAGATTATAG TCTGTTAAAG AGTTCAAATA TAAATAAATA
37851 ATTCTCAGGG TGAGAATTGC CATAGCATAG ATATGTTACG TACCCATGGC
37901 AGAGCGTGAG GTGGCAGCAT CTAATGGTTG AGGGAGTTGG GTGAGACATC
37951 AAGAGAAGGT GACATATTTT TTTGAGTACC CAGTGGAAGG CATGGGATAC
38001 CATGTGGATC TCTGCAGTAG ATTAAATATA GACTTGAACT AACCTATCCT
38051 GGAACAATAG GACAATATCC TTGTGGCTTA CAGTAATTAT TCCCTGCACC
38101 TATATTGATT TGTTTATTAA ACGAATAGCT TTATTGGTAA ACATGTATAT
38151 TGCGGAAGTA GACTTGGTTA TCATTCCCAC AAGTCCAGTT AAAGTAATGG
38201 CATCTATATA AAAAACTCAT AAAAACTAGA TATGTAAGTA ATCAATAAAA
38251 TACTCTTCTC AAGTATTCAG GAGAAAAAAT GTGTTGAAAT GATGATTCAT
38301 CATTCCACAT AACGTATTTG TGACTACATT TAATAGCCTC ATTAGCAATA
38351 AAATTTTTAT GAGTTAACAT CATATGAGAA TATTCCCTTG TACCTTACCG
38401 AGACTTTATC TGTAGATTTG TAACATAACC ATAATCATCT TGGTATGTTT
38451 CTTACACATT TTATTCAGTG AACCCAAATG AACTTCTAAT TACATGTTCA
38501 GCTGCCAGTC ATGGTTTTAT ATGTTTGAAT ATATATACCT TCAGAGGATA
38551 TTTGCTCTTT GGGGTGGTGA AGACTTCATC TTCTTATAAA TGCAAACAGA
38601 AGATAGTTGG AAGAGGAAAA TGTTTTAGCA GTGTCTCAAT TATCTCTCCT
38651 TAATGATTAT TTCACAACCT CGAGATATTT TCCTAAAAGA CTAAGTAAGA
38701 AATATATAGT AAGATTCCTT TCTGGATATT TTCAGAACTC CTAGTTATAA
38751 CTATGCACCA AATATGGATA AACACTGGAT TATGCAGTAC ACAGGACCAA
38801 TGCTGCCCAT CCACATGGAA TTTACAAACA TTCTACAGCG CAAAAGGCTC
38851 CAGACTTTGA TGTCAGTGGA TGATTCTGTG GAGAGGGTAA GCACATGAAC
38901 CTACCTCAGT GATAGTTTTT GGCCCAGCTT CCTTTGTGTA GACTTATTCT
38951 TGCCAATCCT GTTTGGTTTT TTCCCCTTCA TTTTCCAGCA TCATTTTGAG
39001 AGAGAAAGAA AGAGAGAGAG TATGTGTTTA GTGGCTTAAT CATCCCTCCC
39051 TTATCTTGTC CTCATTCCAT CTACCTCTCC AGGGTTGGTT TCTTATGGAG
39101 CCAGTAAAAA AGAGGAGAGA AAAATCAAAT CAGCGTAGAT CAGGGGCCAC
39151 ATCCTCAAAG GCAATAAAGA ATTGATGGAG CTTGTGCTGA ACTTGAACTT
39201 TAAGTTAAGG GCCCCATCTA AAGGAACAGC AATTACTCAG CTCCAGCTAA
39251 ATTTTGCCAT GTAGAAATGT GGATCAAGTA TCAGCAGGTC TTCTGACTTT
39301 TTTAAAGAAG CCAGAAACAC AAAAAATTTT ATTTGAAATT TTCTGAACTT
39351 TGAAACATAG TATAAGCCAA ACAAGACGTG CCTCAGGCTG GATTTAACTG
39401 GATCAGGCTC AGAAGCAGCC TGTTTTTAAC CCTTGGTAAT TAGATATGTG
39451 ATGATAATTT TAACAATGGA TTTTCAAAGT ACAACCTATA AAGTTTGATG
39501 GTAGAGGTTG TTGTGCGGGG TGTTTTTGTT TTTGTTCTAC CAAACAAGCA
39551 AACAAAAAGC CTAAAAGTAG AATGTGCTAG ATTCCAAAAA GTTACATTTC
39601 ACCTTTACCA TTGGACCTTT CCCTCCCAGA CTGTAAGCAA ATAGAAAATG
39651 TGGATAATGT TATTAAAGCA ACTCTTGCCT TTTAAAAATA ACAGGAAAAA
39701 GATTTGGGGG CAATCGTGGC AACACTATTG AGCATCATCT TATACCAGCA
39751 CAATTGATTC TGACTTGTTC CTTTGCTGTA TTTCAGCTGT ATAACATGCT
39801 CGTGGAGACG GGGGAGCTGG AGAATACTTA CATCATTTAC ACCGCCGACC
39851 ATGGTTACCA TATTGGGCAG TTTGGACTGG TCAAGGGGAA ATCCATGCCA
```

FIGURE 3N

```
39901 TATGACTTTG ATATTCGTGT GCCTTTTTTT ATTCGTGGTC CAAGTGTAGA
39951 ACCAGGATCA ATGTACGTAT TTCTCTGTTT GCAACATTCA ACTGTCGTAC
40001 CTCAAGTGTG TCTAAGATAA TTCAATTACC AGTCTCAGTA TCTGGTTTCC
40051 TTTCATCCAA AACAAAAAAG GATGTGTGTA GGCTGGTTAA TTTCGAAGAT
40101 GAAAACCTTT TCCTCCCTGC CACATCTTAA ATTAGCTCAA GTATACTACT
40151 TAAAGAGAAA GGAAAAATAA GTGTATCAAT GACTAATTCT CTCAAATTGA
40201 CTGGAATCTA TGTCTTTTTG GTCTGTGTGC ACAGACAGGA TGTGATCTTC
40251 TGGGATATCA CCCTTCTTTG AATCAGAGAT ACGCTGTCAT TTAAAAAAAA
40301 AACCTGACAC CATCCTTTTA GTGTTTAACT TTTAAAAATT ATTCCGAAAG
40351 AAATGTTTTT AAAAGATAAA TTTTGAAAAG CTGGCTTTTC TTTTAAAGGA
40401 AAAAGAGCTA AAGGACTAGG CTGCTATTTC TGTCACTGTA GGCAGGTCAC
40451 TGCTTCTCTT TGCATCTCTA TTTTCCCATC ATGAAATGGC CTTGCCTATT
40501 TTCCCATCAT AAAATGGCCT TGTCAATCAT CTCAGGATGT TTTGAATAAA
40551 ATGGGATTGC ATCCATGAAA GAATTATGGA AAGACTAAAA GAAAAAGTGG
40601 AAGTAGAATC CAGAAGCTGG AATGGCCCTT GAAAAGCATC TAGCCTGGAC
40651 CCCTGATGTA ACAGTGAAGC TAGGCAGACA GCGTCAGTGC CCCTCTCAGA
40701 TCCCTGATTC TGGAAGTGGT GGCAGTGGGG CCCAGAGCCC AGATGTTCTG
40751 AATCTCCCCC GAGTACCACA TGTGCTGCTG CATCATACTA CATCCTGGAG
40801 AGAGGGCAAT TGAAGTAAGA AAGGTTTCTT TGAAGAATGT TATTGTGCTT
40851 CCTAAGATTA TTAGAAACAC CCTGAGAATT GTCAGATCTA TATCTAGAAG
40901 GCTTTATGTT TTAAGGACTA GATAGCATAG ATTGAATTCA ACTGTAAAAA
40951 CTGTACATCC TTTTTTAAAA TATTGATTTT AAAGCTCTTG TTCAACGGAA
41001 AAGTTATGGA CTATTGGGTT TTAAGCAAAA GTATGCTTGC TGCAAAAACC
41051 ATGTATCAGG CTGCATCTTG CCTGGTGATG TGGTCAGAAT ACAGGGGTGC
41101 AGGCATCTCT CCAGCCTGAC CCTGGCAAGA GTCAGTTAAT CTTGCTCAGT
41151 GCCATTGCTG TGATCACACA CCCACCCTTG CCACACAACT ACCCATGCCT
41201 AGGAGACCAG ATGAGAGGGT GAGAAGAGTT GAAGGCCAAT GAGTCACTGC
41251 TGTAGAAAAA GCAGCCCTAA GTGCCACCTT CCCCTGGCAT TGGATCTCAG
41301 CCATCACCGT GTGCCCCTTT ACAGAGTCCC ACAGATCGTT CTCAACATTG
41351 ACTTGGCCCC CACGATCCTG GATATTGCTG GGCTCGACAC ACCTCCTGAT
41401 GTGGACGGCA AGTCTGTCCT CAAACTTCTG GACCCAGAAA AGCCAGGTAA
41451 CAGGTGTGTC ATTGTTCCTC CTCTCAGCCA GCCCCAAATA CACTGAGCTC
41501 CAGCTGGTGC CCAGAGCCAG CCAGCAGCTG AAGACATGGA GGCAGAATAT
41551 GCCTTGCCCA CAAGGATCAC CCCAAGCTGA GCATTTCTCA GCTGCTTGTG
41601 AATAGCATAT TGATGGAGAT GCACTCATGG TCTGTGGGAA GTGAGAGGTG
41651 TTTCTTTAAA TAAGCTGTTA GCACAGATCC ATTTGGAAAA ACGTCCAGAT
41701 GCCAAAAGTA AATATTATCA TTTTGCTTTC AGGTTTCGAA CAAACAAGAA
41751 GGCCAAAATT TGGCGTGATA CATTCCTAGT GGAAAGAGGG TAATTATTGG
41801 TTCCTGGGGT GCTTCTGGGA ACCAGTCCTA GTGGGCAGCT TTCCCTGCTG
41851 AGTATTTTTT TTCTCCTTAT TTTTGTTTAC TAAGCATGCA GATTTCGTAA
41901 ACCTAGTCAC AAGATTGAAT GGTTTGCTGC TTATTCTGTA GTGGTCAATA
41951 GAGTAATAAT TGCTGGATCA GAATTGTAAA GAATAACCCT CAAGTTGGTT
42001 AATTGGTACA AAAACACAGT TAGATAGAAG TTATAGAATT TGATAGTATA
42051 GTTGGGACAT TATCGTTAAC AATAATTTAT GTATATCTTA AAATAGCTAG
42101 AAGTGAAGAA TTGCAAAGTT CCCAACACAA GGAAAAGATA AATGAGATGA
42151 TGAATATCCC AATTATCTTG ATTTGATCAT TACACATTGT AGACTGGTAT
42201 CCATATATCA CACGTACCCC CAAAATATGT ATAATTGTGA TATATCAATT
42251 TTTAAAATAC CAAAAAAGCA AGAGAATGAC GACTCCACAT CCCCCAAAAA
42301 GAATAAATTC TCATAAGCTT GGACCAAAGC CTTTATCATG GGTGTAGATT
42351 TACTGTTGCA TTTCTCAGTG CTGGTTTCTA ATCAGACCAG TGGATTGAGT
42401 TTCTCTACCA TCCTCCCCAC GTTCTTCTCT AAGCTGCCTC CAAGCCTCAC
42451 CCGGCACCCT TCTTCCTACT TCCTACTTCT TTTCCTTGTG TGCCTTTCCT
42501 AGTTTTAAAT AGATAAATGT ATGCCATTGT AATTATTTCC ATTGTCACTT
42551 CTGGGTTTCC CCTTTTGGTT C
```

FEATURES:
Start: 2106

FIGURE 3O

| | |
|---|---|
| Exon: | 2106-2277 |
| Intron: | 2278-14101 |
| Exon: | 14102-14341 |
| Intron: | 14342-24487 |
| Exon: | 24488-24639 |
| Intron: | 24640-27102 |
| Exon: | 27103-27272 |
| Intron: | 27273-38735 |
| Exon: | 38736-38886 |
| Intron: | 38887-39786 |
| Exon: | 39787-40017 |
| Stop: | 40018 |

CHROMOSOME MAP POSITION:

Chromosome 8

FIGURE 3P

POLYNUCLEOTIDES ENCODING HUMAN ESTRONE SULFATASES

FIELD OF THE INVENTION

The present invention is in the field of enzyme proteins that are related to the sulfatase enzyme subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the sulfatase subfamily.

Sulfatases

The novel human protein, and encoding gene, provided by the present invention is related to the sulfatase family of enzymes, including estrone sulfatases. Specifically, the novel human protein of the present invention is a novel alternative splice form of a gene provided in Genbank gi5689491 and published PCT patent application WO200055629 (see the BLAST and Genewise alignments of the sequences of the present invention and the sequences of gi5689491 and WO200055629 provided in FIG. 2). The evidence supporting alternative splicing includes a different polyA signal used to create the protein of the present invention compared with the art-known protein; the stop codon at cDNA positions 1223–1225 and polyA signal at cDNA positions 1750–1756 are present in the genomic sequence; and the last exon of the cDNA of the present invention crosses the splicing site of the corresponding exon 5 of the art-known protein (these differences are illustrated in FIG. 2 in the BLAST and Genewise alignments of the sequences of the present invention and the sequences of gi5689491 and WO200055629).

Novel human sulfatases, such as the protein provided by present invention, are particularly useful as targets for treating cancer, particularly breast cancer. Sulfatases are important for generating estrone and 5-androstenediol from sulfated precursors. As stated by Purohit et al., (*Mol Cell Endocrinol* 2001 Jan 22;171(1–2):129–135), "The development of inhibitors to block the formation of estrone and 5-androstenediol from sulfated precursors is an important new strategy for the treatment of breast cancer". Thus, sulfatase inhibitors are useful for treating cancer and, consequently, novel sulfatase proteins are valuable as novel targets for the development of anti-cancer therapeutic agents. Purohit et al. found that non-steroidal and steroidal sulfamates, particularly a tricyclic coumarin sulfamate ("667 COUMATE") and 2-methoxyestrone-3-O-sulfamate (2-MeOEMATE), inhibited estrone sulfatase activity and "offer considerable potential for development for cancer therapy". The importance of sulfatases relating in breast cancer is further described in published PCT patent application WO200055629, "Novel Methods of Diagnosing and Treating Breast Cancer, Compositions, and Methods of Screening for Breast Cancer Modulators".

Enzyme proteins, particularly members of the sulfatase enzyme subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the sulfatase enzyme subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the sulfatase enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in pancreas adenocarcinoma, breast, colon, and brain.

DESCRIPTION OF THE FIGURE SHEETS

FIG. 1 provides the nucleotide sequence of a cDNA molecule that encodes the enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in pancreas adenocarcinoma, breast, colon, and brain.

FIG. 2 provides the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the sulfatase enzyme subfamily. Utilizing these sequences, additional genomic sequences were assembled and transcript and/or cDNA sequences were isolated and characterized. Based on this analysis, the present invention provides amino acid sequences of human enzyme peptides and proteins that are related to the sulfatase enzyme subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the sulfatase enzyme subfamily and the expression pattern observed. Experimental data as provided in FIG. 1 indicates expression in humans in pancreas adenocarcinoma, breast, colon, and brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known sulfatase family or subfamily of enzyme proteins.

Specific Embodiments

Peptide Molecules

The present invention provides nucleic acid sequences that encode protein molecules that have been identified as being members of the enzyme family of proteins and are related to the sulfatase enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in pancreas adenocarcinoma, breast, colon, and brain. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988*; Biocomputing: Informatics and Genome Projects*, Smith, D. W., ed., Academic Press, New York, 1993*; Computer Analysis of Sequence Data, Part* 1, Griffin, A. M., and Griffin, H. G., eds., Humana Press, New Jersey, 1994*; Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. The gene encoding the novel enzyme of the present invention is located on a genome component that has been mapped to human chromosome 8 (as indicated in FIG. 3), which is supported by multiple lines of evidence, such as STS and BAC map data.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. The gene encoding the novel enzyme of the present invention is located on a genome component that has been mapped to human chromosome 8 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol*. 182: 626–646 (1990)) and Rattan et al. (*Ann. N.Y. Acad. Sci*. 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific, assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in pancreas adenocarcinoma, breast, and colon, as indicated by virtual northern blot analysis. In addition, PCR-based tissue screening panels indicate expression in fetal brain. A large percentage of pharmaceutical agents are being developed that modulate the activity of enzyme proteins, particularly members of the sulfatase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in pancreas adenocarcinoma, breast, colon, and brain. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the sulfatase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in pancreas adenocarcinoma, breast, and colon, as indicated by virtual northern blot analysis. In addition, PCR-based tissue screening panels indicate expression in fetal brain.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in pancreas adenocarcinoma, breast, colon, and brain. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention farther includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in pancreas adenocarcinoma, breast, and colon, as indicated by virtual northern blot analysis. In addition, PCR-based tissue screening panels indicate expression in fetal brain.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in pancreas adenocarcinoma, breast, colon, and brain. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in pancreas adenocarcinoma, breast, colon, and brain. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254 –266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in pancreas adenocarcinoma, breast, colon, and brain. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in pancreas adenocarcinoma, breast, and colon, as indicated by virtual northern blot analysis. In addition, PCR-based tissue screening panels indicate expression in fetal brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in pancreas adenocarcinoma, breast, colon, and brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in pancreas adenocarcinoma, breast, colon, and brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in pancreas adenocarcinoma, breast, colon, and brain. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel enzyme of the present invention is located on a genome component that has been mapped to human chromosome 8 (as indicated in FIG. 3), which is supported by multiple lines of evidence, such as STS and BAC map data.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C, followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel enzyme of the present invention is located on a genome component that has been mapped to human chromosome 8 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in pancreas adenocarcinoma, breast, and colon, as indicated by virtual northern blot analysis. In addition, PCR-based tissue screening panels indicate expression in fetal brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in pancreas adenocarcinoma, breast, and colon, as indicated by virtual northern blot analysis. In addition, PCR-based tissue screening panels indicate expression in fetal brain.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in pancreas adenocarcinoma, breast, colon, and brain. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in pancreas adenocarcinoma, breast, and colon, as indicated by virtual northern blot analysis. In addition, PCR-based tissue screening panels indicate expression in fetal brain. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in pancreas adenocarcinoma, breast, colon, and brain.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. The gene encoding the novel enzyme of the present invention is located on a genome component that has been mapped to human chromosome 8 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res*. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr*. 36:127–162 (1996); and Griffin et al., *Appl. Biochem. Biotechnol*. 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol*. 217:286–295 (1992)), electrophoretic mobility of mutant and wild type nucleic acid is compared (Orita et al., *PNAS* 86:2766 (1989); Cotton et al., *Mutat. Res*. 285:125–144 (1993); and Hayashi et al., *Genet. Anal. Tech. Appl*. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in pancreas adenocarcinoma, breast, and colon, as indicated by virtual northern blot analysis. In addition, PCR-based tissue screening panels indicate expression in fetal brain. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1

(1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaninated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fuasion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res*. 20:2111–2118 (1992)).

The nucleic acid molecules can also be expressed by expression vectors that are operative in yeast. Examples of vectors for expression in yeast e.g., *S. cerevisiae* include YepSec1 (Baldari, et al., *EMBO J*. 6:229–234 (1987)), pMFa (Kuran et al., *Cell* 30:933–943 (1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol*. 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:

(a) a nucleotide sequence that encodes a protein comprising the amino acid sequence of SEQ ID NO:2;

(b) a nucleotide sequence consisting of SEQ ID NO:1;

(c) a nucleotide sequence consisting of SEQ ID NO:3; and (d) a nucleotide sequence that is completely complementary to a nucleotide sequence of (a)–(c).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

* * * * *

SEQUENCE LISTING

<160> NUMBER OF SEQ ID NOS: 6

<210> SEQ ID NO 1
<211> LENGTH: 1799
<212> TYPE: DNA
<213> ORGANISM: Human

<400> SEQUENCE: 1

```
tatttcattt tagtctcacc gtctccgttt ttctctgact gcccagaact ccagaaatca     60
ggagacggag acattttgtc agttttgcaa cattggacca aatacaatga agtattcttg    120
ctgtgctctg gttttggctg tcctgggcac agaattgctg ggaagcctct gttcgactgt    180
cagatccccg aggttcagag gacggataca gcaggaacga aaaaacatcc gacccaacat    240
tattcttgtg cttaccgatg atcaagatgt ggagctgggg tccctgcaag tcatgaacaa    300
aacgagaaag attatggaac atgggggggc caccttcatc aatgcctttg tgactacacc    360
catgtgctgc ccgtcacggt cctccatgct caccgggaag tatgtgcaca atcacaatgt    420
ctacaccaac aacgagaact gctcttcccc ctcgtggcag gccatgcatg agcctcggac    480
ttttgctgta tatcttaaca acactggcta cagaacagcc ttttttggaa aatacctcaa    540
tgaatataat ggcagctaca tcccccctgg gtggcgagaa tggcttggat taatcaagaa    600
ttctcgcttc tataattaca ctgtttgtcg caatggcatc aaagaaaagc atggatttga    660
ttatgcaaag gactacttca cagacttaat cactaacgag agcattaatt acttcaaaat    720
gtctaagaga atgtatcccc ataggcccgt tatgatggtg atcagccacg ctgcgcccca    780
cggccccgag gactcagccc cacagttttc taaactgtac cccaatgctt cccaacacat    840
aactcctagt tataactatg caccaaatat ggataaacac tggattatgc agtacacagg    900
accaatgctg cccatccaca tggaatttac aaacattcta cagcgcaaaa ggctccagac    960
tttgatgtca gtggatgatt ctgtggagag gctgtataac atgctcgtgg agacggggga   1020
gctggagaat acttacatca tttacaccgc cgaccatggt taccatattg ggcagtttgg   1080
actggtcaag ggaaatcca tgccatatga ctttgatatt cgtgtgcctt tttttattcg    1140
tggtccaagt gtagaaccag gatcaatgta cgtatttctc tgtttgcaac attcaactgt   1200
cgtacctcaa gtgtgtctaa gataattcaa ttaccagtct cagtatctgg tttcctttca   1260
tccaaaacaa aaaaggatgt gtgtaggctg gttaatttcg aagatgaaaa ccttttcctc   1320
cctgccacat cttaaattag ctcaagtata ctacttaaag agaaaggaaa aataagtgta   1380
tcaatgacta attctctcaa attgactgga atctatgtct tttggtctg tgtgcacaga    1440
caggatgtga tcttctggga tatcaccctt ctttgaatca gagatacgct gtcatttaaa   1500
aaaaaaacct gacaccatcc ttttagtgtt taacttttaa aaattattcc gaaagaaatg   1560
tttttaaaag ataaattttg aaaagctggc ttttctttta aaggaaaaag agctaaagga   1620
ctaggctgct atttctgtca ctgtaggcag gtcactgctt ctctttgcat ctctattttc   1680
```

-continued

```
ccatcatgaa atggccttgc ctattttccc atcataaaat ggccttgtca atcatctcag   1740

gatgttttga ataaaatggg attgcatcca tgaaagaaaa aaaaaaaaaa aaaaaaaaa    1799
```

<210> SEQ ID NO 2
<211> LENGTH: 372
<212> TYPE: PRT
<213> ORGANISM: Human

<400> SEQUENCE: 2

```
Met Lys Tyr Ser Cys Cys Ala Leu Val Leu Ala Val Leu Gly Thr Glu
 1               5                  10                  15

Leu Leu Gly Ser Leu Cys Ser Thr Val Arg Ser Pro Arg Phe Arg Gly
            20                  25                  30

Arg Ile Gln Gln Glu Arg Lys Asn Ile Arg Pro Asn Ile Ile Leu Val
        35                  40                  45

Leu Thr Asp Asp Gln Asp Val Glu Leu Gly Ser Leu Gln Val Met Asn
    50                  55                  60

Lys Thr Arg Lys Ile Met Glu His Gly Gly Ala Thr Phe Ile Asn Ala
65                  70                  75                  80

Phe Val Thr Thr Pro Met Cys Cys Pro Ser Arg Ser Ser Met Leu Thr
                85                  90                  95

Gly Lys Tyr Val His Asn His Asn Val Tyr Thr Asn Asn Glu Asn Cys
            100                 105                 110

Ser Ser Pro Ser Trp Gln Ala Met His Glu Pro Arg Thr Phe Ala Val
        115                 120                 125

Tyr Leu Asn Asn Thr Gly Tyr Arg Thr Ala Phe Phe Gly Lys Tyr Leu
    130                 135                 140

Asn Glu Tyr Asn Gly Ser Tyr Ile Pro Pro Gly Trp Arg Glu Trp Leu
145                 150                 155                 160

Gly Leu Ile Lys Asn Ser Arg Phe Tyr Asn Tyr Thr Val Cys Arg Asn
                165                 170                 175

Gly Ile Lys Glu Lys His Gly Phe Asp Tyr Ala Lys Asp Tyr Phe Thr
            180                 185                 190

Asp Leu Ile Thr Asn Glu Ser Ile Asn Tyr Phe Lys Met Ser Lys Arg
        195                 200                 205

Met Tyr Pro His Arg Pro Val Met Met Val Ile Ser His Ala Ala Pro
    210                 215                 220

His Gly Pro Glu Asp Ser Ala Pro Gln Phe Ser Lys Leu Tyr Pro Asn
225                 230                 235                 240

Ala Ser Gln His Ile Thr Pro Ser Tyr Asn Tyr Ala Pro Asn Met Asp
                245                 250                 255

Lys His Trp Ile Met Gln Tyr Thr Gly Pro Met Leu Pro Ile His Met
            260                 265                 270

Glu Phe Thr Asn Ile Leu Gln Arg Lys Arg Leu Gln Thr Leu Met Ser
        275                 280                 285

Val Asp Asp Ser Val Glu Arg Leu Tyr Asn Met Leu Val Glu Thr Gly
    290                 295                 300

Glu Leu Glu Asn Thr Tyr Ile Ile Tyr Thr Ala Asp His Gly Tyr His
305                 310                 315                 320

Ile Gly Gln Phe Gly Leu Val Lys Gly Lys Ser Met Pro Tyr Asp Phe
                325                 330                 335

Asp Ile Arg Val Pro Phe Phe Ile Arg Gly Pro Ser Val Glu Pro Gly
            340                 345                 350

Ser Met Tyr Val Phe Leu Cys Leu Gln His Ser Thr Val Val Pro Gln
```

-continued

```
        355                 360                 365

Val Cys Leu Arg
    370

<210> SEQ ID NO 3
<211> LENGTH: 42571
<212> TYPE: DNA
<213> ORGANISM: Human

<400> SEQUENCE: 3

gtatcaggtt tctcacgatt taaaacaaat gcacagaaac caaacagtca gtgcagaata     60

attgcaggct ttcagtgttc agcatgtaca gcaatcactg tggaatcacc ctgcgttatt    120

aagaagaaag caccaaatct tacattagtg acttctacag ggctgcgtta tcaattggag    180

ctgtcttgtt tgttgcagat aatgtagtca ggactgcctg gctgcagaca ctagagtttt    240

gtttaaaaac cgatttcttc ttgtctcttt ctctctcttg cagtataatt acaggctgca    300

gagtgaaaag cattagaact gtttacaaaa cagctcataa agtttaaaat aatggggata    360

cgtgtgtgtg tttgtgtaaa acaaaataat gtgtatggta ggggtaaaca atatccagtc    420

tttcttcttt cactaccccc tgtcaccttc cagaattaag ggcatgaagt tgagagatgg    480

agccctttcc tcctgctatg cgatgcttac acttaattag ttatgcctac ttatccaatg    540

ccagtttatt gttgcagatc aaaatacaga ttctcaggtg tatggggact gagtggctga    600

tgaaacagac tgctatctaa ttaattttag ggcagcctaa attcccataa agatgttccc    660

tcatgacata tgagaggaag attttatttt tttaatgagc cctttgctat ctttccaaga    720

gaaaagcttt cagcaggtta gtgttccaaa gtgagagggg catttttcca accctttcaa    780

aagcctcctt ctgtgcagct ttgcaaagat tttgcagctc gcccttctgg attttattta    840

tttatttttt aatgcggaag ggtagccgct gactccagcc tcggggccaa tcaatcattt    900

tgctttgcag gtttaagatc tgtgacaaag cgaaacccct gtgctatctg tgccttacca    960

gtctcaccaa caataagcct ggtgactgac aatcgagagg gggctctgtc cacgtaggtg   1020

ccggcacaag ctgaggacat gagtgggaca gaggaaccag ccttgcacgg aggaagcacc   1080

ttttccttct ggtgattgat tgatgggga cagtgaggag gttttcagag actggaaaaa   1140

attgtcccag tcacttacta tgaagtcttt gtcagcagaa aagactctcc ggggtagaga   1200

atgatataat gcagatgaca aatgacaggt gtgtgtttcg ttctgcttgc taggtactca   1260

gtatcacacg caggtgagtc agcgctcccc aacatgcccc ttgcgccatc tgctccccac   1320

atgcaaacac tcgttcccaa cgctctgtgg tttccctggc actgctggct cttcctaatc   1380

gatcgtcagc tctgttgggg atgtgtaaag tactgtcaga gtgtgagcag ggtgatacct   1440

taccaccctt ttatggagct gattatgaaa tgaagatagc atttgaatca tttgttagca   1500

gttctgaaag ttgtttcctt ctgttcctcc cttttggagc acagaagaaa aaatatatgt   1560

aatatataca catataatat gctgttgcaa gagactactt cagatcgaaa atctgttttt   1620

aaaatcattg actgatattt cctttgtatt tttttctccc ccttccagga ccctatctgc   1680

agatgttctg aatacctctg agaatagaga ttgattattc aaccaggata cctaattcaa   1740

ggtattagct ctcgtcagaa agcttttaca tttgagctct gtgttggaaa ttctattttg   1800

gcaatgaatt gaaataggaa aagttggaat gagaataaag gacaaaagtg aatttgcaaa   1860

ataatcaagt gcttaaaaaa ctacccagca cttgtgaggg tttgctattt ctgactcatg   1920

tgcaaccctg tctctgccag cttatgtgcc aatactgact tatttgtagc cctttctctg   1980
```

-continued

```
caactgtgct tggagtttgg atttcatttt agtctcaccg tctccgtttt tctctgactg   2040
cccagaactc cagaaatcag gagacggaga cattttgtca gttttgcaac attggaccaa   2100
atacaatgaa gtattcttgc tgtgctctgg ttttggctgt cctgggcaca gaattgctgg   2160
gaagcctctg ttcgactgtc agatccccga ggttcagagg acggatacag caggaacgaa   2220
aaaacatccg acccaacatt attcttgtgc ttaccgatga tcaagatgtg gagctgggtg   2280
agacactgga ctcttcactt gttagtctct tttgttcaga tgatttctcg agtctcagga   2340
ttatcaggag acattctgag gctttgcact taattattgc acattaacca acaccctagt   2400
ttacgcaatg aacttgtatt gaccataagg catttggttt gtgtttcagc attacttttc   2460
tgatgttatg cttttgaaat ggtcggggaa ggggcctggg ggagtaggac aatggagaaa   2520
gagggtcagc actgaagact gtagaaggaa aggattgaaa gccctcagtt aagacattgt   2580
aaaaatattt gggcaaagtt gtttcaaaga gtatgaggat gtgactgtaa ttttatgcaa   2640
tggatatgaa tatagactga tactaaagga actttcagtg gttattagta ttagagtgga   2700
ttacttattc acagtttgtt atagtaattg ttaggtaatt caaagttgca gtgttctata   2760
tgtcttttgg tagagaatcc acttactact accttagata tgatgctttt ttatttagct   2820
tgcctaggct aagcgtagag cacccagaaa gcctgccaaa atctagtgat tctaacttac   2880
cttctatatc acctgactgg gtttcttacc ttctcaccgt cttcaatggc ccagccctac   2940
agtcttgttc ataagccaag ggccaattct tctagtccac ctagtgcaag gcagatagaa   3000
agcttgcccc tagaagttgt cactaccact cctcatttct tttcctgaac ccaaattcct   3060
tgctctcagg catcacccag ctgtgcttag ccatcacatt caacctgact ggtagttgaa   3120
tcttctagca gagcatgctg ggcttcttta ccgagctcct gaggctcagg ttcttgagga   3180
taaaactctt cacgctggca cttggtctcc atggaagggg actttgcttt cccacttgaa   3240
accagacggt gagatcccag taaagttaat tccttgggtt cagctggaag caaatgcgct   3300
aaaaagccag cagatgtcat tattgctgac gttggtttga ggagtcaacc caactttttt   3360
ttttttttaa caagggtatt gattttcagg cgacaggcca aaatgaaagg tgtcacacat   3420
acatgagtgt gtatttagca catatgatgt tagtatgtat gtaagtggtg gtttaaatgt   3480
tttcattcac ttacagagca agtaatttta gctttttttag agccttgtgg gtccatttca   3540
agttagttta gtgcctaatg tgttaatagc acagtctctg catgaggatt gcaatgttaa   3600
acatatcctt gccctctgct tgacctcaca cctgaactca ccttccttaa tatctcaccc   3660
atccatcgct tttgctacag ctgagatctc tggatcctct catctttccc agtttttccc   3720
tcaccggttt gtcacctggc ctgcctgcct cctctagtct tggcctctct tgcccaccct   3780
tcactcaatt gccagagtta tctttcaagt atctctctga tcagatcact tttctgctta   3840
agtcccttct gtggtttccc tttgccatga gattatgccc ttctcctctg tgggcaaatg   3900
agttctgagc cttgcgaccc ctgcctgtcc ccaaggctgt ttccctttcc tccactttca   3960
ctctgtgctt cataaacaca attgccatct ccccaaaggt gtctggtggc ttcacccccc   4020
tcgcctctat ccatgccttt gcacatctca tcccctctgc cttttcctct ttccccacct   4080
ggagaaaccc tacctgttct tcataaccca gttcatgtca tgcgcttggt gttcccaaaa   4140
caaaaccacc ctcccctcca gcagcattga tggaactttc ctttgcaccc cgagaacacg   4200
actccagcat ggtgctcatt ccaccatagc cttccatgcc tgtcccttcc acttgaccaa   4260
gatcaaccag agagcaaggg tgtgttttat gttgcactcc tcatgcactc ctagtgcctg   4320
ggaatatagt gggcactaaa ctaacttgaa atggacccat aaggctctaa acaagctaaa   4380
```

-continued

```
attcccagaa ataaatataa gtattcatca tcatctacct cttcaatata cagcactgtc   4440
tttaaaatat attaagaaat tgctcataac tttctttttt aacagaattc aaattttcag   4500
ccttgtccta tagttcattt attcatccag taaatatttt ctgagcagtt accaagtatt   4560
gccttctgtt ggaggcatgt gactatcatg gtgaagggtt atagaccagg ctcagccaac   4620
ccagatattt cctacatatt tgcctttaac tccttccttg attttctagc cagataacat   4680
gctaagaact agctcattgg ctgggtgtgg tcattctcgc ctataatccc agcacttcgg   4740
gaggctgagg caggcggatc acctgaggtc aggagttcaa gaccagcctg gccaacatag   4800
tgaaaccccg tctgtactaa cagtacaaaa attagccagg catggtggca ggcacctgta   4860
atcccagcta ctctggaggc tgaggcagga gaattgcttg acccgtgagg cagaggttgc   4920
agtgagccga gatcacacca ttgcactcca gcctgggcta cagagcgaga ctccatttca   4980
aaacaaaaaa agaactagct tgtttaactc tcacagtaac tctaggaagt agttactatt   5040
ctctctttaa tttaggtatg agaaaaatga ggctcagaga agtcatgtag cttgtggtga   5100
gcaagtaaat tgtgaaaccc agacctgtat tagatctgag tctccacagc tacgtattta   5160
accactgtcc cttccattaa tcagccatct acaaataatt attaagcacc tcctaaaaac   5220
aatcggcaaa ttcataatat tttaggttct gggagagagg gaacagaagc aaaagatagg   5280
ccactggcaa aaacaaaatg actaggaacc acagtgaact gtgggttgga ggtccagaaa   5340
agacctcctt tcttggcaga aaagtcatgc tctcggtagt ggttcccgct tgatggagac   5400
ttttcctcat ttttctgtaa tgtgctcata atccttctag aacattattg ctctagattt   5460
tgggtgttgg ttgttttgtt tttgtttttt taccatctta accattttta agtgtacaat   5520
tcagtactgt taagtacatt tacattggtg tgtaacccat ctccagaact ctttccatct   5580
tacaaaagta aaaccctata cccattaaac agcaactccc gtttctctct ccctcaatcc   5640
tggcaactat cattctactt tctgtctctg tggatttgac tactctaggt atcttatatg   5700
ggtgaaatca tacagcattt atctttttat gactggctta ttttacttac cctcatgtcc   5760
tcaaggctca tccatgttgt aacatgtgtc agagtgtcct tcctttttaa tgctgaataa   5820
cttttcattg catatatgta ccacattttt ttaacccatt catccactgt tggaaatttg   5880
agttgcttcc tccttttccc tattgtggat aatgctgctg tgaacatggg tgtacaaaga   5940
gctcttcgag accttgcttt tagttatttt ggagctatac ccagaagtgg aattgctgga   6000
tcatatgata ctcttatttt tattattttg aggaaccacc ttactgttct ccatagcaac   6060
tcaccttgtt acgttccctc caactgagca caagtgtcat aatttttcca catccatgcc   6120
cacacttgtt attttctggt tttgttttta atagtagcca tcctaatggg catgaagtgt   6180
tatctcattg tcactttgat atggttaggt tttgttttgt tttttactcc agtgcaattt   6240
tctttgccaa gtgctttaat aaatcttcac ctaatgcaaa cctttttgca cctgtaatgc   6300
tgtaggcaat tttggctact gtgcctccaa aaagaaagta acagacttag taaagactta   6360
gaagaacaat tatgaaaatt ctaatagaat acttttctca ctgggaaagc ataaaacaat   6420
cctatctgtt tatctagaaa gatgaaggct gagaagggct ataatcaaag tttataaaat   6480
cgagccaggg aggaaagtac tagttcatta tgagcaggag cccttccctt cactttcagg   6540
acaaataaac tattactctg taaagggagt aagacacata aggaattcat taataaaagt   6600
actagaacct tgcatatgga taacacttta tcttttccca aagaacattt tgttcacatt   6660
attgtgaatg aatattgcca tctcacatga gttgggtggg taggacaaag atcatcatcc   6720
```

-continued

```
caggaggaaa cagcctgtgg aaagatgaaa tggcttaacc atggtcccct tacttctgaa   6780
tttgcttttc ccacaactta agaagttgtt cacgttgtgc ctatacccgt aagtacttca   6840
gagttttagg ctagaataat gggtggaaga tttacaattt tttaagctaa gtaaacacgc   6900
aaggaagtga tcaacataaa gttcaggata atggctacca ctggggaaaa agtgatgacc   6960
gagagcatca gtacattcac attctatttc aaaactgaaa aaatatatat ctgaaagaat   7020
ataatcatgt taagttttgt taaagctagg agatgcgtta tttattctgt tacaccctac   7080
acttgaaata ttttataaat cagaaggaag aaaataaaaa atgtttgagg gactcctaac   7140
tttctgagcc tagcatcaaa gaaattgggc tctaaatctt tcccaaatgg cctttggtgc   7200
tagtctgaga aacaaaatac tgagcagaat agaccattga tctgactcaa catggcattt   7260
cttacattcc taggaaattg acctgacagg aacatctcag taacattgac ccgatgtttc   7320
tcttagatca tatgtatagg gaagctatga gtacatggag atattttgtt tctttaaaac   7380
aaaagccaga acacaagata ttcagaccag agctagccca cagatgtatg ttgtttgatg   7440
agcatacttt tcagaattaa gccaatattt taaaatcata ttttaaaata tatataacat   7500
ataaaaaaat cagattctga cgtttcttga aaattcaaaa aatgaaggct tgtattccca   7560
tgaagcagtc atcacttgga tgtttgaagg ggagctgcag ctgctctcgg acactgggga   7620
tcccccacta ctgtgttgtc cctcaataac ttatgccaag gtgcaggtgc catttatcat   7680
tgaccatact gctgtttttc ttatagtcag gaaaagctct ataaaccatg tctctatcaa   7740
aggtaaaaca acaaaaagac acaaaaaccc tctgactttt cttatacctg gctgccttca   7800
cttgcctacc ttatctatgt agccctgtag gcatgttaac ttccattcct gtaagtagct   7860
tttaatggcc ttgtgctctt ttggaggggc caggaggaaa tgatgagtct tagtgatctg   7920
gaaacattcc agactaattt attatcttct ctttttccc ttcttctccc aactaccttt   7980
tccccctttg gttttaggta aaaaacatct tttttttttt cttgccaatt ccatagtttg   8040
ggtagaaaaa aaataccatt taattttgtt atttttata tgcttatgct tttagaatta   8100
gaatattcaa tagatcatac aggcatttta ataaaggaaa tgtcactgtt tcatgtttca   8160
tactttacta tgaaaataac tgttggcatg tgaaaatggc agggaagtac ctaatacaaa   8220
cgacttaaat atttaaagca ttagccttac ttcatcataa aagaatgaca tcgacaaaca   8280
cccctccaca atcagtaaga gctgggtttg cttgttgttg tcaatcttca aaccatgaat   8340
gctctaatcc acatggaagt atctctctag gaagccaggt gtatatgaat cccacatgtc   8400
tgggatttcc ataagtgata atgacaatat ttactgttga atttctggtt ctgcgagttt   8460
ttctggacat gacaaacagg tttgatgaaa tttttaatgt ttagtaatac aaaatactgt   8520
atactcaaat gctaagatat atgtatcggg aaaggtaaag ctttgttttg aagtttaaac   8580
atgtcaatga agtaattcag gatctccgtg tgattttagc aaagtcatcc aaattagggg   8640
gacattttct ccgatccttt ttcatacaaa tgatttttgt atgaaatcat tctgtatgaa   8700
atgattttgg gaatcaagta gttggagtat ataaagtgat ttaaattcct cactatggtt   8760
ctgtctagcc acaacctatc acatactcca tccaaagcac tattcctgga gctttgattt   8820
ttaactgtgc caaaattgcc aacatggtgg atcttgatgg attcctgaag ggtggcactt   8880
ctcccactcc cagccaccgc tgacctcttc agcatcctgg tccacagccg atggctgtca   8940
cagcatccgc ctgcaggagc aatggaagat gttctcagtc ccagcctgga actggggcac   9000
tgggacagtg tgtcttggca gtcctgtggc ctggaccttc cctctcatca agccagccca   9060
gtcagcagtg catgcacacc agctacacag acataatcac ggttgcttca gagcatttgt   9120
```

-continued

```
gtctggctcc cacttcatgg gacaacttaa aataacaatg aagttgggct ttttgcttag   9180
ggtgaggagt cagtgtgtgt agaaaaggga agaattgata tttgtatttg aaaaccaata   9240
tcaacatttt aagtcttaca gcatagaaaa ggtagttgac ctctgttctc tcctccagct   9300
tttggacttc agatgtagat tacagagaag aagatggaag aggcaggaga aaatttaatg   9360
tgatggggtt gaggtgagca catagggcaa ccacagccac ctcggcacac tccttacagg   9420
aagtacttga tggcatcctg ccgtttgctc agcaacaacc ttgtaaacta gtcggagtgg   9480
ggagcgctat tagaagctcc attttacaga tgagaaacac aaaccaaaaa aggataaatg   9540
acttgctcag gctaagctgt ggcaaaatcc aaatgttttc ccacatgttc aagtctaggg   9600
ctctttccct tctcatcttt atcatcctca cccctgcctt gtgaatctga ttatgagtgt   9660
tcagctttac aattcatatc attcctatga aataattgtt gtaataactg agaatcagca   9720
ccgtttgcat ttcaggcacc caaggcctga aacctacaga agtgaagagc ttcagcttaa   9780
aacaaaactg agcccttcca cttatcggac agacattgtc ctgtccactg ctctcaacag   9840
ctgtgaataa ataactatga gttttattac agaatcattt ttagtaaggt ttgccaataa   9900
aaaaatcaat ggcacaatca cagtgggaat atatacaggg taaggcagtg ttattgactg   9960
acattaatca ttgcacagcc attaaaaggt gctcgatgct ttccttactg gtacacacta  10020
acacagtgga gtgaagagat tcagattcct gcacaccgtc atctgtctct acccagagaa  10080
tccatagaga tcagaggcaa caattaacgc caccatggca gtcagcagct aaagacagac  10140
agatccacag cccactcatg cctcatctgt gcctgagcca ctgagaccat ttcagccttg  10200
aggggagggt aggagacagg tgttaatgtc agtcagtatc tcctctaaga ggcgagaaga  10260
atcaaaagat gagagtgcag aaagagagac ctatcgcgac tgcaagcaga cgtcaattct  10320
gtttctcatc ttgaaaatgt caatgtcaca gccagcattc agcctagata gagctcaaga  10380
gcatggtctc tgggaagact gcctgcattt acttctgggt tctgctactg agggtctgtg  10440
tggccctagg cacagcatga tttagccttc tgcacctcca tttcattatc tgtgatatag  10500
gaataatagc tgctagcacc caccacaaag gattattgtc tggatcaaat taattgctca  10560
tgtgaagcac ttagaagaga acctggctga gagtaagtag aaaatcgatg tttctttttc  10620
ctgtctacaa tataccttat agtcttggca gtgatctaag ccacctagat cactcaaaat  10680
taggcaccca ctacagtctc ttccagctct aggcttccct gattctgtgt ccaacctaga  10740
atactttttc aggtgagatt cactgagagg cagcttcggc ttcacccagg tttcattaga  10800
aacacaaatt ctcaggcccc atcctggact tactaagcca gtatcttggg gtgggtacag  10860
gattctaggg cttattatgc ccttcaggtg attttttaaa gttggacaag cattgtctca  10920
gaatctcttt actgagaacc ttcaagccag attcccactt tttgttttgt ttttatgaga  10980
cagagtctcg ctttgtcccc caggctgaag tgcagtggcg cgatcttggc tcactgcaac  11040
ctctgcctcc tgggttcaag caattctcct gcctcagcct cccaagtagc tgggtctaca  11100
ggcgcatgcc atcatgctgg ctaagttttg tattttcagt agggacaggg ttttaccatg  11160
tcggccagac tggtcttgaa ttccccgcct caggtgattt gcccaccttg gcctcccaaa  11220
gtgccgggat tacaggcatg agccactgag cccggcccga gattcgcatt ttcaaggacc  11280
ccagtggtgg agctgtattc ttaacagtgc ctatggggat ccactgttgt cttggttcct  11340
tttgacgtgt ggactggtgg gagccagggc atctggaggg attgcttggg agccctacac  11400
aatcagctca gttagttaag aaaaggatga tactgagaat gagaggagaa tcctagctgg  11460
```

-continued

```
ggcacttcca gcagtgatga attgggataa gttttagccc ctgtttttat attattttga  11520
ctttaaatca gatttctacc tcggtcccat atttgtagtc taaatgagtc tgtaaactag  11580
agattacagt gctgcgattc agaaccttgg atgatggcct cagctgcatt tttcttttat  11640
ttgaattctg ctaaggctca taaaggaaac tgggagcttg ttctttgaaa tagactactg  11700
gacactgaaa agccatcaac agggtttgct gttttcccca aaatcaagat actcagtaac  11760
taactactgc agagatctaa agaggagcaa tgagacatgg tagaaatctt cagtgtcacc  11820
tttcaccctc tttccacttc tacatctccg ttcatccact tatctccagg atattccccc  11880
tgtgtgatca accaacacaa atataaaatg caacatttct aaaatggggt tttaaaatct  11940
cccataaggc atattccttt ttagttactt cttcaccatc agtgaaacga ttggtttcca  12000
gttttcttct cacggtgaaa acttcaaggt gttagccaac tcccagcctt ctcatgcatc  12060
accacatcac ttgggtctgc ttcttagggt cgctctgtgt cagaggcata gtcgtccgag  12120
ttcttctttc ctcaggggta gacggcttca gcgacctcat ctgcaccctt cgtggaccag  12180
cagcagtgtg ccctcctcaa tccacacacc accattgcaa ctgcaacgcc tctcgagggg  12240
attgcaatcc actgcagcag caacacctta caaagacttt tttcttaaca tgccgttcgt  12300
gtctttgaca cagaacataa ctctaccttt gttttttta ttctatcaca tccagtatct  12360
ctgcccagcc ttcaagctat ttgctaaatc tgctttccac atttcatgaa gagaattctc  12420
catatttctc ttcatgccag gaaatcaatg tgttgttctc atcactctac ttgtttcttc  12480
ccacctccag agcatcacac atgtcactcg ctgcaatccc ccaatgatat acttcaccca  12540
tccgacattt acttcctcct ttttttccat ctgtcctcat ctctcatttc agaactctta  12600
ttaagccatc aatccaagtt ccctctattt ttatatgccc tgctactgct gtattcacat  12660
tgttacgtgt gcattgcttt gcaaatatcc ccaagtgatt tttctatgta ggttctcctc  12720
tagagaattt attactgaag accagaggca gaaaatttcc catttctttt gtttatgcta  12780
cacttgggag atcagcccgg aatgctgagg ttgatagaat gttttgcatg aagtaggcac  12840
tcaagacatg ttattcattg actacaaaag gttgcttgat gccctgaaga caaccagaag  12900
agaaagagca gttaggattg ctcctagccg aggcatattt tagggagctc taatgagacc  12960
caattagaaa ccctcctcct gttctcatat gcgtcatgtg gaacggtaaa agctagtata  13020
tgaagacacg gggctaactg tggctttttg gactgttgca tgcttctctt ctgccctgaa  13080
tgcttgcctg gtttgcatta cgatttcctt ccttgctgga aaacatagac tttcttcctt  13140
tctttggaag aagtgggacc tgttggaaat ctgaggctcc aagattcaaa tgcaatgggc  13200
ttggctgtag tgctctgtag tacacttctt gacaagtcct gaaaagacta ttgaattctg  13260
gcctgtgctt ttctgcagtg tttggatgtg tttcagctgc agtgtttggc tggacagagt  13320
aatcgaaata gttttttttt ttttttcctt cctcagcaat cttacgttac cagttgatcc  13380
ttaaagttaa aatggaatat tttacaaccc tgcaaatact ttcgagtgca atcgaattat  13440
agctctttca caagcaaaca gcctatcttt aaaaaattgt gcataaatag gtcaaaatat  13500
aaattgatgt tgttatccta atagaaaaac tggcaaacat ttggtgagct tgctagagga  13560
taccaacttg cattgaagat cttttttaat tattattaaa caaacacagg cattttgatg  13620
ggacttaata tggaagaaat ttttttctct tttctttcat acgattaaaa tgctatagta  13680
gtaatctaca ctagtaatct agtagcaatg tcactagtag attgcatttg tgctgggctg  13740
ggggttttga tgctctgtgt atcaggctat tgttctctgg taatcttcaa agggctgctg  13800
gcctttgaat ctgctccata tctaaaattc tagctttaat tatcagatta gcctgcattt  13860
```

-continued

```
tttttcttc gtgattacag ggaggagaag tgtatgttta ttattctgca aaatacttga  13920
gatggtagga tctcaaatgc ttaattttgt tgtagaaatg agagctgatc aaattataga  13980
ctcctttaag ctaaggaaag gaaatgaata agtcagggaa acagaggcac tgaggggcac  14040
aatcgaaata ggcattcatg tgctgcactt tgctaaacaa tgctggcact gtgcctttca  14100
gggtccctgc aagtcatgaa caaaacgaga aagattatgg aacatggggg ggccaccttc  14160
atcaatgcct ttgtgactac acccatgtgc tgcccgtcac ggtcctccat gctcaccggg  14220
aagtatgtgc acaatcacaa tgtctacacc aacaacgaga actgctcttc cccctcgtgg  14280
caggccatgc atgagcctcg gacttttgct gtatatctta acaacactgg ctacagaaca  14340
ggtaagggat gacgtttcta gcccatgaac gtcttgtaat atgtcttaga ctcaggaaga  14400
agtgtcatgt aatgaaatgc atgaagttcc aacaaatacc taaaaaagga tcaagtgttt  14460
ttaaactgct tgacatctac cccagggtct gggacacagt aaatgatcaa aattatttat  14520
tatttattaa ttaatgaaaa actgatgggt aaatcaatca tgtgtacctt gttgattcat  14580
gtatttgttc attcataatt aataggattt ggaaagtttc tttagcttgt ggttgttttt  14640
aggtctcaaa tgttcacttc taccttccag gaaaggaagt catcctaatt gctacacctc  14700
ctattattgt ttaacctaca cagggcaaga agaggttttt gattaattgg tttttgaaa  14760
attggggact tctttcaaga ggggtagtga acatcatgcc agtctttctg agaaaaaagc  14820
aaggttcctt ctggtaatat tagccccaag gccctatcct cccagcatgt agatgatgtc  14880
cttgggtttt ttgtagcatt tcttcataaa agggcacaac gttgttcgta gaagggctac  14940
agtgcagaca tgggttgttg cttgttttta tttttccaga atcacctagg cttattcata  15000
agaatcaaat atgttatgat taaagcttgt tcaaatgact ttcaggccta caatttctct  15060
attttgaaga tttaaaagta aaggagttca gataaatatt ctcctgcatc tcttttaaaa  15120
gtgaaattaa tctttcccac tggactcagg aaatatatgg ccatttgctt ctttgcagag  15180
cgccctacgg gcacttaata cttgttattt atggatgaaa atattgattg tgcatatgat  15240
agcactgtca ctcgcagaca gctcaaagtc tcgactcgaa gcagctcctc ccgtgcatct  15300
caagggtgtt ttcttatgcg taggaaagaa actaggttac gtagaggtta cagagagtgc  15360
cttatctgag tgtgttttct cacattagtg atttaaattt atagcacctt tcatttgagg  15420
actctaaagc aatttgcaaa tccaccaaac atccctgtag agttcataga tggcaaatgt  15480
acttggctct gttttataac tgaggtgggg atttcaaata ttgcgtgacc agctcagaaa  15540
cagaatcaga ggcggttccc taataaccgg ttcctgattt taaccatcaa attgtgtttt  15600
gcttctggga agtgttgtgt gaaatcagtg cctttcacct cccaggttcc ctagtagcaa  15660
acatggaact ggaacgattg ggactctcac atatccagag tgaaatggat gacatttgtc  15720
ataagaaata gagattgagg gtgagacagg gccctgccag gacttagagc agtcaactag  15780
ggtttgctaa tttgtttcag ggctaaatta ggaagggcaa gaaagaaggg aactccattt  15840
tgccattatc tcacctaatt cctagggcaa tcttgaaaga aaggaatttc ccatgttact  15900
aatgaaaaaa ccgagactca gaaaggctaa ttgtctatgg tcatgagcta gtcggtgatg  15960
gaatgaaccc agcacatctg actccaaagt ctttcctctg ttcattgtct tatttattta  16020
tgtaatgatt ctcttctgcc tcattccaaa acgccttcca gagatacaga ctttagaagc  16080
tacagaccca tgaggaccct ggcaaacaga aacaaagagt aggactagct aaagtcaagg  16140
caaagattgc tgtacaaact gcttgctgtg gagttgtagg gaaaggtgga atatttagaa  16200
```

-continued

```
ctaagcatcc agatgttaag agcaaaaatg gaaacaccat ccattgtaaa gttcacccag  16260
tcaccgggat aaaaacaatt cagttgcctc taagcatgtt tcctggtact tgcttcggtt  16320
atactgtgct atatccacct taagagggat tgagagagtt taactaaaac tcaaagatga  16380
tttagttcca tttccttatt tttagaggag caaatttaca cccacaagaa taaagtgact  16440
gaagtgacag atctgactgt tttttattta tttgtttatt tattttattt tattattatt  16500
atactttaag ttttagggta catgtgcaca atgtgcaggt tagttacata tgtatacatg  16560
tgccgtgctg gtgtgctgca cccattaact cgtcatttag cataaggtat atctcctaat  16620
gctatccctc ccccctcccc ccaccccaca actgactgac gttccaatgg gaagagccgg  16680
caccgggacc ttagtcttca gggctctctc cagtgtgctg atcaaacctt aagaatcggg  16740
tctgggatga aactgtgtac acaccggaag gcttccctgt tacctcaatg gactgtcact  16800
tttttgtgca gcccgagaag tttgtttcag tcgatgtctt ctccagggag agtagatttg  16860
ctcctggaaa ctaaatctgt ttctaaacct tttccccagg gtttagacac ttaggtaata  16920
atacaattta tagtgagtca acctccaaaa taaaaggaat tctttaaggg aaataaagac  16980
ttttccaaaa acttagttaa cagtaggaaa aggggctggg tgcggtggct cacgcctgta  17040
atcccagcac tttaggagga caaggctggc ggatcacgag gtcaggagat cgagaccatc  17100
ctggctatca cggtgaaact gtctctacta aaaatagaaa aaattagcca ggcgtggtgg  17160
cggacgcctg tagtcccagc tacttgggag gctgaggcag gagaatggcg tgtacctggg  17220
aggcggagct tccagtgagc caagatcgtg ccactgcact ccagtctggg agacaaagcg  17280
agactctgtc tcaaaaaaaa aaaaaaaaaa aaggaaagaa aaaccagtag gaaaaggata  17340
atatgggctc aggaaaacaa atctagattt gcctattagt aaatcagaaa aaataaaaat  17400
tggggccggg tgcagtggct catacctgta atcccagcac tttgggaggc tgagatgggc  17460
gtatcacctg aggtcaggag ttcgagcctg gccaaaatag caaaacccca tctctactga  17520
aaatacagaa attagccagg tgtgttggtg catgcttgta atcccagcta ctcaggaggc  17580
tgaggcagga gaatcacttg aaccaaggag gcagaggttg cagtgagcca agatcgcacc  17640
attgcactcc agcctgggca acaaagcaag actctgtcac acacacacac acacacaaaa  17700
aaaaaaaaaa atgggaagac tgaaatggca gtgatagaga tctctataat ttaatttatc  17760
cttgatggga aaacattaca gtatctcaga caattaggaa gtaaaaatgt cttcatgaca  17820
atagttattg atccaaccat ggacaacaac ccatttgaaa atacacaaat aagtacacac  17880
aagtggcagg aatcttagaa aattaagaga attggtaggt agatattaaa ccaatgtaat  17940
tatgagacac taaactagta gggagaaagt caatgtgtaa agattctatt gctttcctaa  18000
taatgaattt attatttgga acatttagct acaaacctaa gaaaaataat gacggaaact  18060
gaaatatgta ctatacatac ataaatatcc atctagagag taagttttat gtagaataac  18120
tcagagaaaa caaattacta aagggcttat tttgggaggc gtccagaatc catggattta  18180
aatgagttga attaatccaa tattatattt accattgtat gacatgagtt ttctctttca  18240
gaactgaggc atatttttgg actggctata gcctaaattt ttctaagttt actcatggaa  18300
aatatgagtc tatgagagct tgaatgttca agaaggggaa aatgcagtaa catgtcgact  18360
gcacttcata ttctgacaag tgaaatagga atgagattgg attatatatc ataaaaatga  18420
ttatcctgcc tgaaatcagc tccaaaaaaa ttaacttaaa tttattatga ggatatcaac  18480
attaatataa aacctggctt aggttttaag gtaaaaataa ttatccatgg ttgagtgata  18540
gcattaagta tttaacaaca acaaaaaaaa ctgaagcaag attgaaaaca tcgtggaatc  18600
```

-continued

```
acattctacc ttgatttgtt ttgaggactt ggactggcca gttttccaat ctgtatgatg  18660
cagagattgg cctagaatga ttcctaagtt ttctttcttg tccaaagtta cagtgtgtta  18720
taactttatt atactcatgg taattataat attgattcat ttaacaattg tggtatttga  18780
attataatcc taacacatgg tacataaaat cacatatgag ttaaatctta atcacatgaa  18840
ttctacctca catcactgag gtagaaggga caatatttaa tagacagctg caataaatat  18900
ttttgtgaag aattcttttg tcataaatca aaatcataga ccttagttct gaaaaagaaa  18960
aattatatca aataatggta aatacaatat tggatcaaaa atttttttgt ctttttacgt  19020
tacaaaattt atgttactta tagcaagtat atttattctc taatatgaga ttttttaaat  19080
gtagagttca cttaaagtaa gacaaactaa tattcttaat tttattatga tgtagattct  19140
tgatacatgc ataaacatga gaaatgtcat acatttatta aaccacagtg tgcttggaac  19200
acactagaca ttgggatgaa gacatttaaa ggaagattcc tgtcttcact agacttacaa  19260
tctagttgag gaaaccagac tgctgtatac aaactgacat taatcataat tttaacttgg  19320
ttcaaaatta tttatattta tagttactag cgtgaaatcc atcaccctaa gtctatcaat  19380
tacgtggatt aaaatctcaa tatatctttt gatacattaa ataagatttg acttttctgc  19440
ggcatcagat ctttgggtta gtcactattg ctggctttaa aagaaattcc ttggcttcag  19500
gtagttcctg gaaatttttc taagcattat ggaacaggtt gtcctagaca gaagtagcat  19560
ggcctgaagc caacaataat tacaatcagg tcttctgatc tttctccctg ccccccaacc  19620
cccaccacct tcttaaacag ctgtgaaggg aagtgcttaa tggtatccaa aacaaagagg  19680
atgggtaaat ggcacattag tgatgtattc agatagtagg agttgaattg aattgccaat  19740
gccgaaggat agaaaaatat tgaactatac gtaacctaca tgtagacata atggcagtaa  19800
gggcaagaaa gctaaattca ccttaggaag ggaaaaagag atttaataca tctggaggaa  19860
aataattaga aggccagata atcaattgca gagcgccgcc aggaaacatc gtgttgaaag  19920
aggccggggt gattacaaac gagtctcaat gtcatgaggc aacaaaaagg ccagagcaac  19980
tggaggccaa cagtgctgca ccctgacacc caaggccccc atcagccttg gaatgagtgt  20040
gatgggtgag cgcacatctg gaatactgag tacatttctt acgctccgtt aacacagaga  20100
caccaaaaac ctggagggag ttctgaagca aataacaagg actattaaaa gacttgaagg  20160
aatagtttat aagggaagga ttaagtcaaa ggggaatgcc atggcaatgg gtagaaaaca  20220
gtacaaaata tcctacaaag taaaacaatg aggaaagggc aggaatgact tggggagagg  20280
aaacaaaaaa accccaacaa tgaagtaact taaaagtgca gaaaaaaaaa ttaaaactaa  20340
ttaagcagaa aaatgtaagc caaatggagg agtttgttgc cacaaaataa gtagtagtgg  20400
ggaagaaaat atgtaacctc cgaagagata ttttcaagtg cacaagtgca gaactctagt  20460
gcgagatttc cttacactgc aggatggaaa atcatttaca aaagacaggg ccaaaagaat  20520
actgctaatg gtgatgctaa taacaatatt agttgtagga gcacttaaca agccgttgtt  20580
ttgtgccagg cactgttttc agcgctttac atatgtgttg atgcatttaa tcctcaaaac  20640
aatcctgcca ccattattat tatcaccata gtggctttgc agaaggggag ttgggggagg  20700
gagaagtgaa gtaacttgca tgtagatgga taccctagca agtagcagag ccagaatttg  20760
aacccaagca ggctggctct agggtttata ttctcaatca ctatgctttt tgccttcttg  20820
gaaaaaaaaa aaaaaaagga aagaaaagtg ggataaaccc gtagggatga ggaggaggcc  20880
aaggaaagca cggggcttga ggctgttaag tgcaagcttt ttggaaacaa tcgcttttga  20940
```

-continued

```
acgttagtgg ggtgtggcct tggtctgctg cctgtggctc caagtcatac tgcattttgt  21000
tggaaaagga aaatcatctt gtggttctat gtgaaaaggt cagttcgtct ctaagacagg  21060
aattcctcat taaaagaatt ccaactacac gtagtcagca cagaaggaaa tcctgagtca  21120
cctgatgtga gaccctttga cactttgccc tacactgatc aacgtgctca gtgcccctgg  21180
cagaatgctt aagcagcggg cacttggctg actgtagacc taattggttc actcattcac  21240
agagccaaca aataaacatt cattcaacaa acaaacattg ccatgtttct cagactggag  21300
tctagattct tttaaaaata atataataag aaataacaat tttagaaact ctaaagctct  21360
attctatgaa aatgttttga aggccaaatc agctttaaaa aatatgatga tttgattggg  21420
cgcagcgcct catgcctgta atcccagcac tttgggaggc ctaggcagat ggatcgatca  21480
cctgaggtca ggagttcgag accaacctga ccaatatggt gaaaccccat ctctatttaa  21540
aaaaaaaaaa aaaaattagc caggtgtggt ggcgtgtgcc tgtagtccca gctacttggg  21600
agtctgagac aggagaatcg cttgaaccca agaggcagag gttgcagtga gccgagatca  21660
caccactgta ctctagcctg ggcaacaggg taagactcca tctcaaaaaa ataaaaaaga  21720
taattcaagc aaaatcacaa aatttttaaa gtctagacct cgtaaagtcc ccagaataca  21780
ttggattcat gaacccaaat tcaagaaaca aaaaggatgg agccctgaac tgtgtgcaag  21840
gatggagagt gcctcagaga taaggcagag gcaatgtttg ccctcaaaaa gcttacagtc  21900
tagcaggtgt tcagcttcta tatgaacatg actataccac aatggagaaa gggaagatga  21960
cattacaacc acaaagacag tgttgtggaa ttaagacaga gactgtgagt gaaatggcat  22020
ctgctctggc cttgatatat aaagaggcaa ataaagagaa ttgcacaagc aaaaatagag  22080
aggtgggaac cagagagcaa atagaggaaa cattagctgg agagagggac gattaacaga  22140
gaaataggag atggggttgg aaagggaagg attttgtcca aactcaaagt aggcctctga  22200
gggcaagcta gcagagtaca cttgattctg caggcaatga gggtaatctg agattgcgag  22260
aagagggtga agtaaccaga gcaggtcctt gggaagatta accagtggca atcgaagtgg  22320
aaagaccctc catcctggct gggaaagtca gtgagaccat gagcatctgt gaggggtggc  22380
aagttaccag ggatggcagg agggatttga gcactatttc caaggcagac ctgataggag  22440
gtggcaactg cccagcaagg ggagcgcagg agcaggcgaa agcagagggg gctctggagg  22500
gccaagcatg gttcatggag ggtgattatg ccattcagag gaatggagta aggctgaaag  22560
ggaaaactgg taattccatt ttaggcaatg gcattaggaa gcaagtaaaa cattcagatg  22620
gaggaattct acaggtacag gtgctccttg acttacgatg gggtgacatc ccaataaacc  22680
catcataagt tgaaaataag gtaagtcaaa aatgcattta atatactgaa cctaccgaac  22740
accagagctt agcttagccc agtctaactt aaatgtgctc agaacactta tattagccta  22800
cagttgggca aaatcatcga acacaaagcc aataggcttg taataaagta ctgaataact  22860
cataggattg attgagtact gcactgaatg cataccaatt ttacaccact gtaaatgtga  22920
aaatcttcaa ttgaaccatc gtaggtcagg gaccatctgt agtcgtatat caaagataaa  22980
agcaagctaa atacctatcc catagagaca tcaaaattat gtacatcatt aagtttaaaa  23040
ttcagaatgt gtgttttaag accaatgtca ataaagtgct gcaattctag aattcgtttc  23100
tattatccca agccagtctt ccaggaacta ctttttacc atggatataa gcgagggcac  23160
ctataaaatc tgtttaatga agccaggcat tggctttgac atggaaggcg tctggcaaca  23220
gctttataac atcagaaaaa ctaaaacttg cctacatatg tatatgcatg cataggggtg  23280
tgtgtgtgtg tgtgtacaca cacatatata catacacgca cacatgctta tacctataca  23340
```

-continued

```
gacatatata aaataaagtt ttctctagcc ctttctactt gaagggaaag ctatgtgtgt  23400
ggctggagtg actaaacatt taggtttacc cagaatcatg cttgtttata cctgcttttc  23460
tgtaattaca gcaattacaa ataacatcct cttgctctct caaaagtatt ccagtatatt  23520
tatgactacc attctgctag gttgtaatgt ctttttcact tcaagaatga acccatattg  23580
ttcctggaat cccagcttct tctttgcttc ccgtacccct ctcctgtcat catcttttgc  23640
agaagaccaa atttctagtc accctctcag agagaccgag tcagccctgt ggcacagtgg  23700
tctttcttgg aagtgacatg ccaaagttat aaatgtgaag gccttccagt ggctttttta  23760
gtgaactgtg gtgtctttgt gacacataca cttctactat actataattg tatgaaaatt  23820
agtaatctat gtagtaactc tatgttgaca gaatttttat tatcgataat agatgtatac  23880
attcataaaa tacacataac ataaacaccc attacatact atacatgtga tataaaccct  23940
gaccatatcc cataaaaatg gagtttacca tggttccctg gtttggaaaa tttgtactct  24000
ctggatatgt aaaaacgaaa ataagctttt caatagtgtt tttataattc acaattctca  24060
aatagtaagt tagaaaactt atcacaaaga ctgaactttc agttctccaa cacctgcccg  24120
gtggttgcat tccaaatctc acgctacttc tctgattgtt ccatcaactt aacaaaagag  24180
catagcctga ttttactcca gtaggaccat aagaaatgaa tgcacccaga gtgctgtgat  24240
cattatgatg gtttcattga gctgtaatcc atgtacttgg atactacttc tatttatttt  24300
ttaaaaatgt gtttgtgtca ctttgccaaa ggattggagt attacactaa tgtcattttg  24360
gcattcacta ttacctaggg caacttttgt tttaccgtct ctttttcaag tcataatttt  24420
atacttatcc atttatttat gattaatcat tttacgtgaa aaaaataatt ctttttttccc  24480
actgcagcct tttttggaaa atacctcaat gaatataatg gcagctacat cccccctggg  24540
tggcgagaat ggcttggatt aatcaagaat tctcgcttct ataattacac tgtttgtcgc  24600
aatggcatca aagaaaagca tggatttgat tatgcaaagg taattttcag gcacttttac  24660
actgcatcaa tttactttgt gcataatggg gaaaagccat tttcagtgag ttaaactatc  24720
cacaagattg gctttctatg ttctcacaat gttagcatga gaaatgttaa ggtaatttta  24780
aactctaggc aaggaaaaga ctctcaagga acgctgcctt tgtgtagtga tttccctcat  24840
taggatgaaa ggcaatcagg ctttgatgaa agtatcatca agaaaatcag aattctctgc  24900
tctcttatga taatttttgt cctcccagtt cccccggacc caaccaagga cttgtccaca  24960
taatcaaatg ttcatcttgt actgttttac ttttcactgg gacaaaagta tattttgtct  25020
gtggcttcag atttaggcac aagcataaga gcaaataaat atgataatta aagtttgaaa  25080
aaccacattc cttgctttta ctcctgtctg accaagctta gtatacgtga caaggacacc  25140
ttccctatca cggcaagcat ccacaaaagt ctctaatgct atcaattcta ggattttcaa  25200
atcagttcag agaaactgaa atcaacatgt cccatagttc tttgaccagt gggttctagt  25260
tttgacttaa aaattcacaa agattttgtg atagctgact taagtttaaa ttttttttcaa  25320
atcataagaa tgaaggggaa aatatcttcg aatttagcat gcttatttgc caaaatatcc  25380
ccttcccttc cagccatacc catctcttct tcatttatct agaagaagcc gagaatctgc  25440
tctatctagc aacctctccc aacaggctag atcacttggt agaaatcgga aggagagaac  25500
ttgatttaat gttggcatat tgctgtcttt atgcttggcc tgatttgagc acaagggact  25560
tgatgggaga taagattaag tccagctcct ttataccctt cagaaaacaa tgaatgcaaa  25620
tgaattcata aacattgcta ataggcttcc aaactcatga aagttaaaag ttagcagaga  25680
```

-continued

```
ccttggaggc aaatttgagc aatgtcctca tttgcaaaga tgagaaaaaa gcattctaga  25740
gtggctcaac cactcatcct aggtcatatc cccagctgtg gatacaatca ttgcaagcaa  25800
atggtgcaga ccacgtgcac taattgtcac tgctctcctt tgctgtctgt agggatgctt  25860
tttcatgctc cttgttcaag ttattaacct ttctttccct gctgtcctaa agagagcaaa  25920
gtaatcaaga ttctctccaa atactaaatc agcgtaactt gttcattatc acagctgatt  25980
aagtgtcaaa gacaactgtg tctgaaaaga atatatatct ttttttagtg aggaaaagaa  26040
tgaaacagac actcccttgg aagaggaagg ggatagcctg tagacttgcc ctaacaatga  26100
catgcggcac acaccatccc tctgatactg cttttgcagc tgttctggtc cttaaatcca  26160
caacatgtga ttagccatgc ctggaagcct tcaacatttg caaatattgc ctaaacactt  26220
tctgaataaa gtttatactg gagctccaag ccaatgacac acacttaaaa gaagcaggtg  26280
gtttaagttt tcatcttttc tttccttttc attccatttc ctccctccct cttacagacc  26340
tgcatcagcc ccccctgact gtgggttaag tcattttatt agcaagtcag gctctaatcc  26400
cagcagctgt attgctttag ttgtgcaatt aacacagtat aatctgcagg aaatcaactg  26460
ctccctattc aagtgtttca agtaaattaa ctgatcaaat gttgcagctt ttccctgtgc  26520
tcctggattt tggccatggc tttgattact gattattgta attcccacag gtggattttt  26580
cgtttgaaga aaatatcttt tcttgtgttt atgtattcat gggcgtgtgt gtgtgagcgt  26640
gtgtgtatgt atgtgtgtgt gttctgcaac tgtaaatttg aagtgggcgt gggtgtttcc  26700
tgcccttaaa gtaattaaat tttttgccaa ggaattacat caatgaaacc tgagactgaa  26760
atatgtatcc ggtgtttcat gtgttctagt acttttatcg ccagattaat cattatcttg  26820
ggcaaacacg acttgacttt ttttttcccc attgctaagt tgtgtattac ttaaaatcca  26880
tttttcgtat gttaccaagc tagcaaccct agaaaacaac tggcagctga ttttctctat  26940
tatcgaaaat gttcggctgc cttgggaggt gcagccttcc ttcctgctgt agaccttgcc  27000
acttcgtgca gtgaattgct tctgaggaaa gcagttattc aaatgcgatc tgatgaatgt  27060
caccttttgt aatttttgtt ttgtgtcaaa tgtatgtttc aggactactt cacagactta  27120
atcactaacg agagcattaa ttacttcaaa atgtctaaga gaatgtatcc ccataggccc  27180
gttatgatgg tgatcagcca cgctgcgccc cacggccccg aggactcagc cccacagttt  27240
tctaaactgt accccaatgc ttcccaacac atgtaagtaa caaactcaac tctgcgacct  27300
gccgaacatg cctttccctt ttctcctcat cccactcctc tcctttaccc cgtttccttc  27360
caccctgcgt atccacaagg ctttcttcat gaaaggataa cttaagagca gaccacggaa  27420
caggcagagc cgctgagcct gaaagaaagc gccttatctg ggtggtttga ggaggaatca  27480
aatttccagc atttacaagt agctaaatag aaaggaagag atgcacatag agtgaatggg  27540
ggcaagtttt acaagagttt cctttcgttg tcttaaataa tattcgtgtg tctgatctaa  27600
taatgatgat gatcaaatag tatgcttttc atagctgcac agtggggacc tctggtctgg  27660
ttatagaaac atggatttat tttccaggcg aataccgtag cagctttgct gcagacgtgc  27720
aattagaatt cctgcagaag gcagcttgag tggcttgccc aagagggctt ctcaggtcac  27780
agctttaaaa taacctgatt tttttttttt taaagaggca ggagtcttgg agatgggggg  27840
tgggaaggca caagggagag ggctgatggc gtggagggat gagacagaac aaagagctgt  27900
cgtgtgccca caattctcac cagccaaagg tggaaaaatc tagatgcttt ggcagcaaag  27960
aacatgattt tgttgttcac tcagttgaca ccatttcttc ctaagctttg ccatcaatat  28020
ccagtcttcc acacagagca gtggagttgg ctctgtgtct gctgaaagcc tgaccattag  28080
```

-continued

```
ggagacaggg aacagaaaat tggtatctgt ttcctatatt gtgaaacctc caaaattggt  28140
tcttaatcta tttgtactta aatatcatct cttttcatcc acactggtta ttagccaaga  28200
ttccaggcag aaagaacctt acgaaaatag gtaagtaact atgcaggctc tctagttgcc  28260
ggtcactata catccctaga gaagtttttta taaaatgttc tcttttttttt gagacagagt  28320
cttgctctgt aacccaggct ggagtgcagt ggtgcaatct tggctcactg caacctccgc  28380
ctcctgggtt caaacaattc tcccacctca ggcttctgag gagctgggac tacaggcaca  28440
cgccaccaca cctggctaat tttttgtatt tttagtagag acgcagttcc accatgttgg  28500
tcaggctggt ctcaaactcc cctgacctca agtgatccac ccacctcggc ctcccaaagt  28560
gctgggatta caggcatgag ccaccgcacc cagccttata aaatattttt atttgtacct  28620
taatgtaact gattgactta tgactcctgg tcagtggtac acagatcatc tctatgatat  28680
catgtgactt agaccagaaa gaaggaggcc agagctgact caggacaaga actaacaata  28740
tgaagccagg gtgggttacc tactgagcat gcccaggaac tcagaggatg gaagtgtttt  28800
aatgcataaa atatcatcga caaatcatga aggttgcccc agcacctggg aatatagctg  28860
ggataagcca ttatgttttg gagtcaactc catgggtgga tatttaagct tctgaagatc  28920
ttcccctata tacaactctg cgagtaaatt catgaatgaa gcccatgtgt gacaagtggc  28980
tctccattat agctcactta caaatttagt agccaactga ttcaatgaaa ggaaaaagtc  29040
ctgcgggctt tttcaatacc cctgaacccc cctgttccca tttctgttga atcagaaatc  29100
actttaccta tctttgttgc attagcagaa acccagtcta aggtgacttc ctataactgt  29160
aaactttaca gatgttccct caagctggag gagaaggggt tgacaaaaca gagtgttttg  29220
tggctcctta aaagtcagcc tgcctttgaa gctttgaggc aaggtcctaa gcctgcagga  29280
aaatcagcct caggtcaaga gtttataaga gctcagttgc atggaatcag tactgcatga  29340
ggggaggagc ctgcagagtt ctcagggtct cagcaatagc tttttgaaaa acatctctgt  29400
gctggccagg cgcggtggct cacgcctgta atctcagcac tttgggaggc cgaggcgggc  29460
ggatcacgag gtcaagagat caagaccatc ttggctaaca ctgtgaaaca ctgtctctac  29520
taaaaataca aaaaaaaaat aaaaattagc caggcgtggt ggtgggcacc tgtagtccta  29580
gctactcggg aggctgaggc aggagaatgg catgaacccg ggaggcggag cttgcagtga  29640
gccgagatcg caccactgca ctccagcctc ggcgacagag ccaagactct gtcttaaaaa  29700
aaaaaacaaa gaaaaaaaaa gaaaaacatc tctgattcca gtaattaaaa attctatttc  29760
attccacgaa tatttatcag tgccacatgt gacactatgc agcccagcag ggatatagat  29820
aagcgtgagg aagacacagt tgctaacatt taaggacaga taaactaagg caggggttgg  29880
cacactggta cccacagtcc aaacctagct tgccaccagt ttttgttaac aaaattttat  29940
tgacacacag ccatgctcat tcatttatgt attgtctgtg gctgctttca caatacaaca  30000
gccaagtcga gtagttgtgt cagataccat acagcctgga aatactatct catcctcgat  30060
aaagtaactt tgccccaacc tctgctctag gggcaggatg ggcaagtgtc ccaatggcaa  30120
tatcaccaat agggccagaa gtgacaagca cagagcagac gttcgcaggg ctgtggagcg  30180
gggagggaga agccttcata tctttaaagg aaaccaggaa aacttcatgg accaaggctt  30240
caaagtgggc ctcaaaagat gggtaaaatt tctgcagata attgtttaga gattgggttt  30300
caggaagaga atatggcaag gacacgtggt cactgtataa gggaggcaat ctaagatgtg  30360
tcctagaaac tggagaatgg gctacaaaga aagcagcact aaggaacaat gctgcagagg  30420
```

-continued

```
gaaactgttg cagaatattg agggtgtcag tgagtttgta tgtaactgca agcagagagt  30480
cactggaggt tgggtagtaa caaaatagga ggtggctcag acatttccac atgcaaatag  30540
attcagtagt tcctttttag ttcaaatgaa ccttctattg ccttattag tgattctata  30600
aagtaaaatc tacacagtgc agagggtggc cttagaggct aacgagcctg gtttcctgcc  30660
tcagctgccc tcactgagtg taggggtgct ttctttaatc tctggaaacc tccactgtct  30720
catctgtaaa atggagataa tactaacacc ttgatgtgat gtcatgaaga gaaattaaga  30780
gaggcagtgt aagtaaagtc cccacataga gcctgggaca tacaagccac ttcataagtg  30840
tcaattctta ttgaaccttt ttattaagaa actaacaata ttctatcatt ctggacctac  30900
aaaagggcaa tttcatgtgg ctcaacttaa ggtttagggg aagcagtgag agaaatgaca  30960
acttgatgct tgtccattgt gacatgacag acctcttgac aagctaagac tcccattgtg  31020
atgagcctct cacacctggc cattccaatg gaacagacag ggtaaggacc aatctggact  31080
gtgttatctt ttccaggtgc aagtatgtgc tatgggtaag tgccagtttg gagaactccc  31140
ttagccacag gaaatgaaaa ttcatgtgat tgtttgaagg attcagcttc tctttgctgc  31200
taatccttgg gttttgtgca cctagaatgt ggtctcctgc aggccctgaa agccttgaat  31260
tcctggcatc tttgctgtga aggtctccct ggctgctgct ggaggaaggg gctggaagga  31320
gtgagtgtgt gcacaggttc agagttcagt cttcagacaa aaggagtgag ataaattgaa  31380
gacaagctgc cgatggtagt gcatggaact gctcaatgac cagcttcctt agcgaaaaca  31440
ttagcaacac attcaggcaa agggatgcga gaagttaagt actttgcaga aatatttgac  31500
aggccctgca aacactgagc aagaaaccat aggttctccc caattgcagg gatgcaagta  31560
acgtgaacac tttcctttcg gtcatcttcc ttggtggtca ggcatcatct ggatcacttt  31620
catctggcat cgggttataa ctacctgacc ctctcagact ggggtgaatg tatcatcttt  31680
ccaaggtgtt tgccgttccc aacaaagaga ggaagccagt tcgctattgg cctgttagct  31740
ttacaaacgg atggtagagc ttatgcttac caaggaagag tgaaagggga ttatcgacca  31800
cttgttgaca gggaaaatag tttaatcaaa ctgtaactca gctactcatg gccactgaga  31860
aatctgagaa agcctctgtc ataataacac acataataat cctagtatta gaaagccctg  31920
cgctctggct aagactctac tatacttttc agtaacttat ttccccagaa tctccatagg  31980
gatgcaattc cttcacccct gctttaagtt acttctctct cctcgcctca gtgatgtcat  32040
catatacacc tgtggacaaa agccgtgaca gggaaggaga tgccatttac gtccctggtg  32100
attctatagg aaactaaggg acctccttat cacccttcta tgaactatgc ccctgtcagc  32160
tttaaaaatt tgttgttgtt attccaattt tttttttttt gagatggagt ttcactcttg  32220
ttgcccaggc tggagtgcaa tggcacaatc tcggctcacc acaacctctg cctcccaggt  32280
tcaaaccatt ctcctgcctc agcctcctga gtagctggaa ttacaggcat gcgccaccac  32340
gctcggctaa ttttgtattt ttagtggaaa cgggttttct ccatgttgtt caggctggtc  32400
ttgaactcct gacctcaggt gatccgcccg cctcaggctc ccaaagtgct gggattacag  32460
gcatgagcca gcacacctga cctgttattc caatttaaca gttctttctt cccatacctg  32520
taaatgtgtg tgactgtgtg tgtgtgcatg tacactcaca cacacacaaa tacacaagtt  32580
caagtgaaat ctaaatgctt ggtaaaacag tccatgtgca ctaatttgca agagttgttg  32640
tgagggtaga gcttttgaat aaacataggt tgtcaaagga aaaactccct ctgtgtaagc  32700
cacaggacaa aggttttgaa acacctttgt tatctaaagc tggaaagaaa tgtcttgcct  32760
taaaagaatt tgcacattcg tacctctttc cacaaatacg tgaaaggacg tgcttttgaa  32820
```

-continued

```
gataagaaaa gtttaaattc tacaaaaaaa aaaaatctga tttgggcaga actcattgct  32880
ccctttctc tgtttctacc ttgttcttct ctgggtggat catttactac ttatactgtc  32940
agtgttggtg ttgcttgttt acttagatcc ctgaagtcga gttgcacaac tccagggggc  33000
attcagataa aatatcatgt gaatgatgcc ctggagtttt gcaggtagct ttgtcctgaa  33060
gacagggaca aaaatgtttc atctctttac ctcccagtgc ctggtggaca tgccttcgga  33120
ccaagtagtt gcacaattca ttgttgctta gcaaatgaac aaatatgttc acctcactaa  33180
atagctgaca tgaaaacatt ttaaaaatag tatcaagata tttaaacagt cgattttatg  33240
aatttaaaag acacctagag atactacaat tccgtagttt tttagattaa aaaacaaaga  33300
cccaaagtct atatttttta aaggaaggcc cagatggttt tgtgaaggtc atgtgagtat  33360
ttagggacaa aactagagct gaaactcaat tctcttggcc ccaggtgatc ttctcactcc  33420
accagactta ctcagttcac atcacagtca caattcagat tagagctatg aacaattcta  33480
tccatttgca caattctaac tggtgtttct aacttcatta aaagactctg aattattttt  33540
cttatatacc tctaatcaag atcatttggt attatcctgc atatgttcaa atgttaccta  33600
tctacagata tttgaactta ggtggggaat atctccacaa agtccattaa gtaagttcag  33660
ttttagtgaa aactgagatg gtgcagcttg agagattaag tgtagaattt ccaatgtaat  33720
gctttgaatg tgtaccttaa atctgtatca ctggcttatt ctgggaattg aagtcttatt  33780
tcatttctca gagaatgatg gttctgctac cagtaatctt taagggttag atcattcggg  33840
ttttttgttt gtttgagact aaataaatga agaaaacaca tgttagatac aaaacactag  33900
aaatatatta attttcactg gagcgacacc aaaggccatc gacattaaaa atgaactcct  33960
aagttctttg caattcccca ggtatagatt taatatacaa cacatgcatc tcttgaaact  34020
ctttctttgc tagtaagaat tattctcctg aaatacccac ctgtcaaaaa gaaaggtaac  34080
attattgatt tttagaattc ttatttctgt cgtgtcagta agcaataccg gaaagaaaat  34140
caaacactca ggagaattgg catgatggtg aaggttgagc ttacaagtac agtggactca  34200
agtatccatg atccagcgca ctgagcaata aatccaaatg agcagtgacc acaggaaaac  34260
aatatgcagg gaggcctcgc tgggaaaagc taaactttta tatatgggaa tagtctatgg  34320
aggattacag gggatgtttt cttgggggta taaggtctgg agtgtgcagt actgggtgaa  34380
gcccttatct aacaggcaac agaaaggtct tcccaggtta ggcacacgtg actctacctc  34440
caacacagaa tttttttttt taagaaagca acagaaattt gcaaatgata gtctggtctt  34500
ttgtcctctc aattttaaag caaataacca gtattgtgtt atctaccttt tcatggatgc  34560
atccagtgtg cctagaaggg ccagacttta ttctgtattt gcaacaaaag tagacccagc  34620
aactgatggg aagatatctg attgggaagc agaagcagct ggtattttaa atcaggatga  34680
aagctaagat tttaggactc acttttgata ggaagaaagg atatatcaat tttcctttta  34740
atgagtggga tttttgaggt actttgtggg gcctctggtt caagactgtg gccagtgtgg  34800
tgttgtagga ggggcactga tggagagcta tcccggtgca ttatttctga gccacctctg  34860
tgcactttac ttcctcattt gtaacatggg actaatgtgc cctgctgagt cctcagagtt  34920
gctgcaacaa tcaaatgagc tattaaggga taagctcttt tccagctacc tatgagaatg  34980
ggtatgatat ggtcccagaa tttgctctct agagccacag aaatctctta acccctacaa  35040
gaactcttta aagttgttat ccccattata tagatgagga aactgagact tagacaaaaa  35100
gttgtccaag atcacataat attaaggaac agagctggga tgaatatttg agtctaattc  35160
```

-continued

```
caaaacattc tggaataact caatatgtgg ttttccattt ctcccaaaaa caggtacctg  35220
ctttttttcag tggcttgtgt tccagctgac agctccaggg cctgtttgaa taattcgaag  35280
acaatcctta gttaggaaag caagctttaa ttatcactgg ggaacagaag gccgcatctt  35340
cgaggaattt ggcagacctc agcagggggc aaccacaggc ctttggcaaa agatcacttt  35400
tcaacaacat tgtcaattcc agtgaccccc gaccttccac ctgcaggtcc ctgaacagct  35460
gctgttctgt gggaagcagt ggcagtctgt cttcctttaa aaggcacatg cacactctgt  35520
ccctgctgcc tgctgagatc ccacctggga cctcatcccc agagctgggg gtcatctccc  35580
atatcaagaa attaagaaaa ataagggggg gcaggaaagg acagctttga caacagtccc  35640
tgaactttcc cttttaatat aagccagatt taacgtatgt cattctgtaa atccgggagt  35700
ccaatttgag gcttgtaatt tgctgcaagc ttccctgttc ctccaagtgg ggtggagcta  35760
tgccaagcac atcaaggtaa ctggtggaag atataatttc cccactgtga gcctgcattt  35820
cagttcccta ttgtaatttt tatttgtgtt gaggttttgt ggttttaaaa aagtcaacca  35880
gatttatttt taaattaacc cagcccaaca tcaaaggcaa taagtagagg atgtttaggt  35940
attataaaga aaccctgtgt aatctgttat agctgtattc tttctcaggg catgtaatgg  36000
taaatggtta ggggcctttc acaaccaact ttctatattt ctctgacctc ggactaccct  36060
catgggcaaa aaaccctttt tgaggggatt tagtagcccc tctctcctcc tcctcaacct  36120
cttaatctaa tcctgtttgt aacgcaacat gctgcatgaa gaatacgaaa catgggctta  36180
agtccctccc cacttccctt atgactgtgg tttactttta gatatgaaga actctttcag  36240
gccaaaaaaa aaaaaagggg gggaccattt ggttaacgaa ccattttctt tggtaggcag  36300
gagaaagttt atattgaaag tttatcttaa ggatgacagg tcatacctga agggtttgtt  36360
ttggaatact gtggattttt tctaacccaa ataattacaa gagagttcct tgtttattgg  36420
ctcatggagg aaattcaagc gcctctgttc taggcatttt aagtgctctg tatatatggt  36480
ggttgttcct caaaacagct ttgggtttgt tttttgtttt ttgttgttag tggtggtttt  36540
ttgagataga gtctcgctct gttacccagg ctggagtgca gtggcgcaat ctcggctcac  36600
tgcaccctcc acctctctgg ttcaaaagat tctcctgcct cagcctcctg agtagctggg  36660
attacaggcg cccgccacca tgcccagcta atttttgtat ttttagtaga gacggggttt  36720
ccccatgttg gccaggctgg tctcgaactc ctgacctcag gtgattcacc cgcctgggcc  36780
ttccaaaatg ctgggattac aggcgtgagc caccatggct ggcccaaaac agctttttaa  36840
gaaaagtgct attaacccca tttacagatg agcacatttg agccacaccc tcttttccac  36900
actctaaatc ttgtctcttt ctttaaacat gagttactta tacttctgag cataactgag  36960
gcacttttag agacagtgtc ttctaagctc aatgtgatat tatttgtgct gctgtgctgc  37020
tactgggtaa ccagcaccca tcctggtcac caggtaact ttgtcaacca agaaggccaa  37080
ggatcccaaa ccagcatttt ctactatcaa aagagaggtt ctgcaaatcc actggcagga  37140
gagaaaatat aatagcaggt ggcatttata tgacccagtg tgcatggcag tgtcccaggg  37200
tatcaccgtg aatctcagaa actccaggct ttccccatgg gaaatccaca ccaccacaga  37260
tccagtggag gactcggtca agactcctga aatcaaagaa ctcacagtga ctgattcttt  37320
ccctagtttt ataatataaa taatggcatg gggtcacatt cagccgtcat tatccacatc  37380
atttcactga tgggatcctc ctcagacaga gattgggaat cagatttctc ggtcacataa  37440
actgttgctc attctgtgag gctgcctatt tgtaaagttg tggttcttat taaaagcaat  37500
ctcagacgta gcaagcaccc ctcacttccc ttctcattca ttttgttaaa gcaaatgggc  37560
```

-continued

```
tttggaattc aggcctgttt ctaccactta ctaatgttgt taatttggag gagttcctca  37620
actttgccaa ggcttgattt tctctgctgt aaagagggaa taataaacct attttacaga  37680
gcagctgaga caattaggtg agttaatgta tataaaatgg tttgcataat acccaacaca  37740
tattaaactc tcactcggtt tttaatatta acctctatgt gcttaataac attgaagaag  37800
aagattcaag tagattatag tctgttaaag agttcaaata taaataaata attctcaggg  37860
tgagaattgc catagcatag atatgttacg tacccatggc agagcgtgag gtggcagcat  37920
ctaatggttg agggagttgg gtgagacatc aagagaaggt gacatatttt tttgagtacc  37980
cagtggaagg catgggatac catgtggatc tctgcagtag attaaatata gacttgaact  38040
aacctatcct ggaacaatag gacaatatcc ttgtggctta cagtaattat tccctgcacc  38100
tatattgatt tgtttattaa acgaatagct ttattggtaa acatgtatat tgcggaagta  38160
gacttggtta tcattcccac aagtccagtt aaagtaatgg catctatata aaaaactcat  38220
aaaaactaga tatgtaagta atcaataaaa tactcttctc aagtattcag gagaaaaaat  38280
gtgttgaaat gatgattcat cattccacat aacgtatttg tgactacatt taatagcctc  38340
attagcaata aaatttttat gagttaacat catatgagaa tattcccttg taccttaccg  38400
agactttatc tgtagatttg taacataacc ataatcatct tggtatgttt cttacacatt  38460
ttattcagtg aacccaaatg aacttctaat tacatgttca gctgccagtc atggttttat  38520
atgtttgaat atatatacct tcagaggata tttgctcttt ggggtggtga agacttcatc  38580
ttcttataaa tgcaaacaga agatagttgg aagaggaaaa tgttttagca gtgtctcaat  38640
tatctctcct taatgattat ttcacaacct cgagatattt tcctaaaaga ctaagtaaga  38700
aatatatagt aagattcctt tctggatatt ttcagaactc ctagttataa ctatgcacca  38760
aatatggata aacactggat tatgcagtac acaggaccaa tgctgcccat ccacatggaa  38820
tttacaaaca ttctacagcg caaaaggctc cagactttga tgtcagtgga tgattctgtg  38880
gagagggtaa gcacatgaac ctacctcagt gatagttttt ggcccagctt cctttgtgta  38940
gacttattct tgccaatcct gtttggtttt ttccccttca ttttccagca tcattttgag  39000
agagaaagaa agagagagag tatgtgttta gtggcttaat catccctccc ttatcttgtc  39060
ctcattccat ctacctctcc agggttggtt tcttatggag ccagtaaaaa agaggagaga  39120
aaaatcaaat cagcgtagat caggggccac atcctcaaag gcaataaaga attgatggag  39180
cttgtgctga acttgaactt taagttaagg gccccatcta aaggaacagc aattactcag  39240
ctccagctaa attttgccat gtagaaatgt ggatcaagta tcagcaggtc ttctgacttt  39300
tttaaagaag ccagaaacac aaaaaatttt atttgaaatt ttctgaactt tgaaacatag  39360
tataagccaa acaagacgtg cctcaggctg gatttaactg gatcaggctc agaagcagcc  39420
tgtttttaac ccttggtaat tagatatgtg atgataattt taacaatgga ttttcaaagt  39480
acaacctata aagtttgatg gtagaggttg ttgtgcgggg tgtttttgtt tttgttctac  39540
caaacaagca aacaaaaagc ctaaaagtag aatgtgctag attccaaaaa gttacatttc  39600
acctttacca ttggaccttt ccctcccaga ctgtaagcaa atagaaaatg tggataatgt  39660
tattaaagca actcttgcct tttaaaaata acaggaaaaa gatttggggg caatcgtggc  39720
aacactattg agcatcatct tataccagca caattgattc tgacttgttc ctttgctgta  39780
tttcagctgt ataacatgct cgtggagacg gggagctgg agaatactta catcatttac  39840
accgccgacc atggttacca tattgggcag tttggactgg tcaaggggaa atccatgcca  39900
```

-continued

```
tatgactttg atattcgtgt gccttttttt attcgtggtc caagtgtaga accaggatca  39960
atgtacgtat ttctctgttt gcaacattca actgtcgtac ctcaagtgtg tctaagataa  40020
ttcaattacc agtctcagta tctggtttcc tttcatccaa aacaaaaaag gatgtgtgta  40080
ggctggttaa tttcgaagat gaaaaccttt tcctccctgc cacatcttaa attagctcaa  40140
gtatactact taaagagaaa ggaaaaataa gtgtatcaat gactaattct ctcaaattga  40200
ctggaatcta tgtctttttg gtctgtgtgc acagacagga tgtgatcttc tgggatatca  40260
cccttctttg aatcagagat acgctgtcat ttaaaaaaaa aacctgacac catcctttta  40320
gtgtttaact tttaaaaatt attccgaaag aaatgttttt aaaagataaa ttttgaaaag  40380
ctggcttttc ttttaaagga aaaagagcta aaggactagg ctgctatttc tgtcactgta  40440
ggcaggtcac tgcttctctt tgcatctcta ttttcccatc atgaaatggc cttgcctatt  40500
ttcccatcat aaaatggcct tgtcaatcat ctcaggatgt tttgaataaa atgggattgc  40560
atccatgaaa gaattatgga aagactaaaa gaaaaagtgg aagtagaatc cagaagctgg  40620
aatggccctt gaaaagcatc tagcctggac ccctgatgta acagtgaagc taggcagaca  40680
gcgtcagtgc ccctctcaga tccctgattc tggaagtggt ggcagtgggg cccagagccc  40740
agatgttctg aatctccccc gagtaccaca tgtgctgctg catcatacta catcctggag  40800
agagggcaat tgaagtaaga aaggtttctt tgaagaatgt tattgtgctt cctaagatta  40860
ttagaaacac cctgagaatt gtcagatcta tatctagaag gctttatgtt ttaaggacta  40920
gatagcatag attgaattca actgtaaaaa ctgtacatcc ttttttaaaa tattgatttt  40980
aaagctcttg ttcaacggaa aagttatgga ctattgggtt ttaagcaaaa gtatgcttgc  41040
tgcaaaaacc atgtatcagg ctgcatcttg cctggtgatg tggtcagaat acaggggtgc  41100
aggcatctct ccagcctgac cctggcaaga gtcagttaat cttgctcagt gccattgctg  41160
tgatcacaca cccacccttg ccacacaact acccatgcct aggagaccag atgagagggt  41220
gagaagagtt gaaggccaat gagtcactgc tgtagaaaaa gcagccctaa gtgccacctt  41280
cccctggcat tggatctcag ccatcaccgt gtgccccttt acagagtccc acagatcgtt  41340
ctcaacattg acttggcccc cacgatcctg gatattgctg ggctcgacac acctcctgat  41400
gtggacggca agtctgtcct caaacttctg gacccagaaa agccaggtaa caggtgtgtc  41460
attgttcctc ctctcagcca gccccaaata cactgagctc cagctggtgc ccagagccag  41520
ccagcagctg aagacatgga ggcagaatat gccttgccca caaggatcac cccaagctga  41580
gcatttctca gctgcttgtg aatagcatat tgatggagat gcactcatgg tctgtgggaa  41640
gtgagaggtg tttctttaaa taagctgtta gcacagatcc atttggaaaa acgtccagat  41700
gccaaaagta aatattatca ttttgctttc aggtttcgaa caaacaagaa ggccaaaatt  41760
tggcgtgata cattcctagt ggaaagaggg taattattgg ttcctggggt gcttctggga  41820
accagtccta gtgggcagct ttccctgctg agtatttttt ttctccttat ttttgtttac  41880
taagcatgca gatttcgtaa acctagtcac aagattgaat ggtttgctgc ttattctgta  41940
gtggtcaata gagtaataat tgctggatca gaattgtaaa gaataaccct caagttggtt  42000
aattggtaca aaaacacagt tagatagaag ttatagaatt tgatagtata gttgggacat  42060
tatcgttaac aataatttat gtatatctta aaatagctag aagtgaagaa ttgcaaagtt  42120
cccaacacaa ggaaaagata aatgagatga tgaatatccc aattatcttg atttgatcat  42180
tacacattgt agactggtat ccatatatca cacgtacccc caaaatatgt ataattgtga  42240
tatatcaatt tttaaaatac caaaaaagca agagaatgac gactccacat cccccaaaaa  42300
```

-continued

```
gaataaattc tcataagctt ggaccaaagc ctttatcatg ggtgtagatt tactgttgca  42360

tttctcagtg ctggtttcta atcagaccag tggattgagt ttctctacca tcctccccac  42420

gttcttctct aagctgcctc caagcctcac ccggcaccct tcttcctact tcctacttct  42480

tttccttgtg tgcctttcct agttttaaat agataaatgt atgccattgt aattatttcc  42540

attgtcactt ctgggtttcc ccttttggtt c                                 42571


<210> SEQ ID NO 4
<211> LENGTH: 360
<212> TYPE: PRT
<213> ORGANISM: Human

<400> SEQUENCE: 4

Met Lys Tyr Ser Cys Cys Ala Leu Val Leu Ala Val Leu Gly Thr Glu
 1               5                  10                  15

Leu Leu Gly Ser Leu Cys Ser Thr Val Arg Ser Pro Arg Phe Arg Gly
            20                  25                  30

Arg Ile Gln Gln Glu Arg Lys Asn Ile Arg Pro Asn Ile Ile Leu Val
        35                  40                  45

Leu Thr Asp Asp Gln Asp Val Glu Leu Gly Ser Leu Gln Val Met Asn
    50                  55                  60

Lys Thr Arg Lys Ile Met Glu His Gly Gly Ala Thr Phe Ile Asn Ala
65                  70                  75                  80

Phe Val Thr Thr Pro Met Cys Cys Pro Ser Arg Ser Ser Met Leu Thr
                85                  90                  95

Gly Lys Tyr Val His Asn His Asn Val Tyr Thr Asn Asn Glu Asn Cys
            100                 105                 110

Ser Ser Pro Ser Trp Gln Ala Met His Glu Pro Arg Thr Phe Ala Val
        115                 120                 125

Tyr Leu Asn Asn Thr Gly Tyr Arg Thr Ala Phe Phe Gly Lys Tyr Leu
    130                 135                 140

Asn Glu Tyr Asn Gly Ser Tyr Ile Pro Pro Gly Trp Arg Glu Trp Leu
145                 150                 155                 160

Gly Leu Ile Lys Asn Ser Arg Phe Tyr Asn Tyr Thr Val Cys Arg Asn
                165                 170                 175

Gly Ile Lys Glu Lys His Gly Phe Asp Tyr Ala Lys Asp Tyr Phe Thr
            180                 185                 190

Asp Leu Ile Thr Asn Glu Ser Ile Asn Tyr Phe Lys Met Ser Lys Arg
        195                 200                 205

Met Tyr Pro His Arg Pro Val Met Met Val Ile Ser His Ala Ala Pro
    210                 215                 220

His Gly Pro Glu Asp Ser Ala Pro Gln Phe Ser Lys Leu Tyr Pro Asn
225                 230                 235                 240

Ala Ser Gln His Ile Thr Pro Ser Tyr Asn Tyr Ala Pro Asn Met Asp
                245                 250                 255

Lys His Trp Ile Met Gln Tyr Thr Gly Pro Met Leu Pro Ile His Met
            260                 265                 270

Glu Phe Thr Asn Ile Leu Gln Arg Lys Arg Leu Gln Thr Leu Met Ser
        275                 280                 285

Val Asp Asp Ser Val Glu Arg Leu Tyr Asn Met Leu Val Glu Thr Gly
    290                 295                 300

Glu Leu Glu Asn Thr Tyr Ile Ile Tyr Thr Ala Asp His Gly Tyr His
305                 310                 315                 320
```

-continued

```
Ile Gly Gln Phe Gly Leu Val Lys Gly Lys Ser Met Pro Tyr Asp Phe
                325                 330                 335

Asp Ile Arg Val Pro Phe Phe Ile Arg Gly Pro Ser Val Glu Pro Gly
            340                 345                 350

Ser Ile Val Pro Gln Ile Val Leu
        355                 360


<210> SEQ ID NO 5
<211> LENGTH: 307
<212> TYPE: PRT
<213> ORGANISM: Human

<400> SEQUENCE: 5

Asp Val Glu Leu Gly Ser Leu Gln Val Met Asn Lys Thr Arg Lys Ile
 1               5                  10                  15

Met Glu His Gly Gly Ala Thr Phe Ile Asn Ala Phe Val Thr Thr Pro
            20                  25                  30

Met Cys Cys Pro Ser Arg Ser Ser Met Leu Thr Gly Lys Tyr Val His
        35                  40                  45

Asn His Asn Val Tyr Thr Asn Asn Glu Asn Cys Ser Ser Pro Ser Trp
    50                  55                  60

Gln Ala Met His Glu Pro Arg Thr Phe Ala Val Tyr Leu Asn Asn Thr
65                  70                  75                  80

Gly Tyr Arg Thr Ala Phe Phe Gly Lys Tyr Leu Asn Glu Tyr Asn Gly
                85                  90                  95

Ser Tyr Ile Pro Pro Gly Trp Arg Glu Trp Leu Gly Leu Ile Lys Asn
            100                 105                 110

Ser Arg Phe Tyr Asn Tyr Thr Val Cys Arg Asn Gly Ile Lys Glu Lys
        115                 120                 125

His Gly Phe Asp Tyr Ala Lys Asp Tyr Phe Thr Asp Leu Ile Thr Asn
    130                 135                 140

Glu Ser Ile Asn Tyr Phe Lys Met Ser Lys Arg Met Tyr Pro His Arg
145                 150                 155                 160

Pro Val Met Met Val Ile Ser His Ala Ala Pro His Gly Pro Glu Asp
                165                 170                 175

Ser Ala Pro Gln Phe Ser Lys Leu Tyr Pro Asn Ala Ser Gln His Ile
            180                 185                 190

Thr Pro Ser Tyr Asn Tyr Ala Pro Asn Met Asp Lys His Trp Ile Met
        195                 200                 205

Gln Tyr Thr Gly Pro Met Leu Pro Ile His Met Glu Phe Thr Asn Ile
    210                 215                 220

Leu Gln Arg Lys Arg Leu Gln Thr Leu Met Ser Val Asp Asp Ser Val
225                 230                 235                 240

Glu Arg Leu Tyr Asn Met Leu Val Glu Thr Gly Glu Leu Glu Asn Thr
                245                 250                 255

Tyr Ile Ile Tyr Thr Ala Asp His Gly Tyr His Ile Gly Gln Phe Gly
            260                 265                 270

Leu Val Lys Gly Lys Ser Met Pro Tyr Asp Phe Asp Ile Arg Val Pro
        275                 280                 285

Phe Phe Ile Arg Gly Pro Ser Val Glu Pro Gly Ser Ile Val Pro Gln
    290                 295                 300

Ile Val Leu
305


<210> SEQ ID NO 6
```

-continued

```
<211> LENGTH: 309
<212> TYPE: PRT
<213> ORGANISM: Drosophila melanogaster

<400> SEQUENCE: 6

Arg Pro Asn Ile Ile Leu Ile Leu Thr Asp Asp Gln Asp Val Glu Leu
 1               5                  10                  15

Gly Ser Leu Asn Phe Met Pro Arg Thr Leu Arg Leu Leu Arg Asp Gly
            20                  25                  30

Gly Ala Glu Phe Arg His Ala Tyr Thr Thr Thr Pro Met Cys Cys Pro
        35                  40                  45

Ala Arg Ser Ser Leu Leu Thr Gly Met Tyr Val His Asn His Met Val
    50                  55                  60

Phe Thr Asn Asn Asp Asn Cys Ser Ser Pro Gln Trp Gln Ala Thr His
65                  70                  75                  80

Glu Thr Arg Ser Tyr Ala Thr Tyr Leu Ser Asn Ala Gly Tyr Arg Thr
                85                  90                  95

Gly Tyr Phe Gly Lys Tyr Leu Asn Lys Tyr Asn Gly Ser Tyr Ile Pro
            100                 105                 110

Pro Gly Trp Arg Glu Trp Gly Gly Leu Ile Met Asn Ser Lys Tyr Tyr
        115                 120                 125

Asn Tyr Ser Ile Asn Leu Asn Gly Gln Lys Ile Lys His Gly Phe Asp
    130                 135                 140

Tyr Ala Lys Asp Tyr Tyr Pro Asp Leu Ile Ala Asn Asp Ser Ile Ala
145                 150                 155                 160

Phe Leu Arg Ser Ser Lys Gln Gln Asn Gln Arg Lys Pro Val Leu Leu
                165                 170                 175

Thr Met Ser Phe Pro Ala Pro His Gly Pro Glu Asp Ser Ala Pro Gln
            180                 185                 190

Tyr Ser His Leu Phe Phe Asn Val Thr Thr His His Thr Pro Ser Tyr
        195                 200                 205

Asp His Ala Pro Asn Pro Asp Lys Gln Trp Ile Leu Arg Val Thr Glu
    210                 215                 220

Pro Met Gln Pro Val His Lys Arg Phe Thr Asn Leu Leu Met Thr Lys
225                 230                 235                 240

Arg Leu Gln Thr Leu Gln Ser Val Asp Val Ala Val Glu Arg Val Tyr
                245                 250                 255

Asn Glu Leu Lys Glu Leu Gly Glu Leu Asp Asn Thr Tyr Ile Val Tyr
            260                 265                 270

Thr Ser Asp His Gly Tyr His Leu Gly Gln Phe Gly Leu Ile Lys Gly
        275                 280                 285

Lys Ser Phe Pro Phe Glu Phe Asp Val Arg Val Pro Phe Leu Ile Arg
    290                 295                 300

Gly Pro Gly Ile Gln
305
```